(12) United States Patent
Yokoyama et al.

(10) Patent No.: US 8,293,512 B2
(45) Date of Patent: Oct. 23, 2012

(54) POLYPEPTIDE HAVING ACTIVITY OF AMINOACYL-TRNA SYNTHETASE AND USE THEREOF

(75) Inventors: Shigeyuki Yokoyama, Yokohama (JP); Kensaku Sakamoto, Yokohama (JP); Kenji Oki, Yokohama (JP); Takahito Mukai, Yokohama (JP)

(73) Assignee: Riken, Wako-Shi, Saitama (JP)

( * ) Notice: Subject to any disclaimer, the term of this patent is extended or adjusted under 35 U.S.C. 154(b) by 0 days.

(21) Appl. No.: 13/180,209

(22) Filed: Jul. 11, 2011

(65) Prior Publication Data

US 2012/0028330 A1 Feb. 2, 2012

Related U.S. Application Data

(63) Continuation of application No. 12/322,782, filed on Feb. 5, 2009, now abandoned.

(30) Foreign Application Priority Data

Feb. 8, 2008 (JP) .................................. 2008/29236

(51) Int. Cl.
*C12N 9/00* (2006.01)
*C07H 21/04* (2006.01)
(52) U.S. Cl. ........................ 435/183; 435/69.1; 536/23.2
(58) Field of Classification Search .......................... None
See application file for complete search history.

(56) References Cited

U.S. PATENT DOCUMENTS

2005/0084856 A1  4/2005  Kiga et al.

OTHER PUBLICATIONS

Summerer et al., "A genetically encoded fluorescent amino acid", PNAS, vol. 103, No. 26, pp. 9785-9789 (06/27/206).
Office Action in U.S. Appl. No. 12/322,782, mailed Jan. 27, 2010.
Office Action in U.S. Appl. No. 12/322,782, mailed Apr. 30, 2010.
Office Action in U.S. Appl. No. 12/322,782, mailed Jan. 11, 2011.
L. Wang et al., "Expanding the Genetic Code", *Angew. Chem. Int. Ed.*, vol. 44, pp. 34-66 (2005).
N. Lee et al., "Ribozyme-catalyzed tRNA Aminoacylation", *Nature Structural Biology*, 7(1), pp. 28-33 (2000).
A.R. Fersht et al., "Mechanism of Aminoacylation of tRNA. Proof of the Aminoacyl Adenylate Pathway for the Isoleucyl and Tyrosyl-tRNA Synthetases from *Escherichia coli* K12", *Biochemistry*, 15(4), pp. 818-823 (1976).
W. Freist et al., "Tyrosyl-tRNA synthetase from baker's yeast. Order of substrate addition, discrimination of 20 amino acids in aminoacylation of tRNA$^T$yr-C-C-A(3'NH$_2$)", *Eur. J. Biochem.*, vol. 177, pp. 425-433 (1988).
G. Eriani et al., "Partition of tRNA synthetases into two classes based on mutually exclusive sets of sequence motifs", *Nature*, vol. 347, pp. 203-206 (1990).

L. Pauling et al., "The Probability of Errors in the Process of Synthesis of Protein Molecules", *California Institute of Technology*, Pasadena, California, pp. 597-602 (1957).
T. Crepin et al., "Structures of Two Bacterial Prolyl-tRNA Synthetases with and without a *cis*-Editing Domain", *Structure*, vol. 14, pp. 1511-1525 (2006).
A.-C. Dock-Bregeon et al., "Transfer RNA-Mediated Editing in Threonyl-tRNA Synthetase: The Class II Solution to the Double Discrimination Problem", *Cell*, vol. 103, pp. 877-884 (2000).
S. Fukai et al., "Structural Basis for Double-Sieve Discrimination of L-Valine from L-Isoleucine and L-Threonine by the Complex of tRNA$^{val}$ and Valyl-tRNA Synthetase", *Cell*, vol. 103, pp. 793-803 (2000).
R. Fukunaga et al., "Aminoacylation complex strucutres of leucyl-tRNA synthetase and tRNA$^{Leu}$ reveal two modes of discriminator-base recognition", *Nature Structural & Molecular Biology*, 12(10), pp. 915-922 (2005).
L. Lin et al., "Aminoacylation error correction", *Nature*, vol. 384, pp. 33-34 (1996).
T.K. Nomanbhoy et al., "Transfer RNA-Dependent Translocation of Misactivated Amino Acids to Prevent Errors in Protein Synthesis", *Molecular Cell*, vol. 4, pp. 519-528 (1999).
O. Nureki et al., "Enzyme Structure with Two Catalytic Sites for Double-Sieve Selection of Substrate", *Science*, vol. 280, pp. 578-582 (1998).
H. Roy et al., "Post-transfer editing in vitro and in vivo by the β subunit of phenylalanyl-tRNA synthetase", *The EMBO Journal*, vol. 23, pp. 4639-4648 (2004).
B. Ruan et al., "The Bacterial YbaK Protein is a Cys-tRNA$^{Pro}$ and Cys-tRNA$^{Cys}$ Deacylase", *The Journal of Biological Chemistry*, 280(27), pp. 25887-25891 (2005).
M. Sokabe et al., "Molecular basis of alanine discrimination in editing site", *PNAS*, 102(33), pp. 11669-11674 (2005).
M.A. Swairjo et al., "Alanyl-tRNA Synthetase Crystal Structure and Design for Acceptor-Stem Recognition", *Molecular Cell*, vol. 13, pp. 829-841 (2004).
O. Kotik-Kogan et al., "Structural Basis for Discrimination of L-Phenylalanine from L-Tyrosine by Phenylalanyl-tRNA Synthetase", *Structure*, vol. 13, pp. 1799-1807 (2005).
L. Ribas de Pouplana et al., "Two Classes of tRNA Synthetases Suggested by Sterically Compatible Dockings on tRNA Acceptor Stem", *Cell*, vol. 104, pp. 191-193 (2001).
A. Fersht et al., "Probing the Limits of Protein-Amino Acid Side Chain Recognition with the Aminoacyl-tRNA Synthetases. Discrimination against Phenylalanine by Tyrosyl-tRNA Synthetases" *Biochemistry*, vol. 19, pp. 5520-5524 (1980).
L. Wang et al., "Expanding the Genetic Code", *Annu. Rev. Biophys. Biomol. Struct.*, vol. 35, pp. 225-249 (2006).
L. Wang et al., "Expanding the Genetic Code of *Escherichia coli*", *Science*, vol. 292, pp. 498-500 (2001).

(Continued)

*Primary Examiner* — Kagnew H Gebreyesus
(74) *Attorney, Agent, or Firm* — Edwards Wildman Palmer LLP; David G. Conlin, Esq.; Elbert Chiang

(57) ABSTRACT

A polypeptide according to the present invention includes: an altered polypeptide obtained by altering an ArgRS, a CysRS, a MetRS, a GlnRS, a GluRS, a LysRS, a TyrRS, or a TrpRS so that an unnatural amino acid is recognized; and an editing polypeptide derived from a PheRS, a LeuRS, an IleRS, a ValRS, an AlaRS, a ProRS, or a ThrRS, the editing polypeptide having been either inserted between a Rossman-fold N domain and a Rossman-fold C domain that exist in the altered polypeptide, or bound to an N terminal of the altered polypeptide. Thus provided are a new aaRS that exhibits high substrate specificity to an unnatural amino acid and a technique that involves the use of such an aaRS.

14 Claims, 6 Drawing Sheets

OTHER PUBLICATIONS

E.M. Tippmann et al., "A Genetically Encoded Diazirine Photocrosslinker in *Escherichia coli*", *ChemBioChem*, vol. 8, pp. 2210-2214 (2007).

J. Xie et al., "A Genetically Encoded Metabolically Stable Analogue of Phosphotyrosine in *Escherichia coli*", *ACS Chemical Biology*, 2(7), pp. 474-478 (2007).

Z. Zhang et al., "The Selective Incorporation of Alkenes into Proteins in *Escherichia coli*", *Angew. Chem. Int. Ed.*, 41(15), pp. 2840-2842 (2002).

C.C. Liu et al., "Recombinant expression of selectively sulfated proteins in *Escherichia coli*", *Nature Biotechnology*, 24(11), pp. 1436-1440 (2006).

H.M. Sasaki et al., "Structural and Mutational Studies of the Amino Acid-Editing Domain from Archaeal/Eukaryal Phenylalanyl-tRNA Synthetase", *PNAS*, 103(40), pp. 14744-14749 (2006).

T.L. Lincecum, Jr., et al., "Structural and Mechanistic Basis of Pre and Posttransfer Editing by Leucyl-tRNA Synthetase", *Molecular Cell*, vol. 11, pp. 951-963 (2003).

K. Beebe et al., "Distinct domains of tRNA synthetase recognize the same base pair", *Nature*, vol. 451, pp. 90-93 (2008).

D. Korencic et al., "A freestanding proofreading domain is required for protein synthesis quality control in Archaea", *PNAS*, 101(28), pp. 10260-10265 (2004).

K. Katoh et al., "MAFFT: a novel method for rapid multiple sequence alignment based on fast Fourier transform", *Nucleic Acids Research*, 30(14), pp. 3059-3066 (2002).

K. Katoh et al., "MAFFT version 5: improvement in accuracy of multiple sequence alignment", *Nucleic Acids Research*, 33(2), pp. 511-518 (2005).

O. Nureki et al., "Molecular Recognition of the Identity-determinant Set of Isoleucine Transfer RNA from *Escherichia coli*", *J. Mol. Biol.*, vol. 236, pp. 710-724 (1994).

D. Kiga et al., "An engineered *Escherichia coli* tyrosyl-tRNA synthetase for site-specific incorporation of an unnatural amino acid into proteins in eukaryotic translation and its application in a wheat germ cell-free system", *PNAS*, 99(15), pp. 9715-9723 (2002).

K. Sakamoto et al., "Site—specific incorporation of an unnatural amino acid into proteins in mammalian cells", *Nucleic Acids Research*, 30(21), pp. 4692-4699 (2002).

M. Wakiyama et al., "Drosophila U6 promoter-driven short hairpin RNAs effectively induce RNA interference in Schneider 2 cells", *Biochemical and Biophysical Research Communications*, vol. 331, pp. 1163-1170 (2005).

M. Ibba et al., "Substrate specificity is determined by amino acid binding pocket size in *Escherichia coli* Phenylalanyl-tRNA synthetase", *Biochemistry*, 33, pp. 7107-7112 (1994).

K. Kirshenbaum et al., "Biosynthesis of proteins incorporating a versatile set of phenylalanine analogues", *ChemBioChem*, 02-03, pp. 235-237 (2002).

J. Xie et al., "The site-specific incorporation of *p*-iodo-L-phenylalanine into proteins for structure determination", *Nature Biotechnology*, 22(10), pp. 1297-1301 (2004).

```
                          SEQUENCE LISTING

<160> NUMBER OF SEQ ID NOS: 73

<210> SEQ ID NO 1
<211> LENGTH: 424
<212> TYPE: PRT
<213> ORGANISM: Escherichia coli

<400> SEQUENCE: 1

Met Ala Ser Ser Asn Leu Ile Lys Gln Leu Gln Glu Arg Gly Leu Val
 1               5                  10                  15

Ala Gln Val Thr Asp Glu Glu Ala Leu Ala Glu Arg Leu Ala Gln Gly
                20                  25                  30

Pro Ile Ala Leu Val Cys Gly Phe Asp Pro Thr Ala Asp Ser Leu His
            35                  40                  45

Leu Gly His Leu Val Pro Leu Leu Cys Leu Lys Arg Phe Gln Gln Ala
        50                  55                  60

Gly His Lys Pro Val Ala Leu Val Gly Gly Ala Thr Gly Leu Ile Gly
 65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
                100                 105                 110

Asp Phe Asp Cys Gly Glu Asn Ser Ala Ile Ala Ala Asn Asn Tyr Asp
            115                 120                 125

Trp Phe Gly Asn Met Asn Val Leu Thr Phe Leu Arg Asp Ile Gly Lys
        130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Asp Phe Ala Cys Leu Asn Lys Gln Tyr Gly Val
                180                 185                 190

Val Leu Cys Ile Gly Gly Ser Asp Gln Trp Gly Asn Ile Thr Ser Gly
            195                 200                 205

Ile Asp Leu Thr Arg Arg Leu His Gln Asn Gln Val Phe Gly Leu Thr
        210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
                260                 265                 270

Lys Phe Phe Thr Phe Met Ser Ile Glu Glu Ile Asn Ala Leu Glu Glu
            275                 280                 285

Glu Asp Lys Asn Ser Gly Lys Ala Pro Arg Ala Gln Tyr Val Leu Ala
        290                 295                 300

Glu Gln Val Thr Arg Leu Val His Gly Glu Glu Gly Leu Gln Ala Ala
305                 310                 315                 320
```

```
Lys Arg Ile Thr Glu Cys Leu Phe Ser Gly Ser Leu Ser Ala Leu Ser
            325                 330                 335

Glu Ala Asp Phe Glu Gln Leu Ala Gln Asp Gly Val Pro Met Val Glu
        340                 345                 350

Met Glu Lys Gly Ala Asp Leu Met Gln Ala Leu Val Asp Ser Glu Leu
    355                 360                 365

Gln Pro Ser Arg Gly Gln Ala Arg Lys Thr Ile Ala Ser Asn Ala Ile
370                 375                 380

Thr Ile Asn Gly Glu Lys Gln Ser Asp Pro Glu Tyr Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420
```

<210> SEQ ID NO 2
<211> LENGTH: 194
<212> TYPE: PRT
<213> ORGANISM: Pyrococcus horikoshii

<400> SEQUENCE: 2

```
Glu Val Lys Lys Ser Asn Val Thr Val Tyr Val Asp Glu Lys Leu Lys
1               5                   10                  15

Asp Ile Arg Pro Tyr Gly Val Tyr Ala Ile Val Glu Gly Leu Arg Leu
            20                  25                  30

Asp Glu Asp Ser Leu Ser Gln Met Ile Gln Leu Gln Glu Lys Ile Ala
        35                  40                  45

Leu Thr Phe Gly Arg Arg Arg Glu Val Ala Ile Gly Ile Phe Asp
    50                  55                  60

Phe Asp Lys Ile Lys Pro Pro Ile Tyr Tyr Lys Ala Ala Glu Lys Thr
65                  70                  75                  80

Glu Lys Phe Ala Pro Leu Gly Tyr Lys Glu Met Thr Leu Glu Glu
                85                  90                  95

Ile Leu Glu Lys His Glu Lys Gly Arg Glu Tyr Gly His Leu Ile Lys
            100                 105                 110

Asp Lys Gln Phe Tyr Pro Leu Leu Ile Asp Ser Glu Gly Asn Val Leu
        115                 120                 125

Ser Met Pro Pro Ile Ile Asn Ser Glu Phe Thr Gly Arg Val Thr Thr
    130                 135                 140

Asp Thr Lys Asn Val Phe Ile Asp Val Thr Gly Trp Lys Leu Glu Lys
145                 150                 155                 160

Val Met Leu Ala Leu Asn Val Met Val Thr Ala Leu Ala Glu Arg Gly
                165                 170                 175

Gly Lys Ile Arg Ser Val Arg Val Val Tyr Lys Asp Phe Glu Ile Glu
            180                 185                 190

Thr Pro
```

<210> SEQ ID NO 3
<211> LENGTH: 627
<212> TYPE: PRT
<213> ORGANISM: Artificial Sequence
<220> FEATURE:
<223> OTHER INFORMATION: Description of Artificial
      Sequence:P.horikoshii-E.coli

<400> SEQUENCE: 3

```
Met Ala Ser Ser Asn Leu Ile Lys Gln Leu Gln Glu Arg Gly Leu Val
1               5                   10                  15
```

```
Ala Gln Val Thr Asp Glu Glu Ala Leu Ala Glu Arg Leu Ala Gln Gly
            20                  25                  30
Pro Ile Ala Leu Val Cys Gly Phe Asp Pro Thr Ala Asp Ser Leu His
        35                  40                  45
Leu Gly His Leu Val Pro Leu Leu Cys Leu Lys Arg Phe Gln Gln Ala
    50                  55                  60
Gly His Lys Pro Val Ala Leu Val Gly Gly Ala Thr Gly Leu Ile Gly
65                  70                  75                  80
Asp Pro Ser Phe Lys Ala Ala Glu Arg Lys Leu Asn Thr Glu Glu Thr
                85                  90                  95
Val Gln Glu Trp Val Asp Lys Ile Arg Lys Gln Val Ala Pro Phe Leu
            100                 105                 110
Asp Phe Asp Cys Gly Glu Asn Ser Ala Ile Ala Ala Asn Asn Tyr Asp
        115                 120                 125
Trp Phe Gly Asn Met Asn Val Leu Thr Phe Leu Arg Asp Ile Gly Lys
    130                 135                 140
His Phe Ser Val Asn Gln Met Ile Asn Lys Glu Ala Val Lys Gln Arg
145                 150                 155                 160
Leu Asn Arg Glu Asp Gln Glu Val Lys Ser Asn Val Thr Val Tyr
                165                 170                 175
Val Asp Glu Lys Leu Lys Asp Ile Arg Pro Tyr Gly Val Tyr Ala Ile
            180                 185                 190
Val Glu Gly Leu Arg Leu Asp Glu Asp Ser Leu Ser Gln Met Ile Gln
        195                 200                 205
Leu Gln Glu Lys Ile Ala Leu Thr Phe Gly Arg Arg Arg Glu Val
    210                 215                 220
Ala Ile Gly Ile Phe Asp Phe Asp Lys Ile Lys Pro Pro Ile Tyr Tyr
225                 230                 235                 240
Lys Ala Ala Glu Lys Thr Glu Lys Phe Ala Pro Leu Gly Tyr Lys Glu
                245                 250                 255
Glu Met Thr Leu Glu Glu Ile Leu Glu Lys His Glu Lys Gly Arg Glu
            260                 265                 270
Tyr Gly His Leu Ile Lys Asp Lys Gln Phe Tyr Pro Leu Leu Ile Asp
        275                 280                 285
Ser Glu Gly Asn Val Leu Ser Met Pro Pro Ile Ile Asn Ser Glu Phe
    290                 295                 300
Thr Gly Arg Val Thr Thr Asp Thr Lys Asn Val Phe Ile Asp Val Thr
305                 310                 315                 320
Gly Trp Lys Leu Glu Lys Val Met Leu Ala Leu Asn Val Met Val Thr
                325                 330                 335
Ala Leu Ala Glu Arg Gly Gly Lys Ile Arg Ser Val Arg Val Val Tyr
            340                 345                 350
Lys Asp Phe Glu Ile Glu Thr Pro Gly Ser Ala Ser Gly Pro Ala Ser
        355                 360                 365
Ala Gly Ile Ser Phe Thr Glu Phe Ser Tyr Asn Leu Leu Gln Gly Tyr
    370                 375                 380
Asp Phe Ala Cys Leu Asn Lys Gln Tyr Gly Val Val Leu Cys Ile Gly
385                 390                 395                 400
Gly Ser Asp Gln Trp Gly Asn Ile Thr Ser Gly Ile Asp Leu Thr Arg
                405                 410                 415
Arg Leu His Gln Asn Gln Val Phe Gly Leu Thr Val Pro Leu Ile Thr
            420                 425                 430
Lys Ala Asp Gly Thr Lys Phe Gly Lys Thr Glu Gly Gly Ala Val Trp
```

```
                435               440               445
Leu Asp Pro Lys Lys Thr Ser Pro Tyr Lys Phe Tyr Gln Phe Trp Ile
    450               455               460

Asn Thr Ala Asp Ala Asp Val Tyr Arg Phe Leu Lys Phe Phe Thr Phe
465               470               475               480

Met Ser Ile Glu Glu Ile Asn Ala Leu Glu Glu Asp Lys Asn Ser
            485               490               495

Gly Lys Ala Pro Arg Ala Gln Tyr Val Leu Ala Glu Gln Val Thr Arg
            500               505               510

Leu Val His Gly Glu Glu Gly Leu Gln Ala Ala Lys Arg Ile Thr Glu
        515               520               525

Cys Leu Phe Ser Gly Ser Leu Ser Ala Leu Ser Glu Ala Asp Phe Glu
    530               535               540

Gln Leu Ala Gln Asp Gly Val Pro Met Val Glu Met Glu Lys Gly Ala
545               550               555               560

Asp Leu Met Gln Ala Leu Val Asp Ser Glu Leu Gln Pro Ser Arg Gly
                565               570               575

Gln Ala Arg Lys Thr Ile Ala Ser Asn Ala Ile Thr Ile Asn Gly Glu
            580               585               590

Lys Gln Ser Asp Pro Glu Tyr Phe Phe Lys Glu Glu Asp Arg Leu Phe
        595               600               605

Gly Arg Phe Thr Leu Leu Arg Arg Gly Lys Lys Asn Tyr Cys Leu Ile
    610               615               620

Cys Trp Lys
625

<210> SEQ ID NO 4
<211> LENGTH: 1272
<212> TYPE: DNA
<213> ORGANISM: Escherichia coli

<400> SEQUENCE: 4
atggcaagca gtaacttgat taaacaattg caagagcggg ggctggtagc ccaggtgacg    60
gacgaggaag cgttagcaga gcgactggcg caaggcccga tcgcgctcgt ttgcggcttc   120
gatcctaccg ctgacagctt gcatttgggg catcttgttc cattgttatg cctgaaacgc   180
ttccagcagg cgggccacaa gccggttgcg ctggtaggcg gcgcgacggg tctgattggc   240
gacccgagct tcaaagctgc cgagcgtaag ctgaacaccg aagaaactgt tcaggagtgg   300
gtggacaaaa tccgtaagca ggttgccccg ttcctcgatt tcgactgtgg agaaaactct   360
gctatcgcgg cgaacaacta tgactggttc ggcaatatga atgtgctgac cttcctgcgc   420
gatattggca acacttctc cgttaaccag atgatcaaca agaagcggt taagcagcgt   480 ctcaaccgtg aagatcaggg gatttcgttc actgagtttt cctacaacct gttgcagggt   540
tatgacttcg cctgtctgaa caaacagtac ggtgtggtgc tgtgcattgg tggttctgac   600
cagtggggta acatcacttc tggtatcgac ctgacccgtc gtctgcatca gaatcaggtg   660
tttggcctga ccgttccgct gatcactaaa gcagatggca ccaaatttgg taaaactgaa   720
ggcggcgcag tctggttgga tccgaagaaa accagcccgt acaaattcta ccagttctgg   780
atcaacactg cggatgccga cgtttaccgc ttcctgaagt tcttcacctt tatgagcatt   840
gaagagatca acgccctgga agaagaagat aaaaacagcg gtaaagcacc gcgcgcccag   900
tatgtactgg cggagcaggt gactcgtctg gttcacggtg aagaaggttt acaggcggca   960
aaacgtatta ccgaatgcct gttcagcggt tctttgagtg cgctgagtga agcggacttc  1020
```

```
gaacagctgg cgcaggacgg cgtaccgatg gttgagatgg aaaagggcgc agacctgatg    1080
caggcactgg tcgattctga actgcaacct tcccgtggtc aggcacgtaa aactatcgcc    1140
tccaatgcca tcaccattaa cggtgaaaaa cagtccgatc ctgaatactt ctttaaagaa    1200
gaagatcgtc tgtttggtcg ttttaccttg ctgcgtcgcg gtaaaaagaa ttactgtctg    1260
atttgctgga aa                                                       1272
```

<210> SEQ ID NO 5
<211> LENGTH: 216
<212> TYPE: PRT
<213> ORGANISM: Escherichia coli

<400> SEQUENCE: 5

```
Val Gln Pro Glu Ile Val Pro Val Gly Ala Thr Ile Asp Asp Thr Leu
  1               5                  10                  15

Pro Ile Thr Val Glu Ala Pro Glu Ala Cys Pro Arg Tyr Leu Gly Arg
             20                  25                  30

Val Val Lys Gly Ile Asn Val Lys Ala Pro Thr Pro Leu Trp Met Lys
         35                  40                  45

Glu Lys Leu Arg Arg Cys Gly Ile Arg Ser Ile Asp Ala Val Val Asp
     50                  55                  60

Val Thr Asn Tyr Val Leu Leu Glu Leu Gly Gln Pro Met His Ala Phe
 65                  70                  75                  80

Asp Lys Asp Arg Ile Glu Gly Ile Val Arg Met Ala Lys Glu
             85                  90                  95

Gly Glu Thr Leu Val Leu Leu Asp Gly Thr Glu Ala Lys Leu Asn Ala
            100                 105                 110

Asp Thr Leu Val Ile Ala Asp His Asn Lys Ala Leu Ala Met Gly Gly
        115                 120                 125

Ile Phe Gly Gly Glu His Ser Gly Val Asn Asp Glu Thr Gln Asn Val
    130                 135                 140

Leu Leu Glu Cys Ala Phe Phe Ser Pro Leu Ser Ile Thr Gly Arg Ala
145                 150                 155                 160

Arg Arg His Gly Leu His Thr Asp Ala Ser His Arg Tyr Glu Arg Gly
                165                 170                 175

Val Asp Pro Ala Leu Gln His Lys Ala Met Glu Arg Ala Thr Arg Leu
            180                 185                 190

Leu Ile Asp Ile Cys Gly Gly Glu Ala Gly Pro Val Ile Asp Ile Thr
        195                 200                 205

Asn Glu Ala Thr Leu Pro Lys Arg
    210                 215
```

<210> SEQ ID NO 6
<211> LENGTH: 648
<212> TYPE: DNA
<213> ORGANISM: Escherichia coli

<400> SEQUENCE: 6

```
gttcaaccgg aaatcgttcc ggttggtgcg accatcgacg acacgctgcc gattacagtc     60
gaagcgccgg aagcctgccc gcgttatctt ggccgtgtgg taaaaggcat taacgttaaa    120
gcgccaactc cgctgtggat gaaagaaaaa ctgcgtcgtt gcgggatccg ttctatcgat    180
gcagttgttg acgtcaccaa ctatgtgctg ctcgaactgg gccagccgat gcacgctttc    240
gataaagatc gcattgaagg cggcattgtg gtgcggatgg cgaaagaggg cgaaacgctg    300
gtgctgctcg acggtactga agcgaagctg aatgctgaca ctctggtcat cgccgaccac    360
```

-continued

```
aacaaggcgc tggcgatggg cggcatcttc ggtggcgaac actctggcgt gaatgacgaa    420
acacaaaacg tgctgctgga atgcgcgttc tttagcccgc tgtctatcac cggtcgtgct    480
cgtcgtcatg gcctgcatac cgatgcgtct caccgttatg agcgtggcgt tgatccggca    540
ctgcagcaca aagcgatgga acgtgcgacc cgtctgctga tcgacatctg cggtggtgag    600
gctggcccgg taattgatat caccaacgaa gcaacgctgc cgaagcgt               648
```

<210> SEQ ID NO 7
<211> LENGTH: 582
<212> TYPE: DNA
<213> ORGANISM: Pyrococcus horikoshii

<400> SEQUENCE: 7

```
gaggttaaaa agagtaacgt aacggtttac gttgatgaaa agcttaaaga tataaggcct     60
tatggagttt acgcaatagt tgaaggttta aggctcgacg aagattcttt aagtcaaatg    120
attcagctac aagaaaagat agcccttaca tttggaagaa gaaggagaga gtggccata    180 ggaatcttcg atttttgataa gattaagcca cctatttact ataaagccgc cgaaaaaact    240
gaaaagtttg ccccctggg ctataaagag gaaatgactc tagaggagat ccttgaaaag    300
catgaaaagg gaagggagta tgggcacctt ataaaggata aacaatttta tccactactt    360
attgacagcg aggggaatgt gctctccatg ccgccaataa tcaactccga gtttacggga    420
agagtaacaa cggatacgaa aaatgtcttc atagatgtca cgggatggaa gcttgagaag    480
gtaatgcttg cccttaatgt catggtaact gcattagcag agcgtggagg taaaataagg    540
agcgttaggg ttgtctacaa ggacttcgaa attgaaaccc ca                     582
```

<210> SEQ ID NO 8
<211> LENGTH: 405
<212> TYPE: PRT
<213> ORGANISM: Thermus thermophilus

<400> SEQUENCE: 8

```
Met Arg Val Pro Phe Ser Trp Leu Lys Ala Tyr Val Pro Glu Leu Glu
  1               5                  10                  15

Ser Pro Glu Val Leu Glu Glu Arg Leu Ala Gly Leu Gly Phe Glu Thr
             20                  25                  30

Asp Arg Ile Glu Arg Val Phe Pro Ile Pro Arg Gly Val Val Phe Ala
         35                  40                  45

Arg Val Leu Glu Ala His Pro Ile Pro Gly Thr Arg Leu Lys Arg Leu
     50                  55                  60

Val Leu Asp Ala Gly Arg Thr Val Glu Val Val Ser Gly Ala Glu Asn
 65                  70                  75                  80

Ala Arg Lys Gly Ile Gly Val Ala Leu Ala Leu Pro Gly Thr Glu Leu
                 85                  90                  95

Pro Gly Leu Gly Gln Lys Val Gly Glu Arg Val Ile Gln Gly Val Arg
            100                 105                 110

Ser Phe Gly Met Ala Leu Ser Pro Arg Glu Leu Gly Val Gly Glu Tyr
        115                 120                 125

Gly Gly Gly Leu Leu Glu Phe Pro Glu Asp Ala Leu Pro Pro Gly Thr
    130                 135                 140

Pro Leu Ser Glu Ala Trp Pro Glu Glu Val Val Leu Asp Leu Glu Val
145                 150                 155                 160

Thr Pro Asn Arg Pro Asp Ala Leu Gly Leu Leu Gly Leu Ala Arg Asp
                165                 170                 175

Leu His Ala Leu Gly Tyr Ala Leu Val Glu Pro Glu Ala Ala Leu Lys
```

```
                    180               185               190
Ala Glu Ala Leu Pro Leu Pro Phe Ala Leu Lys Val Glu Asp Pro Glu
                195               200               205

Gly Ala Pro His Phe Thr Leu Gly Tyr Ala Phe Gly Leu Arg Val Ala
            210               215               220

Pro Ser Pro Leu Trp Met Gln Arg Ala Leu Phe Ala Ala Gly Met Arg
225               230               235               240

Pro Ile Asn Asn Val Val Asp Val Thr Asn Tyr Val Met Leu Glu Arg
                245               250               255

Ala Gln Pro Met His Ala Phe Asp Leu Arg Phe Val Gly Glu Gly Ile
            260               265               270

Ala Val Arg Arg Ala Arg Glu Gly Glu Arg Leu Lys Thr Leu Asp Gly
            275               280               285

Val Glu Arg Thr Leu His Pro Glu Asp Leu Val Ile Ala Gly Trp Arg
        290               295               300

Gly Glu Glu Ser Phe Pro Leu Gly Leu Ala Gly Val Met Gly Gly Ala
305               310               315               320

Glu Ser Glu Val Arg Glu Asp Thr Glu Ala Ile Ala Leu Glu Val Ala
                325               330               335

Cys Phe Asp Pro Val Ser Ile Arg Lys Thr Ala Arg Arg His Gly Leu
            340               345               350

Arg Thr Glu Ala Ser His Arg Phe Glu Arg Gly Val Asp Pro Leu Gly
            355               360               365

Gln Val Pro Ala Gln Arg Arg Ala Leu Ser Leu Leu Gln Ala Leu Ala
        370               375               380

Gly Ala Arg Val Ala Glu Ala Leu Leu Glu Ala Gly Ser Pro Lys Pro
385               390               395               400

Pro Glu Ala Ile Pro
                405

<210> SEQ ID NO 9
<211> LENGTH: 1215
<212> TYPE: DNA
<213> ORGANISM: Thermus thermophilus

<400> SEQUENCE: 9
atgagggtgc ccttctcctg gctaaaagcc tacgtgcccg agctggaaag ccccgaggtc      60
ctggaggagc gcctggcggg cctggggttt gaaacggacc ggatagagcg gtcttccccc     120
atcccaagag gggtggtctt cgcccgggtc ctggaggccc accccatccc ggcacccgg     180 cttaagcgcc tggtcctgga cgcgggccgg acggtggaag tggtctcggg ggcggaaaac     240
gcccgaaaag gaatcggggt ggccctggcc ctccccggga cggagcttcc cggcctgggc     300
caaaaggtgg ggaacgggt  catccaaggg gtgcggtcct tcggcatggc cctctctccc     360
cgggagctcg ggtagggga  gtacggcggg gggcttctgg agttccccga ggacgccctc     420
ccccccggca cccccctttc ggaggcctgg ccggaggagg tggtgctgga cctcgaggtc     480
accccgaacc gccggacgc  cctgggcctt ttgggcctcg cccgggacct ccacgccctg     540
ggctacgccc tggtggagcc cgaagcggcc ctgaaggcgg aggcccttcc cctcccttc     600 gccctcaagg tggaggaccc ggagggcgcc cccacttca  ccctgggcta cgccttcggc     660
ctaagggtgg ccccaagccc cctctggatg cagcgggccc tcttcgccgc gggcatgcgg     720
cccatcaaca acgtcgtgga cgtgaccaac tacgtcatgc tggaaagggc ccagcccatg     780
cacgcctttg acctgcgctt cgtaggagag gggatcgcgg tgcgccgggc gcgggaaggg     840
```

| | |
|---|---:|
| gagcggctta agaccctgga cggggtggaa agaaccctcc accccgagga cctggtgatc | 900 |
| gccgggtggc ggggggagga gagcttcccc ttgggcctcg ccggggtcat gggcggggcg | 960 |
| gagagcgagg tccgggagga cacggaggcc atcgccttgg aggtggcctg ctttgacccg | 1020 |
| gtctccatcc gcaagaccgc ccgccgccac ggcctgcgca ccgaggcgag ccaccgcttt | 1080 |
| gagcgggggg tggacccccct gggccaggtc cccgcccaga ggcgggcctt aagcctcctc | 1140 |
| caggccctgg cggggggccg ggtggccgag ccctcctcg aggcgggaag ccccaagccc | 1200 |
| ccggaggcca tcccc | 1215 |

<210> SEQ ID NO 10
<211> LENGTH: 1926
<212> TYPE: DNA
<213> ORGANISM: Escherichia coli

<400> SEQUENCE: 10

| | |
|---|---:|
| atggttcaac cggaaatcgt tccggttggt gcgaccatcg acgacacgct gccgattaca | 60 |
| gtcgaagcgc cggaagcctg cccgcgttat cttggccgtg tggtaaaagg cattaacgtt | 120 |
| aaagcgccaa ctccgctgtg gatgaaagaa aaactgcgtc gttgcgggat ccgttctatc | 180 |
| gatgcagttg ttgacgtcac caactatgtg ctgctcgaac tgggccagcc gatgcacgct | 240 |
| ttcgataaag atcgcattga aggcggcatt gtggtgcgga tggcgaaaga gggcgaaacg | 300 |
| ctggtgctgc tcgacggtac tgaagcgaag ctgaatgctg acactctggt catcgccgac | 360 |
| cacaacaagg cgctggcgat gggcggcatc ttcggtggcg aacactctgg cgtgaatgac | 420 |
| gaaacacaaa acgtgctgct ggaatgcgcg ttctttagcc cgctgtctat caccggtcgt | 480 |
| gctcgtcgtc atggcctgca taccgatgcg tctcaccgtt atgagcgtgg cgttgatccg | 540 |
| gcactgcagc acaaagcgat ggaacgtgcg acccgtctgc tgatcgacat ctgcggtggt | 600 |
| gaggctggcc cggtaattga tatcaccaac gaagcaacgc tgccgaagcg tatggcaagc | 660 |
| agtaacttga ttaaacaatt gcaagagcgg gggctggtag cccaggtgac ggacgaggaa | 720 |
| gcgttagcag agcgactggc gcaaggcccc atcgcgctcg tttgcggctt cgatcctacc | 780 |
| gctgacagct tgcatttggg gcatcttgtt ccattgttat gcctgaaacg cttccagcag | 840 |
| gcgggccaca gccggttgc gctggtaggc ggcgcgacgg tctgattgg cgacccgagc | 900 |
| ttcaaagctg ccgagcgtaa gctgaacacc gaagaaactg ttcaggagtg ggtggacaaa | 960 |
| atccgtaagc aggttgcccc gttcctcgat ttcgactgtg agaaaactc tgctatcgcg | 1020 |
| gcgaacaact atgactggtt cggcaatatg aatgtgctga ccttcctgcg cgatattggc | 1080 |
| aaacacttct ccgttaacca tgatcaac aagaagcgg ttaagcagcg tctcaaccgt | 1140 |
| gaagatcagg ggatttcgtt cactgagttt cctacaacc tgttgcaggg ttatgacttc | 1200 |
| gcctgtctga caaacagta cggtgtggtg ctgtgcattg gtggttctga ccagtggggt | 1260 |
| aacatcactt ctggtatcga cctgacccgt cgtctgcatc agaatcaggt gtttggcctg | 1320 |
| accgttccgc tgatcactaa agcagatggc accaaatttg gtaaaactga aggcggcgca | 1380 |
| gtctggttgg atccgaagaa aaccagcccg tacaaattct accagttctg gatcaacact | 1440 |
| gcggatgccg acgtttaccg cttcctgaag ttcttcacct ttatgagcat tgaagagatc | 1500 |
| aacgccctgg aagaagaaga taaaaacagc ggtaaagcac cgcgcgccca gtatgtactg | 1560 |
| gcggagcagg tgactcgtct ggttcacggt gaagaaggtt acaggcggc aaaacgtatt | 1620 |
| accgaatgcc tgttcagcgg ttctttgagt gcgctgagtg aagcggactt cgaacagctg | 1680 |
| gcgcaggacg gcgtaccgat ggttgagatg gaaaaggggcg cagacctgat gcaggcactg | 1740 |

-continued

| | |
|---|---|
| gtcgattctg aactgcaacc ttcccgtggt caggcacgta aaactatcgc ctccaatgcc | 1800 |
| atcaccatta acggtgaaaa acagtccgat cctgaatact tctttaaaga agaagatcgt | 1860 |
| ctgtttggtc gttttacctt actgcgtcgc ggtaaaaaga attactgtct gatttgctgg | 1920 |
| aaataa | 1926 |

<210> SEQ ID NO 11
<211> LENGTH: 2508
<212> TYPE: DNA
<213> ORGANISM: Artificial Sequence
<220> FEATURE:
<223> OTHER INFORMATION: Description of Artificial Sequence:Ted-N-IYRS

<400> SEQUENCE: 11

| | |
|---|---|
| atgagggtgc ccttctcctg gctaaaagcc tacgtgcccg agctggaaag ccccgaggtc | 60 |
| ctggaggagc gcctggcggg cctggggttt gaaacggacc ggatagagcg ggtcttcccc | 120 |
| atcccaagag gggtggtctt cgcccgggtc ctggaggccc accccatccc ggcacccgg | 180 |
| cttaagcgcc tggtcctgga cgcgggccgg acggtggaag tggtctcggg ggcggaaaac | 240 |
| gcccgaaaag gaatcggggt ggccctggcc ctccccggga cggagcttcc cggcctgggc | 300 |
| caaaaggtgg gggaacgggt catccaaggg gtgcggtcct tcggcatggc cctctctccc | 360 |
| cgggagctcg gggtagggga gtacggcggg gggcttctgg agttccccga ggacgccctc | 420 |
| ccccccggca cccccctttc ggaggcctgg ccggaggagg tggtgctgga cctcgaggtc | 480 |
| accccgaacc gccggacgc cctgggcctt ttgggcctcg cccgggacct ccacgccctg | 540 |
| ggctacgccc tggtggagcc cgaagcggcc ctgaaggcgg aggcccttcc cctcccttc | 600 |
| gccctcaagg tggaggaccc ggagggcgcc ccccacttca ccctgggcta cgccttcggc | 660 |
| ctaagggtgg ccccaagccc cctctggatg cagcgggccc tcttcgccgc gggcatgcgg | 720 |
| cccatcaaca acgtcgtgga cgtgaccaac tacgtcatgc tggaaagggc ccagcccatg | 780 |
| cacgcctttg acctgcgctt cgtaggagag gggatcgcgg tgcgccgggc gcgggaaggg | 840 |
| gagcggctta agaccctgga cggggtggaa agaaccctcc accccgagga cctggtgatc | 900 |
| gccgggtggc gggggagga gagcttcccc ttgggcctcg ccgggtcat gggcggggcg | 960 |
| gagagcgagg tccgggagga cacggaggcc atcgccttgg aggtggcctg ctttgacccg | 1020 |
| gtctccatcc gcaagaccgc ccgccgccac ggcctgcgca ccgaggcgag ccaccgcttt | 1080 |
| gagcgggggg tggacccct gggccaggtc cccgcccaga ggcgggcctt aagcctcctc | 1140 |
| caggccctgg cggggcccg ggtggccgag ccctcctcg aggcgggaag ccccaagccc | 1200 |
| ccggaggcca tccccggcag cgcgccgagc ggcatggcaa gcagtaactt gattaaacaa | 1260 |
| ttgcaagagc gggggctggt agcccaggtg acggacgagg aagcgttagc agagcgactg | 1320 |
| gcgcaaggcc cgatcgcgct cgtttgcggc ttcgatccta ccgctgacag cttgcatttg | 1380 |
| gggcatcttg ttccattgtt atgcctgaaa cgcttccagc aggcgggcca caagccggtt | 1440 |
| gcgctggtag gcggcgcgac gggtctgatt ggcgacccga gcttcaaagc tgccgagcgt | 1500 |
| aagctgaaca ccgaagaaac tgttcaggag tgggtgaca aaatccgtaa gcaggttgcc | 1560 |
| ccgttcctcg atttcgactg tggagaaaac tctgctatcg cggcgaacaa ctatgactgg | 1620 |
| ttcggcaata tgaatgtgct gaccttcctg cgcgatattg caaacacttc tccgttaac | 1680 |
| cagatgatca acaaagaagc ggttaagcag cgtctcaacc gtgaagatca ggggatttcg | 1740 |
| ttcactgagt tttcctacaa cctgttgcag ggttatgact cgcctgtct gaacaaacag | 1800 |
| tacggtgtgg tgctgtgcat tggtggttct gaccagtggg gtaacatcac ttctggtatc | 1860 |

```
gacctgaccc gtcgtctgca tcagaatcag gtgtttggcc tgaccgttcc gctgatcact      1920
aaagcagatg gcaccaaatt tggtaaaact gaaggcggcg cagtctggtt ggatccgaag      1980
aaaaccagcc cgtacaaatt ctaccagttc tggatcaaca ctgcggatgc cgacgtttac      2040
cgcttcctga agttcttcac ctttatgagc attgaagaga tcaacgccct ggaagaagaa      2100
gataaaaaca gcggtaaagc accgcgcgcc cagtatgtac tggcggagca ggtgactcgt      2160
ctggttcacg gtgaagaagg tttacaggcg gcaaaacgta ttaccgaatg cctgttcagc      2220
ggttctttga gtgcgctgag tgaagcggac ttcgaacagc tggcgcagga cggcgtaccg      2280
atggttgaga tggaaaaggg cgcagacctg atgcaggcac tggtcgattc tgaactgcaa      2340
ccttcccgtg gtcaggcacg taaaactatc gcctccaatg ccatcaccat taacggtgaa      2400
aaacagtccg atcctgaata cttctttaaa gaagaagatc gtctgtttgg tcgttttacc      2460
ttactgcgtc gcggtaaaaa gaattactgt ctgatttgct ggaaataa                   2508
```

<210> SEQ ID NO 12
<211> LENGTH: 1890
<212> TYPE: DNA
<213> ORGANISM: Artificial Sequence
<220> FEATURE:
<223> OTHER INFORMATION: Description of Artificial Sequence:Ped-N-IYRS

<400> SEQUENCE: 12

```
atggaggtta aaagagtaa cgtaacggtt tacgttgatg aaaagcttaa agatataagg        60
ccttatggag tttacgcaat agttgaaggt ttaaggctcg acgaagattc tttaagtcaa      120
atgattcagc tacaagaaaa gatagcccct acatttggaa gaagaaggag agaagtggcc      180
ataggaatct tcgattttga taagattaag ccacctattt actataaagc cgccgaaaaa      240
actgaaaagt ttgccccccct gggctataaa gaggaaatga ctctagagga gatccttgaa      300
aagcatgaaa agggaaggga gtatgggcac cttataaagg ataaacaatt ttatccacta      360
cttattgaca gcgagggaa tgtgctctcc atgccgccaa taatcaactc cgagtttacg      420
ggaagagtaa caacggatac gaaaaatgtc ttcatagatg tcacgggatg gaagcttgag      480
aaggtaatgc ttgcccttaa tgtcatggta actgcattag cagagcgtgg aggtaaaata      540
aggagcgtta gggttgtcta caaggacttc gaaattgaaa ccccaggctc cgcctccggc      600
cccgcctccg ccggcatggc aagcagtaac ttgattaaac aattgcaaga gcggggggctg      660 gtagcccagg tgacggacga ggaagcgtta gcagagcgac tggcgcaagg cccgatcgcg      720
ctcgtttgcg gcttcgatcc taccgctgac agcttgcatt gggggcatct tgttccattg      780
ttatgcctga aacgcttcca gcaggcgggc cacaagccgg ttgcgctggt aggcggcgcg      840
acgggtctga ttggcgaccc gagcttcaaa gctgccgagc gtaagctgaa caccgaagaa      900
actgttcagg agtgggtgga caaaatccgt aagcaggttg ccccgttcct cgatttcgac      960
tgtggagaaa actctgctat cgcggcgaac aactatgact ggttcggcaa tatgaatgtg     1020
ctgaccttcc tgcgcgatat tggcaaacac ttctccgtta accagatgat caacaaagaa     1080
gcggttaagc agcgtctcaa ccgtgaagat caggggattt cgttcactga gttttcctac     1140
aacctgttgc agggttatga cttcgcctgt ctgaacaaac agtacggtgt ggtgctgtgc     1200
attggtggtt ctgaccagtg gggtaacatc acttctggta tcgacctgac ccgtcgtctg     1260
catcagaatc aggtgtttgg cctgaccgtt ccgctgatca ctaaagcaga tggcaccaaa     1320
tttggtaaaa ctgaaggcgg cgcagtctgg ttggatccga agaaaaccag cccgtacaaa     1380
ttctaccagt tctggatcaa cactgcggat gccgacgttt accgcttcct gaagttcttc     1440
```

| acctttatga | gcattgaaga | gatcaacgcc | ctggaagaag | aagataaaaa | cagcggtaaa | 1500 |
| gcaccgcgcg | cccagtatgt | actggcggag | caggtgactc | gtctggttca | cggtgaagaa | 1560 |
| ggtttacagg | cggcaaaacg | tattaccgaa | tgcctgttca | gcggttcttt | gagtgcgctg | 1620 |
| agtgaagcga | cttcgaaca | gctggcgcag | gacggcgtac | cgatggttga | gatggaaaag | 1680 |
| ggcgcagacc | tgatgcaggc | actggtcgat | tctgaactgc | aaccttcccg | tggtcaggca | 1740 |
| cgtaaaacta | tcgcctccaa | tgccatcacc | attaacggtg | aaaaacagtc | cgatcctgaa | 1800 |
| tacttcttta | aagaagaaga | tcgtctgttt | ggtcgtttta | ccttactgcg | tcgcggtaaa | 1860 |
| aagaattact | gtctgatttg | ctggaaataa | | | | 1890 |

<210> SEQ ID NO 13
<211> LENGTH: 1884
<212> TYPE: DNA
<213> ORGANISM: Artificial Sequence
<220> FEATURE:
<223> OTHER INFORMATION: Description of Artificial Sequence:Ped-CP1-IYRS

<400> SEQUENCE: 13

| atggcaagca | gtaacttgat | taaacaattg | caagagcggg | ggctggtagc | ccaggtgacg | 60 |
| gacgaggaag | cgttagcaga | gcgactggcg | caaggcccga | tcgcgctcgt | ttgcggcttc | 120 |
| gatcctaccg | ctgacagctt | gcatttgggg | catcttgttc | cattgttatg | cctgaaacgc | 180 |
| ttccagcagg | cgggccacaa | gccggttgcg | ctggtaggcg | gcgcgacggg | tctgattggc | 240 |
| gacccgagct | tcaaagctgc | cgagcgtaag | ctgaacaccg | aagaaactgt | tcaggagtgg | 300 |
| gtggacaaaa | tccgtaagca | ggttgccccg | ttcctcgatt | tcgactgtgg | agaaaactct | 360 |
| gctatcgcgg | cgaacaacta | tgactggttc | ggcaatatga | atgtgctgac | cttcctgcgc | 420 |
| gatattggca | aacacttctc | cgttaaccag | atgatcaaca | agaagcggt | taagcagcgt | 480 |
| ctcaaccgtg | aagatcagga | ggttaaaaag | agtaacgtaa | cggtttacgt | tgatgaaaag | 540 |
| cttaaagata | taaggcctta | tggagtttac | gcaatagttg | aaggtttaag | gctcgacgaa | 600 |
| gattctttaa | gtcaaatgat | tcagctacaa | gaaaagatag | cccttacatt | tggaagaaga | 660 |
| aggagagaag | tggccatagg | aatcttcgat | tttgataaga | ttaagccacc | tatttactat | 720 |
| aaagccgccg | aaaaaactga | aaagtttgcc | cccctgggct | ataaagagga | aatgactcta | 780 |
| gaggagatcc | ttgaaaagca | tgaaaaggga | agggagtatg | gcacccttat | aaaggataaa | 840 |
| caattttatc | cactacttat | tgacagcgag | gggaatgtgc | tctccatgcc | gccaataatc | 900 |
| aactccgagt | ttacgggaag | agtaacaacg | gatacgaaaa | atgtcttcat | agatgtcacg | 960 |
| ggatggaagc | ttgagaaggt | aatgcttgcc | cttaatgtca | tggtaactgc | attagcagag | 1020 |
| cgtgaggta | aaataaggag | cgttagggtt | gtctacaagg | acttcgaaat | tgaaccccca | 1080 |
| ggctccgcct | ccggccccgc | ctccgccggg | atttcgttca | ctgagttttc | ctacaacctg | 1140 |
| ttgcagggtt | atgacttcgc | ctgtctgaac | aaacagtacg | gtgtggtgct | gtgcattggt | 1200 |
| ggttctgacc | agtggggtaa | catcacttct | ggtatcgacc | tgacccgtcg | tctgcatcag | 1260 |
| aatcaggtgt | ttggcctgac | cgttccgctg | atcactaaag | cagatggcac | caaatttggt | 1320 |
| aaaactgaag | cggcgcagt | ctggttggat | ccgaagaaaa | ccagcccgta | caaattctac | 1380 |
| cagttctgga | tcaacactgc | ggatgccgac | gtttaccgct | tcctgaagtt | cttcacctt | 1440 |
| atgagcattg | aagagatcaa | cgccctggaa | gaagaagata | aaaacagcgg | taaagcaccg | 1500 |
| cgcgcccagt | atgtactggc | ggagcaggtg | actcgtctgg | ttcacggtga | agaaggttta | 1560 |
| caggcggcaa | aacgtattac | cgaatgcctg | ttcagcggtt | ctttgagtgc | gctgagtgaa | 1620 |

```
gcggacttcg aacagctggc gcaggacggc gtaccgatgg ttgagatgga aaagggcgca    1680
gacctgatgc aggcactggt cgattctgaa ctgcaacctt cccgtggtca ggcacgtaaa    1740
actatcgcct ccaatgccat caccattaac ggtgaaaaac agtccgatcc tgaatacttc    1800
tttaaagaag aagatcgtct gtttggtcgt tttaccttac tgcgtcgcgg taaaaagaat    1860
tactgtctga tttgctggaa ataa                                          1884
```

<210> SEQ ID NO 14
<211> LENGTH: 1914
<212> TYPE: DNA
<213> ORGANISM: Artificial Sequence
<220> FEATURE:
<223> OTHER INFORMATION: Description of Artificial Sequence:Ped-AC-IYRS

<400> SEQUENCE: 14

```
atggcaagca gtaacttgat taaacaattg caagagcggg ggctggtagc ccaggtgacg     60
gacgaggaag cgttagcaga gcgactggcg caaggcccga tcgcgctcgt ttgcggcttc    120
gatcctaccg ctgacagctt gcatttgggg catcttgttc cattgttatg cctgaaacgc    180
ttccagcagg cgggccacaa gccgttgcgc tggtaggcg gcgcgacggg tctgattggc    240
gacccgagct tcaaagctgc cgagcgtaag ctgaacaccg aagaaactgt tcaggagtgg    300
gtggacaaaa tccgtaagca ggttgccccg ttcctcgatt tcgactgtgg agaaaactct    360
gctatcgcgg cgaacaacta tgactggttc ggcaatatga atgtgctgac cttcctgcgc    420
gatattggca acacttctc cgttaaccag atgatcaaca agaagcggt taagcagcgt    480 ctcaaccgtg aagatcaggg gatttcgttc actgagtttt cctacaacct gttgcagggt    540
tatgacttcg cctgtctgaa caaacagtac ggtgtggtgc tgtgcattgg tggttctgac    600
cagtggggta acatcacttc tggtatcgac ctgacccgtc gtctgcatca gatcaggtg    660 tttggcctga ccgttccgct gatcactaaa gcagatggca ccaaatttgg taaaactgaa    720
ggcggcgcag tctggttgga tccgaagaaa accagcccgt acaaattcta ccagttctgg    780
atcaacactg cggatgccga cgtttaccgc ttcctgaagt tcttcacctt tatgagcatt    840
gaagagatca acgccctgga agaagaagat aaaaacagcg gtaaagcacc gcgcgcccag    900
tatgtactgg cggaggttaa aagagtaac gtaacggttt acgttgatga aaagcttaaa    960
gatataaggc cttatggagt ttacgcaata gttgaaggtt taaggctcga cgaagattct    1020
ttaagtcaaa tgattcagct acaagaaaag atagccctta catttggaag aagaaggaga    1080
gaagtggcca taggaatctt cgattttgat aagattaagc cacctatttta ctataaagcc    1140 gccgaaaaaa ctgaaaagtt tgccccctg gctataaag aggaaatgac tctagaggag    1200
atccttgaaa agcatgaaaa gggaaggag tatgggcacc ttataaagga taaacaattt    1260
tatccactac ttattgacag cgaggggaat gtgctctcca tgccgccaat aatcaactcc    1320
gagtttacgg gaagagtaac aacgatacg aaaaatgtct tcatagatgt cacgggatgg    1380
aagcttgaga aggtaatgct tgcccttaat gtcatggtaa ctgcattagc agagcgtgga    1440
ggtaaaataa ggagcgttag ggttgtctac aaggacttcg aaattgaaac cccaggctcc    1500
gcctccggcc ccgcctccgc cggcgcaccg cgcgcccagt atgtactggc ggagcaggtg    1560
actcgtctgg ttcacggtga agaaggttta caggcggcaa aacgtattac cgaatgcctg    1620
ttcagcggtt cttttgagtgc gctgagtgaa gcggacttcg aacagctggc gcaggacggc    1680
gtaccgatgg ttgagatgga aaagggcgca gacctgatgc aggcactggt cgattctgaa    1740
ctgcaacctt cccgtggtca ggcacgtaaa actatcgcct ccaatgccat caccattaac    1800
```

```
ggtgaaaaac agtccgatcc tgaatacttc tttaaagaag aagatcgtct gtttggtcgt    1860
tttaccttac tgcgtcgcgg taaaaagaat tactgtctga tttgctggaa ataa          1914
```

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence:Primer EcN1

<400> SEQUENCE: 15

```
gcacgccata tggttcaacc ggaaatcgtt ccgg                                 34
```

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence:Primer EcN2

<400> SEQUENCE: 16

```
gttactgctt gccatacgct tcggcagcgt tgcttc                               36
```

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:Primer EcN3

<400> SEQUENCE: 17

```
gaagcaacgc tgccgaagcg tatggcaagc agtaac                               36
```

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence:Primer EcN4

<400> SEQUENCE: 18

```
aggtgcctcg agtttccagc aaatcagaca g                                    31
```

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:Primer EcN5

<400> SEQUENCE: 19

```
gcacgccata tggttcaacc ggaaatcgtt ccgg                                 34
```

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence:Primer EcN6

<400> SEQUENCE: 20

```
aggtgcctcg agtttccagc aaatcagaca g                                    31
```

<210> SEQ ID NO 21
<211> LENGTH: 37
<212> TYPE: DNA

<213> ORGANISM: Artificial Sequence
<220> FEATURE:
<223> OTHER INFORMATION: Description of Artificial Sequence:Primer TtN1

<400> SEQUENCE: 21
gccgcccata tgagggtgcc cttctcctgg ctaaaag        37

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence:Primer TtN2

<400> SEQUENCE: 22
caagttactg cttgccatgc cgctcggcgc gctgccgggg atggcctccg gggg        54

<210> SEQ ID NO 23
<211> LENGTH: 54
<212> TYPE: DNA
<213> ORGANISM: Artificial Sequence
<220> FEATURE:
<223> OTHER INFORMATION: Description of Artificial Sequence:Primer TtN3

<400> SEQUENCE: 23
cccccggagg ccatccccgg cagcgcgccg agcggcatgg caagcagtaa cttg        54

<210> SEQ ID NO 24
<211> LENGTH: 31
<212> TYPE: DNA
<213> ORGANISM: Artificial Sequence
<220> FEATURE:
<223> OTHER INFORMATION: Description of Artificial Sequence:Primer TtN4

<400> SEQUENCE: 24
aggtgcctcg agtttccagc aaatcagaca g        31

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence:Primer TtN5

<400> SEQUENCE: 25
gccgcccata tgagggtgcc cttctcctgg ctaaaag        37

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence:Primer TtN6

<400> SEQUENCE: 26
aggtgcctcg agtttccagc aaatcagaca g        31

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence:Primer PhN1

<400> SEQUENCE: 27
cccatatgga ggttaaaaag agtaacgtaa c        31

```
<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence:Primer PhN2

<400> SEQUENCE: 28
gttactgctt gccatgccgg cggaggcggg gccggaggcg agcctgggg tttcaatttc      60

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence:Primer PhN3

<400> SEQUENCE: 29
gaaattgaaa ccccaggctc cgcctccggc cccgcctccg ccggcatggc aagcagtaac    60

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence:Primer PhN4

<400> SEQUENCE: 30
aggtgcctcg agtttccagc aaatcagaca g                                   31

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence:Primer PhN5

<400> SEQUENCE: 31
cccatatgga ggttaaaaag agtaacgtaa c                                   31

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence:Primer PhN6

<400> SEQUENCE: 32
aggtgcctcg agtttccagc aaatcagaca g                                   31

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence:Primer PhC1

<400> SEQUENCE: 33
caaccgtgaa gatcaggagg ttaaaaagag                                     30

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence:Primer PhC2
```

-continued

<400> SEQUENCE: 34
cagtgaacga atcccggcg gaggcggggc c                            31

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence:Primer PhC3

<400> SEQUENCE: 35
cggcgccata tggcaagcag taacttgatt aaac                        34

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:Primer PhC4

<400> SEQUENCE: 36 ctcttttaa cctcctgatc ttcacggttg                              30

<210> SEQ ID NO 37
<211> LENGTH: 31
<212> TYPE: DNA
<213> ORGANISM: Artificial Sequence
<220> FEATURE:
<223> OTHER INFORMATION: Description of Artificial Sequence:Primer PhC5

<400> SEQUENCE: 37
ggccccgcct ccgccgggat ttcgttcact g                           31

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence:Primer PhC6

<400> SEQUENCE: 38
aggtgcctcg agtttccagc aaatcagaca g                           31

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence:Primer PhC7

<400> SEQUENCE: 39
cggcgccata tggcaagcag taacttgatt aaac                        34

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence:Primer PhC8

<400> SEQUENCE: 40
aggtgcctcg agtttccagc aaatcagaca g                           31

<210> SEQ ID NO 41
<211> LENGTH: 33
<212> TYPE: DNA

```
<213> ORGANISM: Artificial Sequence
<220> FEATURE:
<223> OTHER INFORMATION: Description of Artificial Sequence:Primer PhA1

<400> SEQUENCE: 41
cagtatgtac tggcggaggt taaaaagagt aac                                   33

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence:Primer PhA2

<400> SEQUENCE: 42
ctgggcgcgc ggtgcgccgg cggaggcggg                                      30

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence:Primer PhA3

<400> SEQUENCE: 43
cggcgccata tggcaagcag taacttgatt aaac                                 34

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence:Primer PhA4

<400> SEQUENCE: 44
gttactcttt ttaacctccg ccagtacata ctg                                  33

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence:Primer PhA5

<400> SEQUENCE: 45
cccgcctccg ccggcgcacc gcgcgcccag                                      30

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence:Primer PhA6

<400> SEQUENCE: 46
aggtgcctcg agtttccagc aaatcagaca g                                    31

<210> SEQ ID NO 47
<211> LENGTH: 34
<212> TYPE: DNA
<213> ORGANISM: Artificial Sequence
<220> FEATURE:
<223> OTHER INFORMATION: Description of Artificial Sequence:Primer PhA7

<400> SEQUENCE: 47
cggcgccata tggcaagcag taacttgatt aaac                                 34
```

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence:Primer PhA8

<400> SEQUENCE: 48
aggtgcctcg agtttccagc aaatcagaca g                                    31

<210> SEQ ID NO 49
<211> LENGTH: 738
<212> TYPE: DNA
<213> ORGANISM: Artificial Sequence
<220> FEATURE:
<223> OTHER INFORMATION: Description of Artificial Sequence:GST(Am)

<400> SEQUENCE: 49
atggctagca tgactggtgg acagcaaatg ggtcgggatc cgggtgcgaa ttctggtgta    60
actaagaact cttagagccc tatactaggt tattggaaaa ttaagggcct tgtgcaaccc   120
actcgacttc ttttggaata tcttgaagaa aaatatgaag agcatttgta tgagcgcgat   180
gaaggtgata atggcgaaa caaaaagttt gaattgggtt tggagttttcc caatcttcct   240 tattatattg atggtgatgt taaattaaca cagtctatgg ccatcatacg ttatatagct   300
gacaagcaca acatgttggg tggttgtcca aaagagcgtg cagagatttc aatgcttgaa   360
ggagcggttt tggatattag atacggtgtt tcgagaattg catatagtaa agactttgaa   420
actctcaaag ttgatttcct tagcaagcta cctgaaatgc tgaaaatgtt cgaagatcgt   480
ttatgtcata aaacatattt aaatggtgat catgtaaccc atcctgactt catgttgtat   540
gacgctcttg atgttgtttt atacatggac ccaatgtgcc tggatgcgtt cccaaaatta   600
gtttgtttta aaaacgtat tgaagctatc ccacaaattg ataagtactt gaaatccagc   660
aagtatatag catggccttt gcagggctgg caagccacgt ttggtggtgg cgaccatcct   720
ccaaaatcgg attaataa                                                 738

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence:linkerN

<400> SEQUENCE: 50

Gln Arg Leu Asn Arg Glu Asp Gln Glu Val Lys Lys Ser Asn Val
 1               5                  10                  15

<210> SEQ ID NO 51
<211> LENGTH: 22
<212> TYPE: PRT
<213> ORGANISM: Artificial Sequence
<220> FEATURE:
<223> OTHER INFORMATION: Description of Artificial Sequence:linkerC

<400> SEQUENCE: 51

Glu Ile Glu Thr Pro Gly Ser Ala Ser Gly Pro Ala Ser Ala Gly Ile
 1               5                  10                  15

Ser Phe Thr Phe Ser Tyr
            20

<210> SEQ ID NO 52
<211> LENGTH: 795

<212> TYPE: PRT
<213> ORGANISM: Escherichia coli

<400> SEQUENCE: 52

```
Met Lys Phe Ser Glu Leu Trp Leu Arg Glu Trp Val Asn Pro Ala Ile
 1               5                  10                  15

Asp Ser Asp Ala Leu Ala Asn Gln Ile Thr Met Ala Gly Leu Glu Val
                20                  25                  30

Asp Gly Val Glu Pro Val Ala Gly Ser Phe His Gly Val Val Val Gly
            35                  40                  45

Glu Val Val Glu Cys Ala Gln His Pro Asn Ala Asp Lys Leu Arg Val
 50                  55                  60

Thr Lys Val Asn Val Gly Gly Asp Arg Leu Leu Asp Ile Val Cys Gly
 65                  70                  75                  80

Ala Pro Asn Cys Arg Gln Gly Leu Arg Val Ala Val Ala Thr Ile Gly
                85                  90                  95

Ala Val Leu Pro Gly Asp Phe Lys Ile Lys Ala Lys Leu Arg Gly
            100                 105                 110

Glu Pro Ser Glu Gly Met Leu Cys Ser Phe Ser Glu Leu Gly Ile Ser
            115                 120                 125

Asp Asp His Ser Gly Ile Ile Glu Leu Pro Ala Asp Ala Pro Ile Gly
130                 135                 140

Thr Asp Ile Arg Glu Tyr Leu Lys Leu Asp Asp Asn Thr Ile Glu Ile
145                 150                 155                 160

Ser Val Thr Pro Asn Arg Ala Asp Cys Leu Gly Ile Ile Gly Val Ala
                165                 170                 175

Arg Asp Val Ala Val Leu Asn Gln Leu Pro Leu Val Gln Pro Glu Ile
            180                 185                 190

Val Pro Val Gly Ala Thr Ile Asp Asp Thr Leu Pro Ile Thr Val Glu
        195                 200                 205

Ala Pro Glu Ala Cys Pro Arg Tyr Leu Gly Arg Val Val Lys Gly Ile
210                 215                 220

Asn Val Lys Ala Pro Thr Pro Leu Trp Met Lys Glu Lys Leu Arg Arg
225                 230                 235                 240

Cys Gly Ile Arg Ser Ile Asp Ala Val Val Asp Val Thr Asn Tyr Val
                245                 250                 255

Leu Leu Glu Leu Gly Gln Pro Met His Ala Phe Asp Lys Asp Arg Ile
            260                 265                 270

Glu Gly Gly Ile Val Val Arg Met Ala Lys Glu Gly Glu Thr Leu Val
        275                 280                 285

Leu Leu Asp Gly Thr Glu Ala Lys Leu Asn Ala Asp Thr Leu Val Ile
        290                 295                 300

Ala Asp His Asn Lys Ala Leu Ala Met Gly Gly Ile Phe Gly Gly Glu
305                 310                 315                 320

His Ser Gly Val Asn Asp Glu Thr Gln Asn Val Leu Leu Glu Cys Ala
                325                 330                 335

Phe Phe Ser Pro Leu Ser Ile Thr Gly Arg Ala Arg His Gly Leu
            340                 345                 350

His Thr Asp Ala Ser His Arg Tyr Glu Arg Gly Val Asp Pro Ala Leu
        355                 360                 365

Gln His Lys Ala Met Glu Arg Ala Thr Arg Leu Leu Ile Asp Ile Cys
        370                 375                 380

Gly Gly Glu Ala Gly Pro Val Ile Asp Ile Thr Asn Glu Ala Thr Leu
385                 390                 395                 400
```

```
Pro Lys Arg Ala Thr Ile Thr Leu Arg Arg Ser Lys Leu Asp Arg Leu
                405                 410                 415

Ile Gly His His Ile Ala Asp Glu Gln Val Thr Asp Ile Leu Arg Arg
            420                 425                 430

Leu Gly Cys Glu Val Thr Glu Gly Lys Asp Glu Trp Gln Ala Val Ala
        435                 440                 445

Pro Ser Trp Arg Phe Asp Met Glu Ile Glu Glu Asp Leu Val Glu Glu
    450                 455                 460

Val Ala Arg Val Tyr Gly Tyr Asn Asn Ile Pro Asp Glu Pro Val Gln
465                 470                 475                 480

Ala Ser Leu Ile Met Gly Thr His Arg Glu Ala Asp Leu Ser Leu Lys
                485                 490                 495

Arg Val Lys Thr Leu Leu Asn Asp Lys Gly Tyr Gln Glu Val Ile Thr
            500                 505                 510

Tyr Ser Phe Val Asp Pro Lys Val Gln Gln Met Ile His Pro Gly Val
        515                 520                 525

Glu Ala Leu Leu Leu Pro Ser Pro Ile Ser Val Glu Met Ser Ala Met
    530                 535                 540

Arg Leu Ser Leu Trp Thr Gly Leu Leu Ala Thr Val Val Tyr Asn Gln
545                 550                 555                 560

Asn Arg Gln Gln Asn Arg Val Arg Ile Phe Glu Ser Gly Leu Arg Phe
                565                 570                 575

Val Pro Asp Thr Gln Ala Pro Leu Gly Ile Arg Gln Asp Leu Met Leu
            580                 585                 590

Ala Gly Val Ile Cys Gly Asn Arg Tyr Glu Glu His Trp Asn Leu Ala
        595                 600                 605

Lys Glu Thr Val Asp Phe Tyr Asp Leu Lys Gly Asp Leu Glu Ser Val
    610                 615                 620

Leu Asp Leu Thr Gly Lys Leu Asn Glu Val Glu Phe Arg Ala Glu Ala
625                 630                 635                 640

Asn Pro Ala Leu His Pro Gly Gln Ser Ala Ala Ile Tyr Leu Lys Gly
                645                 650                 655

Glu Arg Ile Gly Phe Val Gly Val Val His Pro Glu Leu Glu Arg Lys
            660                 665                 670

Leu Asp Leu Asn Gly Arg Thr Leu Val Phe Glu Leu Glu Trp Asn Lys
        675                 680                 685

Leu Ala Asp Arg Val Val Pro Gln Ala Arg Glu Ile Ser Arg Phe Pro
    690                 695                 700

Ala Asn Arg Arg Asp Ile Ala Val Val Ala Glu Asn Val Pro Ala
705                 710                 715                 720

Ala Asp Ile Leu Ser Glu Cys Lys Lys Val Gly Val Asn Gln Val Val
                725                 730                 735

Gly Val Asn Leu Phe Asp Val Tyr Arg Gly Lys Gly Val Ala Glu Gly
            740                 745                 750

Tyr Lys Ser Leu Ala Ile Ser Leu Ile Leu Gln Asp Thr Ser Arg Thr
        755                 760                 765

Leu Glu Glu Glu Glu Ile Ala Ala Thr Val Ala Lys Cys Val Glu Ala
    770                 775                 780

Leu Lys Glu Arg Phe Gln Ala Ser Leu Arg Asp
785                 790                 795

<210> SEQ ID NO 53
<211> LENGTH: 785
<212> TYPE: PRT
<213> ORGANISM: Thermus thermophilus
```

<400> SEQUENCE: 53

```
Met Arg Val Pro Phe Ser Trp Leu Lys Ala Tyr Val Pro Glu Leu Glu
  1               5                  10                  15
Ser Pro Glu Val Leu Glu Glu Arg Leu Ala Gly Leu Gly Phe Glu Thr
             20                  25                  30
Asp Arg Ile Glu Arg Val Phe Pro Ile Pro Arg Gly Val Val Phe Ala
         35                  40                  45
Arg Val Leu Glu Ala His Pro Ile Pro Gly Thr Arg Leu Lys Arg Leu
     50                  55                  60
Val Leu Asp Ala Gly Arg Thr Val Glu Val Ser Gly Ala Glu Asn
 65                  70                  75                  80
Ala Arg Lys Gly Ile Gly Val Ala Leu Ala Leu Pro Gly Thr Glu Leu
                 85                  90                  95
Pro Gly Leu Gly Gln Lys Val Gly Glu Arg Val Ile Gln Gly Val Arg
            100                 105                 110
Ser Phe Gly Met Ala Leu Ser Pro Arg Glu Leu Gly Val Gly Glu Tyr
        115                 120                 125
Gly Gly Gly Leu Leu Glu Phe Pro Glu Asp Ala Leu Pro Pro Gly Thr
    130                 135                 140
Pro Leu Ser Glu Ala Trp Pro Glu Val Val Leu Asp Leu Glu Val
145                 150                 155                 160
Thr Pro Asn Arg Pro Asp Ala Leu Gly Leu Leu Gly Leu Ala Arg Asp
                165                 170                 175
Leu His Ala Leu Gly Tyr Ala Leu Val Glu Pro Glu Ala Ala Leu Lys
            180                 185                 190
Ala Glu Ala Leu Pro Leu Pro Phe Ala Leu Lys Val Glu Asp Pro Glu
        195                 200                 205
Gly Ala Pro His Phe Thr Leu Gly Tyr Ala Phe Gly Leu Arg Val Ala
    210                 215                 220
Pro Ser Pro Leu Trp Met Gln Arg Ala Leu Phe Ala Ala Gly Met Arg
225                 230                 235                 240
Pro Ile Asn Asn Val Val Asp Val Thr Asn Tyr Val Met Leu Glu Arg
                245                 250                 255
Ala Gln Pro Met His Ala Phe Asp Leu Arg Phe Val Gly Glu Gly Ile
            260                 265                 270
Ala Val Arg Arg Ala Arg Glu Gly Glu Arg Leu Lys Thr Leu Asp Gly
        275                 280                 285
Val Glu Arg Thr Leu His Pro Glu Asp Leu Val Ile Ala Gly Trp Arg
    290                 295                 300
Gly Glu Glu Ser Phe Pro Leu Gly Leu Ala Gly Val Met Gly Gly Ala
305                 310                 315                 320
Glu Ser Glu Val Arg Glu Asp Thr Glu Ala Ile Ala Leu Glu Val Ala
                325                 330                 335
Cys Phe Asp Pro Val Ser Ile Arg Lys Thr Ala Arg Arg His Gly Leu
            340                 345                 350
Arg Thr Glu Ala Ser His Arg Phe Glu Arg Gly Val Asp Pro Leu Gly
        355                 360                 365
Gln Val Pro Ala Gln Arg Arg Ala Leu Ser Leu Leu Gln Ala Leu Ala
    370                 375                 380
Gly Ala Arg Val Ala Glu Ala Leu Leu Glu Ala Gly Ser Pro Lys Pro
385                 390                 395                 400
Pro Glu Ala Ile Pro Phe Arg Pro Glu Tyr Ala Asn Arg Leu Leu Gly
                405                 410                 415
```

```
Thr Ser Tyr Pro Glu Ala Glu Gln Ile Ala Ile Leu Lys Arg Leu Gly
            420                 425                 430

Cys Arg Val Glu Gly Glu Gly Pro Thr Tyr Arg Val Thr Pro Pro Ser
        435                 440                 445

His Arg Leu Asp Leu Arg Leu Glu Glu Asp Leu Val Glu Glu Val Ala
450                 455                 460

Arg Ile Gln Gly Tyr Glu Thr Ile Pro Leu Ala Leu Pro Ala Phe Phe
465                 470                 475                 480

Pro Ala Pro Asp Asn Arg Gly Val Glu Ala Pro Tyr Arg Lys Glu Gln
                485                 490                 495

Arg Leu Arg Glu Val Leu Ser Gly Leu Gly Phe Gln Glu Val Tyr Thr
            500                 505                 510

Tyr Ser Phe Met Asp Pro Glu Asp Ala Arg Arg Phe Arg Leu Asp Pro
        515                 520                 525

Pro Arg Leu Leu Leu Leu Asn Pro Leu Ala Pro Glu Lys Ala Ala Leu
530                 535                 540

Arg Thr His Leu Phe Pro Gly Leu Val Arg Val Leu Lys Glu Asn Leu
545                 550                 555                 560

Asp Leu Asp Arg Pro Glu Arg Ala Leu Leu Phe Glu Val Gly Arg Val
                565                 570                 575

Phe Arg Glu Arg Glu Thr His Leu Ala Gly Leu Leu Phe Gly Glu
            580                 585                 590

Gly Val Gly Leu Pro Trp Ala Lys Glu Arg Leu Ser Gly Tyr Phe Leu
        595                 600                 605

Leu Lys Gly Tyr Leu Glu Ala Leu Phe Ala Arg Leu Gly Leu Ala Phe
610                 615                 620

Arg Val Glu Ala Gln Ala Phe Pro Phe Leu His Pro Gly Val Ser Gly
625                 630                 635                 640

Arg Val Leu Val Glu Gly Glu Val Gly Phe Leu Gly Ala Leu His
                645                 650                 655

Pro Glu Ile Ala Gln Glu Leu Glu Leu Pro Pro Val His Leu Phe Glu
            660                 665                 670

Leu Arg Leu Pro Leu Pro Asp Lys Pro Leu Ala Phe Gln Asp Pro Ser
        675                 680                 685

Arg His Pro Ala Ala Phe Arg Asp Leu Ala Val Val Val Pro Ala Pro
690                 695                 700

Thr Pro Tyr Gly Glu Val Glu Ala Leu Val Arg Glu Ala Ala Gly Pro
705                 710                 715                 720

Tyr Leu Glu Ser Leu Ala Leu Phe Asp Leu Tyr Gln Gly Pro Pro Leu
                725                 730                 735

Pro Glu Gly His Lys Ser Leu Ala Phe His Leu Arg Phe Arg His Pro
            740                 745                 750

Lys Arg Thr Leu Arg Asp Glu Glu Val Glu Glu Ala Val Ser Arg Val
        755                 760                 765

Ala Glu Ala Leu Arg Ala Arg Gly Phe Gly Leu Arg Gly Leu Asp Thr
770                 775                 780

Pro
785

<210> SEQ ID NO 54
<211> LENGTH: 556
<212> TYPE: PRT
<213> ORGANISM: Pyrococcus horikoshii

<400> SEQUENCE: 54
```

```
Met Pro Lys Phe Asp Val Ser Lys Ser Asp Leu Glu Arg Leu Ile Gly
  1               5                  10                  15
Arg Ser Phe Ser Ile Glu Glu Trp Glu Asp Leu Val Leu Tyr Ala Lys
                 20                  25                  30
Cys Glu Leu Asp Asp Val Trp Glu Asn Gly Lys Val Tyr Phe Lys
                 35                  40                  45
Leu Asp Ser Lys Asp Thr Asn Arg Pro Asp Leu Trp Ser Ala Glu Gly
         50                  55                  60
Val Ala Arg Gln Ile Lys Trp Ala Leu Gly Ile Glu Lys Gly Leu Pro
 65                  70                  75                  80
Lys Tyr Glu Val Lys Lys Ser Asn Val Thr Val Tyr Val Asp Glu Lys
                     85                  90                  95
Leu Lys Asp Ile Arg Pro Tyr Gly Val Tyr Ala Ile Val Glu Gly Leu
                100                 105                 110
Arg Leu Asp Glu Asp Ser Leu Ser Gln Met Ile Gln Leu Gln Glu Lys
                115                 120                 125
Ile Ala Leu Thr Phe Gly Arg Arg Arg Glu Val Ala Ile Gly Ile
                130                 135                 140
Phe Asp Phe Asp Lys Ile Lys Pro Pro Ile Tyr Tyr Lys Ala Ala Glu
145                 150                 155                 160
Lys Thr Glu Lys Phe Ala Pro Leu Gly Tyr Lys Glu Glu Met Thr Leu
                    165                 170                 175
Glu Glu Ile Leu Glu Lys His Glu Lys Gly Arg Glu Tyr Gly His Leu
                180                 185                 190
Ile Lys Asp Lys Gln Phe Tyr Pro Leu Leu Ile Asp Ser Glu Gly Asn
                195                 200                 205
Val Leu Ser Met Pro Pro Ile Ile Asn Ser Glu Phe Thr Gly Arg Val
        210                 215                 220
Thr Thr Asp Thr Lys Asn Val Phe Ile Asp Val Thr Gly Trp Lys Leu
225                 230                 235                 240
Glu Lys Val Met Leu Ala Leu Asn Val Met Val Thr Ala Leu Ala Glu
                    245                 250                 255
Arg Gly Gly Lys Ile Arg Ser Val Arg Val Val Tyr Lys Asp Phe Glu
                260                 265                 270
Ile Glu Thr Pro Asp Leu Thr Pro Lys Glu Phe Glu Val Glu Leu Asp
                275                 280                 285
Tyr Ile Arg Lys Leu Ser Gly Leu Glu Leu Asn Asp Gly Glu Ile Lys
        290                 295                 300
Glu Leu Leu Glu Lys Met Met Tyr Glu Val Glu Ile Ser Arg Gly Arg
305                 310                 315                 320
Ala Lys Leu Lys Tyr Pro Ala Phe Arg Asp Asp Ile Met His Ala Arg
                    325                 330                 335
Asp Ile Leu Glu Asp Val Leu Ile Ala Tyr Gly Tyr Asn Asn Ile Glu
                340                 345                 350
Pro Glu Glu Pro Lys Leu Ala Val Gln Gly Arg Gly Asp Pro Phe Lys
                355                 360                 365
Asp Phe Glu Asp Ala Ile Arg Asp Leu Met Val Gly Phe Gly Leu Gln
        370                 375                 380
Glu Val Met Thr Phe Asn Leu Thr Asn Lys Val Gln Phe Lys Lys
385                 390                 395                 400
Met Asn Ile Pro Glu Glu Ile Val Glu Ile Ala Asn Pro Ile Ser
                    405                 410                 415
Gln Arg Trp Ser Ala Leu Arg Lys Trp Ile Leu Pro Ser Leu Met Glu
```

```
                420             425             430
Phe Leu Ser Asn Asn Thr His Glu Glu Tyr Pro Gln Arg Ile Phe Glu
        435                 440                 445
Val Gly Leu Ala Thr Leu Ile Asp Glu Ser Arg Glu Thr Lys Thr Val
    450                 455                 460
Ser Glu Pro Lys Leu Ala Val Ala Leu Ala Gly Thr Gly Tyr Thr Phe
465                 470                 475                 480
Thr Asn Ala Lys Glu Ile Leu Asp Ala Leu Met Arg His Leu Gly Phe
                485                 490                 495
Glu Tyr Glu Ile Glu Glu Val Glu His Gly Ser Phe Ile Pro Gly Arg
            500                 505                 510
Ala Gly Lys Ile Ile Val Asn Gly Arg Asp Ile Gly Ile Ile Gly Glu
        515                 520                 525
Val His Pro Gln Val Leu Glu Asn Trp Asn Ile Glu Val Pro Val Val
    530                 535                 540
Ala Phe Glu Ile Phe Leu Arg Pro Leu Tyr Arg His
545                 550                 555

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence:Primer
      Ec-B1-F

<400> SEQUENCE: 55
gcaccgcata tgaaattcag tgaactgtgg ttac                              34

<210> SEQ ID NO 56
<211> LENGTH: 34
<212> TYPE: DNA
<213> ORGANISM: Artificial Sequence
<220> FEATURE:
<223> OTHER INFORMATION: Description of Artificial Sequence:Primer
      Ec-B5-R

<400> SEQUENCE: 56
gtgcctcgag cgggatgttg ttgtagccgt aaac                              34

<210> SEQ ID NO 57
<211> LENGTH: 43
<212> TYPE: DNA
<213> ORGANISM: Artificial Sequence
<220> FEATURE:
<223> OTHER INFORMATION: Description of Artificial Sequence:Primer
      Ec-B3/4-R

<400> SEQUENCE: 57
gtgcctcgag acgcttcggc agcgttgctt cgttggtgat atc                    43

<210> SEQ ID NO 58
<211> LENGTH: 34
<212> TYPE: DNA
<213> ORGANISM: Artificial Sequence
<220> FEATURE:
<223> OTHER INFORMATION: Description of Artificial Sequence:Primer
      Ec-B3/4-F

<400> SEQUENCE: 58
gcacgccata tggttcaacc ggaaatcgtt ccgg                              34

<210> SEQ ID NO 59
```

```
<211> LENGTH: 37
<212> TYPE: DNA
<213> ORGANISM: Artificial Sequence
<220> FEATURE:
<223> OTHER INFORMATION: Description of Artificial Sequence:Primer
      Tt-B1-F

<400> SEQUENCE: 59
gccgcccata tgagggtgcc cttctcctgg ctaaaag                              37

<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence:Primer
      Tt-B5-R

<400> SEQUENCE: 60
gctcgaagct tggggatggt ctcgtagccc tggatgc                              37

<210> SEQ ID NO 61
<211> LENGTH: 44
<212> TYPE: DNA
<213> ORGANISM: Artificial Sequence
<220> FEATURE:
<223> OTHER INFORMATION: Description of Artificial Sequence:Primer
      Tt-B3/4-R

<400> SEQUENCE: 61
gctcgaagct tcgggggctt ggggcttccc gcctcgagga gggc                      44

<210> SEQ ID NO 62
<211> LENGTH: 37
<212> TYPE: DNA
<213> ORGANISM: Artificial Sequence
<220> FEATURE:
<223> OTHER INFORMATION: Description of Artificial Sequence:Primer
      Tt-B3/4-F

<400> SEQUENCE: 62
gccgcccata tggccctgaa ggcggaggcc cttcccc                              37

<210> SEQ ID NO 63
<211> LENGTH: 35
<212> TYPE: DNA
<213> ORGANISM: Artificial Sequence
<220> FEATURE:
<223> OTHER INFORMATION: Description of Artificial Sequence:Primer
      Ph-B1-F

<400> SEQUENCE: 63
ggcgcgccca tatgccaaag ttcgacgttt caaag                                35

<210> SEQ ID NO 64
<211> LENGTH: 29
<212> TYPE: DNA
<213> ORGANISM: Artificial Sequence
<220> FEATURE:
<223> OTHER INFORMATION: Description of Artificial Sequence:Primer
      Ph-B5-R

<400> SEQUENCE: 64
agctcgaggg gctctatgtt attatatcc                                       29

<210> SEQ ID NO 65
<211> LENGTH: 30
<212> TYPE: DNA
```

<213> ORGANISM: Artificial Sequence
<220> FEATURE:
<223> OTHER INFORMATION: Description of Artificial Sequence:Primer
      Ph-B3/4-R

<400> SEQUENCE: 65
ggctcgagta aatctggggt ttcaatttcg         30

<210> SEQ ID NO 66
<211> LENGTH: 37
<212> TYPE: DNA
<213> ORGANISM: Artificial Sequence
<220> FEATURE:
<223> OTHER INFORMATION: Description of Artificial Sequence:Primer
      Ph-B3/4-F

<400> SEQUENCE: 66
gccggcccca tatggaggtt aaaaagagta acgtaac         37

<210> SEQ ID NO 67
<211> LENGTH: 35
<212> TYPE: DNA
<213> ORGANISM: Artificial Sequence
<220> FEATURE:
<223> OTHER INFORMATION: Description of Artificial Sequence:Primer
      Ec-Mu-F

<400> SEQUENCE: 67
ggcctgcata ccgattggtc tcaccgttat gagcg         35

<210> SEQ ID NO 68
<211> LENGTH: 35
<212> TYPE: DNA
<213> ORGANISM: Artificial Sequence
<220> FEATURE:
<223> OTHER INFORMATION: Description of Artificial Sequence:Primer
      Ec-Mu-R

<400> SEQUENCE: 68
cgctcataac ggtgagacca atcggtatgc aggcc         35

<210> SEQ ID NO 69
<211> LENGTH: 33
<212> TYPE: DNA
<213> ORGANISM: Artificial Sequence
<220> FEATURE:
<223> OTHER INFORMATION: Description of Artificial Sequence:Tt-Mu-F

<400> SEQUENCE: 69
ggcctgcgca ccgagtggag ccaccgcttt gag         33

<210> SEQ ID NO 70
<211> LENGTH: 33
<212> TYPE: DNA
<213> ORGANISM: Artificial Sequence
<220> FEATURE:
<223> OTHER INFORMATION: Description of Artificial Sequence:Tt-Mu-R

<400> SEQUENCE: 70
ctcaaagcgg tggctccact cggtgcgcag gcc         33

<210> SEQ ID NO 71
<211> LENGTH: 30
<212> TYPE: DNA
<213> ORGANISM: Artificial Sequence
<220> FEATURE:
<223> OTHER INFORMATION: Description of Artificial Sequence:Primer
      Ph-Mu-F

```
<400> SEQUENCE: 71
gaaggagaga agtgtggata ggaatcttcg                                      30

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence:Primer
      Ph-Mu-R

<400> SEQUENCE: 72
cgaagattcc tatccacact tctctccttc                                      30

<210> SEQ ID NO 73
<211> LENGTH: 17
<212> TYPE: DNA
<213> ORGANISM: Artificial Sequence
<220> FEATURE:
<223> OTHER INFORMATION: Description of Artificial Sequence:T7 promoter

<400> SEQUENCE: 73
taatacgact cactata                                                    17
```

POLYPEPTIDE HAVING ACTIVITY OF AMINOACYL-TRNA SYNTHETASE AND USE THEREOF

This Nonprovisional application claims priority under 35 U.S.C. §119(a) on Patent Application No. 029236/2008 filed in Japan on Feb. 8, 2008, the entire contents of which are hereby incorporated by reference.

FIELD OF THE INVENTION

The present invention relates to polypeptides having aminoacyl-tRNA synthetase activity and use thereof. More specifically, the present invention relates to a polypeptide having aminoacyl-tRNA synthetase activity that exhibits high specificity of association between an unnatural amino acid and tRNA and use thereof.

BACKGROUND OF THE INVENTION

In recent years, the development of genetic engineering and the resulting sufficiency of information on three-dimensional protein structures, genome sequences, and the like have made it possible to create a protein with a new function by artificially altering a protein or, specifically, to create a protein with new activity by altering, based on a protein having certain activity, some amino-acid residues of the protein. For alteration of amino-acid residues to other amino-acid residues, natural amino acids are limited as options, and as such, may make it difficult to produce a protein having a desired function and desired activity.

Proposed in view of this as a method for expanding the functions of a protein are various methods that involves the introduction of an unnatural amino acid into a protein (e.g., see Wang, L., and Schultz, P. G., Expanding the genetic code. *Angew Chem Int Ed Engl*, 2005, 44, 34-66.). Among them, a method that involves the use of an aminoacyl-tRNA synthetase (hereinafter referred to sometimes as "aaRS") mutant has recently been developed as a method that can be used in living cells with high yields (International Publication No. 2003/014354 Pamphlet (published on Feb. 20, 2003), Lee, N., Bessho, Y., Wei, K., Szostak, J. W., and Suga, H., Ribozyme-catalyzed tRNA aminoacylation. *Nat Struct Biol*, 2000, 7, 28-33.).

An aaRS exists in all living organisms. An aaRS is responsible for faithfully translating a genetic code by accurately associating an amino acid with tRNA. A reaction catalyzed by an aaRS includes a first step of activating an amino acid with ATP and a second step of adding an activated aminoacyl adenylate intermediate to the 3'-end of tRNA. Both of the reactions are carried out at a single active site (aminoacylation active site) (Fersht, A. R., and Kaethner, M. M., Mechanism of aminoacylation of tRNA. Proof of the aminoacyl adenylate pathway for the isoleucyl- and tyrosyl-tRNA synthetases from *Escherichia coli* K12. *Biochemistry*, 1976, 15, 818-823; and Freist, W., and Sternbach, H., Tyrosyl-tRNA synthetase from baker's yeast. Order of substrate addition, discrimination of 20 amino acids in aminoacylation of tRNATyr-C-C-A and tRNATyr-C-C-A(3'NH$_2$). *Eur J Biochem*, 1988, 177, 425-433.).

There are two classes of aaRS, each with its own origin of evolution, and each of the classes includes 10 aaRSs (Eriani, G., Delarue, M., Poch, O., Gangloff, J., and Moras, D., Partition of tRNA synthetases into two classes based on mutually exclusive sets of sequence motifs. *Nature*, 1990, 347, 203-206.). A class I aaRS has an aminoacylation active site called a Rossman-fold domain. Meanwhile, a class II aaRSs does not have a Rossman-fold domain, but has an aminoacylation active site surrounded by an antiparallel beta-sheet. An aaRS must associate an amino acid with tRNA accurately. tRNAs are large molecules whose molecular weight exceeds 20,000, and vary in sequence. Meanwhile, amino acids are small molecules that share an α-amino group and an α-carboxyl group as common structures, and differ only in side chain. This makes it more difficult for an aaRS to discriminate between amino acids than to discriminate between tRNAs. For example, isoleucine and valine differ solely in methyl group, and it is believed to be difficult for an enzyme to recognize the difference (Pauling, L., *The Probability of Errors in the Process of Synthesis of Protein Molecules*, 1957.).

For this reason, each of seven types of natural aaRS, which amount to one third of all the natural aaRSs, namely an isoleucyl-tRNA synthetase (hereinafter referred to as "IleRS") of class I, a valyl-tRNA synthetase (hereinafter referred to as "ValRS") of class I, a leucyl-tRNA synthetase (hereinafter referred to as "LeuRS") of class I, an alanyl-tRNA synthetase (hereinafter referred to as "AlaRS") of class II, a prolyl-tRNA synthetase (hereinafter referred to as "ProRS") of class II, a threonyl-tRNA synthetase (hereinafter referred to as "ThrRS") of class II, and a phenylalanyl-tRNA synthetase (hereinafter referred to as "PheRS") of class II, is known to have an aminoacylation active site, serving as an active site, which not only recognizes a correct substrate amino acid but also misrecognizes another amino acid similar the correct substrate amino acid (Crepin, T., Yaremchuk, A., Tukalo, M., and Cusack, S., Structures of two bacterial prolyl-tRNA synthetases with and without a cis-editing domain. *Structure*, 2006, 14, 1511-1525.; Dock-Bregeon, A., Sankaranarayanan, R., Romby, P., Caillet, J., Springer, M., Rees, B., Francklyn, C. S., Ehresmann, C., and Moras, D., Transfer RNA-mediated editing in threonyl-tRNA synthetase. The class II solution to the double discrimination problem. *Cell*, 2000, 103, 877-884.; Fukai, S., Nureki, O., Sekine, S., Shimada, A., Tao, J., Vassylyev, D. G., and Yokoyama, S., Structural basis for double-sieve discrimination of L-valine from L-isoleucine and L-threonine by the complex of tRNA (Val) and valyl-tRNA synthetase. *Cell*, 2000, 103, 793-803.; Fukunaga, R., and Yokoyama, S., Aminoacylation complex structures of leucyl-tRNA synthetase and tRNALeu reveal two modes of discriminator-base recognition. *Nat Struct Mol Biol*, 2005, 12, 915-922.; Lin, L., Hale, S. P., and Schimmel, P., Aminoacylation error correction. *Nature*, 1996, 384, 33-34.; Nomanbhoy, T. K., Hendrickson, T. L., and Schimmel, P., Transfer RNA-dependent translocation of misactivated amino acids to prevent errors in protein synthesis. *Mol Cell*, 1999 4, 519-528.; Nureki, O., Vassylyev, D. G., Tateno, M., Shimada, A., Nakama, T., Fukai, S., Konno, M., Hendrickson, T. L., Schimmel, P., and Yokoyama, S., Enzyme structure with two catalytic sites for double-sieve selection of substrate. *Science*, 1998, 280, 578-582.; Roy, H., Ling, J., Irnov, M., and Ibba, M., Post-transfer editing in vitro and in vivo by the beta subunit of phenylalanyl-tRNA synthetase. *EMBO J*, 2004, 23, 4639-4648.; Ruan, B., and Soll, D., The bacterial YbaK protein is a Cys-tRNAPro and Cys-tRNA Cys deacylase. *J Biol Chem*, 2005, 280, 25887-25891.; Sokabe, M., Okada, A., Yao, M., Nakashima, T., and Tanaka, I., Molecular basis of alanine discrimination in editing site. *Proc Natl Acad Sci USA*, 2005, 102, 11669-11674.; and Swairjo, M. A., Otero, F. J., Yang, X. L., Lovato, M. A., Skene, R. J., McRee, D. E., Ribas de Pouplana, L., and Schimmel, P., Alanyl-tRNA synthetase crystal structure and design for acceptor-stem recognition. *Mol Cell*, 2004, 13, 829-841.). As a result of such misrecognition, an aminoacyl adenylate intermediate is produced by activation with an amino acid different from the correct substrate, or aminoacyl tRNA is produced as a product thereof.

However, each of these aaRSs has an editing reaction active site separate from the aminoacylation active site, and as such, has activity to hydrolyze the mistakenly produced aminoacyl adenylate intermediate into an amino acid and an inorganic phosphoric acid or activity to hydrolyze aminoacyl tRNA into an amino acid and tRNA. The editing reaction active site exists in a domain independent of a domain containing the aminoacylation active site (Fukai, S. et. al., *Cell*, 2000, 103, 793-803.; Fukunaga, R., and Yokoyama, S., *Nat Struct Mol Biol*, 2005, 12, 915-922.; Nureki, O. et. al., *Science*, 1998, 280, 578-582.; Kotik-Kogan, O., Moor, N., Tworowski, D., and Safro, M., Structural basis for discrimination of L-phenylalanine from L-tyrosine by phenylalanyl-tRNA synthetase. *Structure*, 2005, 13, 1799-1807.; and Ribas de Pouplana, L., and Schimmel, P., Two classes of tRNA synthetases suggested by sterically compatible dockings on tRNA acceptor stem. *Cell*, 2001, 104, 191-193.). The domain is called an editing reaction domain. Specifically, each of these aaRSs strictly recognizes only a single amino acid by recognizing the separate properties (size, hydrophilicity, hydrophobicity) of an amino-acid side chain by the two reaction sites (Fukai, S. et. al., *Cell*, 2000, 103, 793-803.).

It should be noted that each of the aaRSs other than the aforementioned seven types of aaRS each of which has an editing reaction active site does not have an editing reaction site, and as such, recognizes a single amino acid only by an aminoacylation active site (Fersht, A. R., Shindler, J. S., and Tsui, W. C., Probing the limits of protein-amino acid side chain recognition with the aminoacyl-tRNA synthetases. Discrimination against phenylalanine by tyrosyl-tRNA synthetases. *Biochemistry*, 1980 19, 5520-5524.).

Incidentally, an aaRS mutant is produced by substituting an amino-acid residue of a substrate recognition site of a wild-type aaRS. For example, TyrRS is the first aaRS that succeeded in alteration for introduction of an unnatural amino acid. Further, TyrRS has a large amino-acid-binding pocket for recognizing a comparatively large amino acid, tyrosine, and presently has the largest number of mutants specific to unnatural amino acids (International Publication No. 2003/014354 Pamphlet; and Wang, L., Xie, J., and Schultz, P. G., Expanding the genetic code. *Annu Rev Biophys Biomol Struct*, 2006, 35, 225-249.). For example, there has been a report on a tyrosyl-tRNA synthetase (hereinafter referred to as "TyrRS") mutant. Specifically, in International Publication No. 2003/014354 Pamphlet, known examples of a mutant that recognizes 3-iodotyrosine, which is an unnatural amino acid, include an *Escherichia coli*-derived TyrRS mutant and a *Methanocaldococcus jannaschii*-derived TyrRS mutant (MjIYRS).

SUMMARY OF THE INVENTION

As mentioned above, aaRS mutants that specifically recognize unnatural amino acids have been produced so far. However, the substrate specificity of such an aaRS mutant to an unnatural amino acid is not sufficient. Therefore, there has been a demand for the development of a new aaRS mutant.

It is an object of the present invention to provide a new aaRS that exhibits high specificity to an amino acid to be recognized and a technique that involves the use of such an aaRS.

In order to attain the foregoing object, the inventors diligently studied. As a result, the inventors newly found that by binding an aaRS-derived editing polypeptide having an editing reaction active site to a specific domain in an altered polypeptide obtained by so altering a class I aaRS having no editing reaction active site that an unnatural amino acid is recognized, the altered polypeptide is made to exhibit editing reaction activity without losing its function of recognizing an unnatural amino acid. The present invention, based on the new findings, encompasses the following inventions.

That is, in order to attain the foregoing object, a polypeptide according to the present invention is a polypeptide having aminoacyl-tRNA synthetase activity, the polypeptide including: an altered polypeptide obtained by altering an arginyl-tRNA synthetase, a cysteinyl-tRNA synthetase, a methionyl-tRNA synthetase, a glutaminyl-tRNA synthetase, a glutamyl-tRNA synthetase, a lysyl-tRNA synthetase, a tyrosyl-tRNA synthetase, or a tryptophanyl-tRNA synthetase so that an unnatural amino acid is recognized; and an editing polypeptide containing an editing reaction active site derived from a phenylalanyl-tRNA synthetase, a leucyl-tRNA synthetase, an isoleucyl-tRNA synthetase, a valyl-tRNA synthetase, an alanyl-tRNA synthetase, a prolyl-tRNA synthetase, or a threonyl-tRNA synthetase, the editing polypeptide having been either inserted between a Rossman-fold N domain and a Rossman-fold C domain that exist in the altered polypeptide, or bound to an N terminal of the altered polypeptide.

In the polypeptide according to the present invention, it is more preferable that the editing polypeptide have been inserted into a CP1 domain, had by the altered polypeptide, which lies between the Rossman-fold N domain and the Rossman-fold C domain.

In the polypeptide according to the present invention, it is more preferable that a linker polypeptide that connects the editing polypeptide with the altered polypeptide have been further inserted.

In the polypeptide according to the present invention, the altered polypeptide may be a tyrosyl-tRNA synthetase altered so as to recognize an unnatural amino acid.

In the polypeptide according to the present invention, it is more preferable that the tyrosyl-tRNA synthetase be derived from eukaryotic organisms or eubacteria.

In the polypeptide according to the present invention, it is more preferable that the eubacteria be *Escherichia coli*.

In the polypeptide according to the present invention, the tyrosyl-tRNA synthetase may be a polypeptide altered so as to recognize a tyrosine derivative.

In the polypeptide according to the present invention, the tyrosine derivative may be 3-iodotyrosine.

In the polypeptide according to the present invention, it is more preferable that the altered polypeptide be a polypeptide as set forth in either of (a) and (b): (a) a polypeptide consisting of an amino-acid sequence represented by SEQ ID NO: 1; and (b) a polypeptide (i) consisting of an amino-acid sequence, represented by SEQ ID NO: 1 with a deletion, insertion, substitution, or addition of one or several amino acids and (ii) having activity to bind 3-iodotyrosine to tRNA.

In the polypeptide according to the present invention, the editing polypeptide may be derived from a phenylalanyl-tRNA synthetase.

In the polypeptide according to the present invention, it is more preferable that the phenylalanyl-tRNA synthetase be derived from eukaryotic organisms or archaebacteria.

In the polypeptide according to the present invention, it is more preferable that the archaebacteria belong to the genus *Pyrococcus*.

In the polypeptide according to the present invention, it is more preferable that the archaebacteria be *Pyrococcus horikoshii*.

In the polypeptide according to the present invention, it is more preferable that the editing polypeptide be a polypeptide as set forth in either of (c) and (d): (c) a polypeptide consisting of an amino-acid sequence represented by SEQ ID NO: 2; and (d) a polypeptide (i) consisting of an amino-acid sequence, represented by SEQ ID NO: 2 with a deletion, insertion, substitution, or addition of one or several amino acids and (ii) having activity to hydrolyze tyrosine bound to tRNA or activity to hydrolyze tyrosyl adenylate intermediate into tyrosine and an inorganic phosphoric acid.

It is more preferable that the polypeptide according to the present invention be a polypeptide as set forth in either of (e) and (f): (e) a polypeptide consisting of an amino-acid sequence represented by SEQ ID NO: 3; and (f) a polypeptide (i) consisting of an amino-acid sequence, represented by SEQ ID NO: 3 with a deletion, insertion, substitution, or addition of one or several amino acids and (ii) having activity to hydrolyze tyrosine bound to tRNA or activity to hydrolyze tyrosyl adenylate intermediate into tyrosine and an inorganic phosphoric acid and activity to bind an unnatural amino acid to tRNA.

In the polypeptide according to the present invention, it is more preferable that: the altered polypeptide be a tyrosyl-tRNA synthetase altered so as to recognize an unnatural amino acid and the editing polypeptide contain an editing reaction active site derived from a phenylalanyl-tRNA synthetase; or the altered polypeptide be a methionyl-tRNA synthetase altered so as to recognize an unnatural amino acid and the editing polypeptide contain an editing reaction active site derived from a leucyl-tRNA synthetase.

Further, the present invention encompasses a polynucleotide coding for the polypeptide according to the present invention.

Further, a production method according to the present invention is a method for producing a polypeptide having aminoacyl-tRNA synthetase activity, the method including: a preparing step of preparing a polynucleotide in which a polynucleotide coding for an editing polypeptide containing an editing reaction active site derived from a phenylalanyl-tRNA synthetase, a leucyl-tRNA synthetase, an isoleucyl-tRNA synthetase, a valyl-tRNA synthetase, an alanyl-tRNA synthetase, a prolyl-tRNA synthetase, or a threonyl-tRNA synthetase has been introduced into a polynucleotide coding for an altered polypeptide obtained by altering an arginyl-tRNA synthetase, a cysteinyl-tRNA synthetase, a methionyl-tRNA synthetase, a glutaminyl-tRNA synthetase, a glutamyl-tRNA synthetase, a lysyl-tRNA synthetase, a tyrosyl-tRNA synthetase, or a tryptophanyl-tRNA synthetase so that an unnatural amino acid is recognized; and an expressing step of expressing a polypeptide coded for by the polynucleotide obtained in the preparing step, the preparing step includes preparing either a polynucleotide in which the editing polypeptide has been introduced so as to be positioned between a Rossman-fold N domain and a Rossman-fold C domain that exist in the altered polypeptide, or a polynucleotide in which the editing polypeptide has been introduced so as to be bound to an N terminal of the altered polypeptide.

Additional objects, features, and strengths of the present invention will be made clear by the description below. Further, the advantages of the present invention will be evident from the following explanation in reference to the drawings.

DESCRIPTION OF THE EMBODIMENTS

Figure 1:
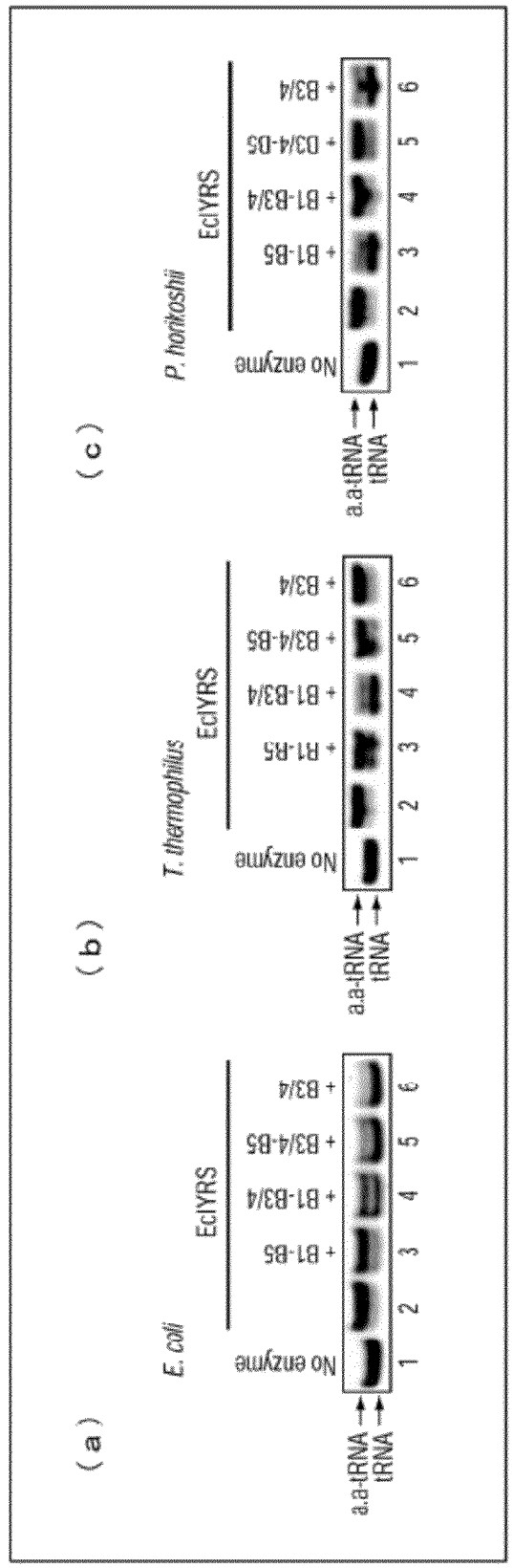
FIG. 1, showing an embodiment of the present invention, shows the hydrolysis activity of editing reaction peptides.

<1. Polypeptide According to the Present Invention>

A polypeptide according to the present invention only needs to be a polypeptide having aminoacyl-tRNA synthetase activity, the polypeptide including: an altered polypeptide obtained by altering an arginyl-tRNA synthetase (hereinafter referred to as "ArgRS"), a cysteinyl-tRNA synthetase (hereinafter referred to as "CysRS"), a methionyl-tRNA synthetase (hereinafter referred to as "MetRS"), a glutaminyl-tRNA synthetase (hereinafter referred to as "GlnRS"), a glutamyl-tRNA synthetase (hereinafter referred to as "GluRS"), a lysyl-tRNA synthetase (hereinafter referred to as "LysRS"), a tyrosyl-tRNA synthetase (hereinafter referred to as "TyrRS"), or a tryptophanyl-tRNA synthetase (hereinafter referred to as "TrpRS") so that an unnatural amino acid is recognized; and an editing polypeptide derived from a PheRS, a LeuRS, an IleRS, a ValRS, an AlaRS, a ProRS, or a ThrRS, the editing polypeptide having been either inserted between a Rossman-fold N domain and a Rossman-fold C domain that exist in the altered polypeptide, or bound to an N terminal of the altered polypeptide.

This makes it possible to obtain an aaRS that exhibits excellent substrate specificity. For example, in order to cause a substrate for the tyrosyl-tRNA synthetase to be an unnatural amino acid (e.g., 3-iodotyrosine) other than tyrosine, it is necessary to alter the amino-acid recognition domain of the TyrRS. Depending on how the domain is altered, the domain may recognize an amino acid other than the unnatural amino acid after alteration. However, the polypeptide according to the present invention has the editing polypeptide. Moreover, the editing polypeptide has been either inserted between the Rossman-fold N domain and the Rossman-fold C domain, or bound to the N terminal of the altered polypeptide. Therefore, the editing polypeptide functions effectively. That is, even in the case of misrecognition of an amino acid, such misrecognition can be corrected by the editing polypeptide. This makes it possible to obtain an aminoacyl-tRNA synthetase that exhibits high specificity of association between an unnatural amino acid and tRNA.

In this specification, the "polypeptide having aminoacyl-tRNA synthetase activity" means a polypeptide having the aminoacyl-tRNA synthesis activity of an aminoacyl-tRNA synthetase. The "aminoacyl-tRNA synthesis activity" means activity that synthesizes aminoacyl-tRNA by binding an amino acid to tRNA.

Further, the "unnatural amino acid" means an amino acid other than amino acids genetically encoded by natural living organisms. It should be noted that the "amino acids genetically encoded" mean 22 types of amino acid, namely 20 types of standard amino acid universally used by living organisms, selenomethionine, and pyrrolidine.

Further, examples of the unnatural amino acid include: 3-halogen-substituted tyrosine such as 3-iodotyrosine, 3-hydroxytyrosine, and 3-azidotyrosine, each having a substituent at the 3-position of tyrosine; parabenzoylphenylalanine, and 4-iodophenylalanine, 4-azidophenylalanine, each having a substituent at the 4-position of phenylalanine; and the like.

[1-1. Altered Polypeptide]

In this specification, the "altered polypeptide" only needs to be a polypeptide obtained by altering an ArgRS, a CysRS, a MetRS, a GlnRS, a GluRS, a LysRS, a TyrRS, or a TrpRS so that an unnatural amino acid is recognized.

The ArgRS, the CysRS, the MetRS, the GlnRS, the GluRS, the LysRS, the TyrRS, and the TrpRS are not particularly limited, but are preferably derived from eubacteria such as *Escherichia coli* and heat-resistant bacteria, archaebacteria or eukaryotic organisms such as yeasts, animals, and plants, or in particular, from *Escherichia coli* or archaebacteria.

An aaRS derived from archaebacteria is not used in the cells of eukaryotic organisms to synthesize a protein containing an unnatural amino acid, but can be used in the cells of prokaryotic organisms. Therefore, an altered polypeptide obtained with use of an aaRS derived from archaebacteria can be used in the cells of prokaryotic organisms or in cell-free translation systems derived from prokaryotic organisms.

Further, an aaRS derived from *Escherichia coli* cannot be used in the cells of prokaryotic organisms, but functions in the cells of eukaryotic organisms (yeast cells, plant cells, insect cells, and mammalian cells), and as such, is used to synthesize a protein containing an unnatural amino acid. Therefore, an altered polypeptide obtained with use of an aaRS derived from *Escherichia coli* can be used for protein synthesis in the cells of eukaryotic organisms or in cell-free translations system derived from eukaryotic organisms.

There is no particular limit on how to obtain an ArgRS or the like from such a living organism as mentioned above. However, for example, based on the following conventional publicly-known base sequences and the like, it is possible to obtain, by a nucleic-acid amplification reaction such as PCR, a polynucleotide coding for an ArgRS or the like and to express a polypeptide coded for by the polynucleotide.

For a DNA sequence of ArgRS, refer to GenBank Accession No. AP_002496, for example.

For a DNA sequence of CysRS, refer to GenBank Accession No. AP_001173, for example.

For a DNA sequence of MetRS, refer to GenBank Accession No. AP_002712, for example.

For a DNA sequence of GlnRS, refer to GenBank Accession No. P00962, for example.

For a DNA sequence of GluRS, refer to GenBank Accession No. AP_001318, for example.

For a DNA sequence of LysRS, refer to GenBank Accession No. AP_004631, for example.

For a DNA sequence of TyrRS, refer to GenBank Accession No. AP_00259, for example.

For a DNA sequence of TrpRS, refer to GenBank Accession No. AP_004406, for example.

An amino acid serving as a substrate for an aaRS may be altered with use of a conventional publicly-known method. For such a method, refer to "Lee, N. et al., *Nat Struct Biol*, 2000, 7, 28-33" mentioned above, for example. Alternatively, an amino acid serving as a substrate for an aaRS may be altered by introducing a mutation into the aaRS according to a technique, described in International Publication No. 2003/014354 Pamphlet, which involves the use of PCR. For a method for screening an aaRS mutant obtained after altering an amino-acid recognition site, refer to "Wang, L., Brock, A., Herberich, B., and Schultz, P. G., Expanding the genetic code of *Escherichia coli*. *Science*, 2001 292, 498-500" mentioned above, for example.

Further, the altered polypeptide may be a conventional publicly-known aaRS altered in terms of the amino acid it recognizes. For example, the altered polypeptide may be an EcIYRS, a MjIYRS, or the like. Further, the altered polypeptide may be one of the aaRS mutants disclosed in "Wang, L. et al., *Annu Rev Biophys Biomol Struct*, 2006, 35, 225-249". "Wang, L. et al., *Annu Rev Biophys Biomol Struct*, 2006, 35, 225-249" enumerates an *Escherichia coli*-derived TyrRS mutant specific to p-benzoylphenylalanine, an *Escherichia coli*-derived TyrRS mutant specific to p-azidophenylalanine, an *Escherichia coli*-derived TyrRS mutant specific to p-iodophenylalanine, an *Escherichia coli*-derived TyrRS mutant specific to p-acetylphenylalanine, a *M. jannaschii*-derived TyrRS mutant specific to p-benzoylphenylalanine, a *M. jannaschii*-derived TyrRS mutant specific to p-azidophenylalanine, a *M. jannaschii*-derived TyrRS mutant specific to p-iodophenylalanine, a *M. jannaschii*-derived TyrRS mutant specific to p-acetylphenylalanine, a *M. jannaschii*-derived TyrRS mutant specific to N-acetylgalactosamine-α-O-threonine, a *M. jannaschii*-derived TyrRS mutant specific to N-acetylglucosamine-α-O-serine, and the like. Further, the altered polypeptide of the present invention may be realized by a *M. jannaschii*-derived TyrRS mutant specific to trifluoromethyldiazinylphenylalanine (see Tippmann, E. M. et al., *Chembiochem*, 2007, 8, 2210-2214), a *M. jannaschii*-derived TyrRS mutant specific to p-carboxymethylphenylalanine (see Xie, J., Supekova, L., Schultz, P. G., *ACS Chem Biol.*, 2007, 2, 474-478), a *M. jannaschii*-derived TyrRS mutant specific to O-allyltyrosine (see Zhang, Z. et al., *Angew. Chem. Int. Ed.*, 2002, 41, 2840-2842), a *M. jannaschii*-derived TyrRS mutant specific to sulfotyrosine (see Liu, C. C., Schultz, P. G., *Nature biotechnology*, 2006, 24, 1436-1440), or the like. Among the examples thus enumerated, EcIYRSs derived from eubacterial aaRSs are preferred.

It should be noted that substituting histidine with alanine at the 70-position, asparagine acid with threonine at the 158-position, and isoleucine with serine at the 159-position of a *Methanococcus jannaschii* TyrRS makes it possible to produce a MjIYRS by altering the substrate amino acid of the TyrRS from tyrosine to an unnatural amino acid 3-iodotyrosine.

Further, for example, the altered polypeptide for use in the polypeptide according to the present invention can be realized by a polypeptide altered so as to recognize a tyrosine derivative, or in particular, by a TyrRS mutant obtained by altering a TyrRS so that 3-iodotyrosine is recognized as a tyrosine derivative.

In this specification, the "tyrosine derivative" means tyrosine one of whose constituent atoms has a given substituent introduced thereinto, and the substituent is not limited in position into which it is introduced. Possible examples of the tyrosine derivative include tyrosine in which a hydrogen atom bound to a carbon atom at the 3-position of a phenolic aromatic ring has been substituted by another atom or a group of atoms, substituted by a halogen atom, or substituted by an iodine atom (e.g., 3-iodotyrosine). Further possible examples include tyrosine in which the 4-position of a phenolic aromatic ring has been substituted by a group of atoms including an O-methyl group (O-methyltyrosine), an azido group (azidophenylalanine), a benzoyl group (parabenzoylphenylalanine), an acetyl group (4-acetylphenylalanine), and a diazirine group (trifluoromethyldiazirinylphenylalanine), or by an iodine atom (4-iodophenylalanine). It should be noted that iodotyrosine is useful in that it can be used for phase determination in determining a crystal protein structure.

Further, an example of a TyrRS mutant obtained by altering a TyrRS so that the substrate amino acid becomes a tyrosine derivative is an *Escherichia coli*-derived TyrRS whose tyrosine at the 37-position has been substituted by valine, leucine, isoleucine, or alanine and whose glutamine at the 195-position has been substituted by alanine, cysteine, serine, or asparagine. The introduction of the aforementioned substitutions makes it possible to produce a TyrRS whose substrate amino acid has been altered from tyrosine to an unnatural amino acid 3-iodotyrosine.

In one embodiment, it is preferable that the altered polypeptide be a polypeptide consisting of an amino-acid sequence represented by SEQ ID NO: 1. The amino-acid sequence represented by SEQ ID NO: 1 is an amino-acid sequence of a polypeptide obtained by altering an *Escherichia coli*-derived TyrRS so that 3-iodotyrosine is recognized. Further, the altered polypeptide may be a polypeptide (i) consisting of an amino-acid sequence, represented by SEQ ID NO: 1 with a deletion, insertion, substitution, or addition of one or several amino acids and (ii) having activity to bind 3-iodotyrosine to tRNA.

[1-2. Editing Polypeptide]

In this specification, the "editing polypeptide" means a polypeptide having activity to hydrolyze an aminoacyl adenylate intermediate and aminoacyl tRNA, each having been produced by an aaRS's misrecognizing an amino acid different from the correct substrate amino acid, into an amino acid and an inorganic phosphoric acid and into an amino acid and tRNA, respectively (such activity being referred to as "editing reaction activity"). It should be noted that a domain including the editing polypeptide is referred to sometimes as an "editing reaction domain". aaRSs having editing polypeptides are IleRS, ValRS, LeuRS, AlaRS, ProRS, ThrRS, and PheRS. An editing polypeptide altered so as to exhibit editing reaction activity to something other than the aminoacyl tRNA and/or aminoacyl adenylate intermediate the original aaRS is intended to edit is also encompassed in the scope of "aaRS-derived editing polypeptide". For example, an IleRS-derived editing polypeptide, which hydrolyzes valyl tRNA, may be altered so as to hydrolyze binding of an amino acid other than valine (e.g., an unnatural amino acid) to tRNA. A person skilled in the art would be able to appropriately alter an editing polypeptide by substituting some of the amino acids constituting the editing polypeptide. However, for convenience of explanation, the term "aaRS-derived editing polypeptide" used in the description of this specification means an editing polypeptide that has not been altered in terms of the aminoacyl tRNA and/or aminoacyl adenylate intermediate it is intended to edit, if not otherwise specified.

There is no particular limit on how to obtain an editing polypeptide. For example, an editing polypeptide may be obtained as follows: With use as a template of a polynucleotide coding for an IleRS, a ValRS, a LeuRS, an AlaRS, a ProRS, a ThrRS, and a PheRS, the genome DNA of a living organism having these aaRS, or the like, a polynucleotide coding for the editing polypeptide is obtained by a nucleic-acid amplification reaction such as PCR with use of a primer designed based on the base sequence of a conventional publicly-known editing polypeptide; and with use of the polynucleotide in a cell-free translation system or a conventional publicly-known expression system such as a microorganism, a polypeptide coded for by the polynucleotide is expressed. The polypeptide may be expressed not only at a site known to be an active center, but also in an appropriate surrounding domain, among the editing reaction domain. For example, in the case of the after-mentioned *Pyrococcus horikoshii* PheRS, better editing reaction activity can be obtained by expressing a polypeptide so that a B3/4 domain is included.

The PheRS, the IleRS, the ValRS, the LeuRS, the AlaRS, the ProRS, and the ThrRS, from each of which the editing polypeptide is obtained, will be detailed below.

The PheRS is not particularly limited, but can be derived from eukaryotic organisms or prokaryotic organisms, preferably from prokaryotic organisms, or in particular, from archaebacteria, more preferably from the genus *Pyrococcus*, or most preferably from *Pyrococcus horikoshii*. For example, it is possible to use the beta-subunit of *Pyrococcus horikoshii* PheRS (refer to GenBank Accession No. NP_142611). It should be noted that the *Pyrococcus horikoshii* PheRS is disclosed, for example, in "Roy, H. et al., *EMBO J*, 2004, 23, 4639-4648", "Kotik-Kogan, O. et al., *Structure*, 2005, 13, 1799-1807", and Sasaki, H., et al., Structural and mutational studies of the amino acid-editing domain from archaeal/eukaryal phenylalanyl-tRNA synthetase, *Proc Natl Acad Sci USA*, 2006, 103, 14744-14749" and it has been specified that the B3/4 domain is an editing reaction site. Further, the editing reaction site of the PheRS has activity to hydrolyze tyrosyl tRNA and a tyrosyl adenylate intermediate. There are two types of PheRS: an alpha-subunit and a beta-subunit. Among these, it is the beta-subunit that includes the editing reaction domain.

In one embodiment, it is preferable that the editing polypeptide be a polypeptide consisting of an amino-acid sequence represented by SEQ ID NO: 2. In another embodiment, it is preferable that the editing polypeptide be a polypeptide (i) consisting of an amino-acid sequence, represented by SEQ ID NO: 2 with a deletion, insertion, substitution, or addition of one or several amino acids and (ii) having editing reaction activity. SEQ ID NO: 2 represents one of the amino-acid sequences of an editing polypeptide derived from a *Pyrococcus horikoshii*-derived PheRS, i.e., represents the amino-acid sequence of the B3/4 domain. The polypeptide consisting of these amino-acid sequences may have another polypeptide bound thereto, as long as the editing reaction activity is not impaired. For example, the polypeptide consisting of the amino-acid sequence of the B3/4 domain may have the after-mentioned B1 and B2 domains bound to the N terminal thereof, or may have a B5 domain bound to the C terminal thereof.

It should be noted that the PheRS is an enzyme that functions by alpha- and beta-heterodimers' combining to form a further dimer. Among these, the editing reaction domain exists in the beta-subunit. The beta-subunit consists of B1, B2, B3/4, B5, B6/7, and B8 domains, and the B3/4 domain is the editing reaction domain. In a eukaryotic or archaebacterial PheRS, there is a lack of B2 and B8 domains, i.e., there do not exist B2 and B8 domains. In some aaRSs, there stably exists a polypeptide including only an editing reaction domain and hydrolysis activity is retained. The inventors found that in cases where the editing polypeptide is obtained from a *Pyrococcus horikoshii*-derived PheRS, use of a polypeptide including a B3/4 domain makes it possible to exhibit extremely stable and satisfactory editing reaction activity. Therefore, when an editing polypeptide derived from a *Pyrococcus horikoshii* PheRS is employed, it is preferable to use a polypeptide including a B3/4 domain, and it is more preferable to use a polypeptide consisting of a B3/4 domain.

It should be noted that also when an editing polypeptide derived from an *Escherichia coli* PheRS is employed, it is preferable to use a polypeptide including a B3/4 domain, and it is more preferable to use a polypeptide consisting of a B3/4 domain.

Further, when an editing polypeptide derived from a *Thermus thermophilus* is employed, it is preferable to use a polypeptide of a B3/4 domain or of a B1-B3/4 domain to which B1 and B2 have been added, because excellent stability is obtained.

The LeuRS, the IleRS, the ValRS, the AlaRS, the ProRS, and the ThrRS are not particularly limited, but can be derived appropriately from eukaryotic organisms or prokaryotic organisms, preferably from prokaryotic organisms, and will be detailed below.

For LeuRS, refer to "Lincecum, T. L. et al., *Structural and Mechanistic Basis of Pre- and Posttransfer Editing by Leucyl-tRNA Synthetase Molecular Cell*, 2003, 11, 951-963", for example, in which the crystal structure of a *T. thermophilus* LeuRS is disclosed and an editing reaction site (domain including Thr247 to Thr252 and Leu329 to Asp347) is specified. Further, for example, "Fukunaga, R., and Yokoyama, S., *Nat Struct Mol Biol*, 2005, 12, 915-922" can be referred to, in which the crystal structure of a *P. horikoshii* LeuRS is disclosed and an editing reaction domain (from the vicinity of Pro205 to the vicinity of Phe433) is specified.

For IleRS, refer to "Nureki, O. et al., *Science*, 1998, 280, 578-582", for example, in which the crystal structure of a *T. thermophilus* IleRS is disclosed and an editing reaction site (domain including Trp232, Phe359, His384, and Tyr386) is specified.

For ValRS, refer to "Fukai, S. et al., *Cell*, 2000, 103, 793-803", for example, in which the crystal structure of a *T. thermophilus* ValRS is disclosed and an editing reaction site (domain including Thr214, Arg216, Thr219, Lys270, Thr272, Asp276, and Asp279) is specified.

For AlaRS, refer to "Beebe, K. et al., Distinct domains of tRNA synthetase recognize the same base pair, *Nature*, 2008, 451, 90-93", for example, which shows that an *E. coli* AlaRS polypeptide including Asp553 to Ala705 has editing reaction activity.

For ProRS, refer to "Crepin, T. et al., Structures of Two Bacterial Prolyl-tRNA Synthetases with and without a cis-Editing Domain, *Structure*, 2006, 14, 1511-1525", for example, in which the crystal structure of an *Enterococcus faecalis* ProRS is disclosed and an editing reaction domain (Thr237 to Gly390) is specified.

For ThrRS, refer to "Dock-Bregeon, A.-C. et al., Transfer RNA-Mediated Editing in Threonyl-tRNA Synthetase: The Class II Solution to the Double Discrimination Problem, *Cell*, 2000, 103, 877-884", for example, in which the crystal structure of an *E. coli* ThrRS is disclosed and an editing reaction site (domain including His73, His77, Cys182, and His186) is specified. Further, in FIG. 4 of "Korencic, D. et al., A free-standing proofreading domain is required for protein synthesis quality control in Archaea, *Proc Natl Acad Scie USA*, 2004, 101, 10260-10265", the amino-acid sequence alignment of an archaebacterial editing reaction domain is described.

As for these aaRSs whose editing reaction sites or editing reaction domains have been specified, polynucleotides coding for polypeptides containing editing reaction sites or the like are obtained by a nucleic-acid amplification reaction such as PCR. With use of the polynucleotides in a conventional publicly-known expression system, polypeptides coded for by the polynucleotides are expressed. The polypeptides are checked for editing reaction activity, and a polypeptide having editing reaction activity is judged to be an editing polypeptide.

Further, identical aaRSs share homology with one another across species in terms of the amino-acid sequence of an editing reaction site. For this reason, the editing reaction site of an aaRS of a living organism other than those described above can be specified by alignment with an aaRS whose editing reaction site has been specified. Based on this editing reaction site, an editing polypeptide derived from another living organism can be appropriately obtained by such a technique as described above.

[1-3. Positional Relationship Between the Altered Polypeptide and the Editing Polypeptide]

As described above, in the polypeptide according to the present invention, it is preferable that the editing polypeptide have been either inserted between a Rossman-fold N domain and a Rossman-fold C domain that exist in the altered polypeptide, or bound to an N terminal of the altered polypeptide.

In this specification, the "Rossman-fold domain" means a domain that universally exists in class I aaRS proteins and forms a Rossman-fold structure. The "Rossman-fold structure" means a beta-alpha-beta-alpha-beta structural unit in which beta-alpha-beta structures each having a concatenation of beta structures and an alpha helix of a peptide chain are repeated. In a Rossman-fold domain, there are two Rossman-fold structures arranged. The Rossman-fold structure on the N terminal is called a "Rossman-fold N domain", and the Rossmam-fold structure on the C terminal is called "Rossman-fold C domain". The total six of beta-structures in the Rossman filed domain are arranged in parallel with one another. The Rossman-fold structure has activity to bind to a nucleotide.

In one embodiment, it is preferable that the editing polypeptide have been inserted into a CP1 domain that lies between the Rossman-fold N domain and the Rossman-fold C domain.

In this specification, the "CP1 (connective peptide 1) domain" means a domain consisting of an amino acid sandwiched between N and C domains of a Rossman-fold domain on a primary sequence of an aaRS of class I.

Insertion of the editing polypeptide into the CP1 domain makes it possible to introduce the editing polypeptide while retaining the activity to bind an amino acid to tRNA.

In cases where the editing polypeptide has been bound the N terminal of the altered polypeptide, it is preferable that the N terminal of the editing polypeptide have been altered to methionine or an additional peptide whose N terminal is methionine have been added.

As described above, if the editing polypeptide is positioned between the Rossman-fold N domain and the Rossman-fold C domain, or preferably in the CP1 domain or at the N terminal of the altered polypeptide, the aminoacylation activity and the editing reaction activity are effectively exhibited. When inserted into one of the positions, the editing polypeptide not only can maintain its three-dimensional structure, but also will not disarray the three-dimensional structure of the altered polypeptide. Furthermore, the positional relationship between the editing polypeptide and the altered polypeptide in the present invention is appropriate from the point of view that the 3'-end of aminoacylated tRNA moves rapidly from the altered polypeptide to the editing polypeptide.

Further, the polypeptide according to the present invention may have a linker polypeptide inserted therein, the linker polypeptide being a polypeptide that connects the editing polypeptide with the altered polypeptide. The sequence and length of the linker polypeptide are not limited, and can be set appropriately by the editing polypeptide and the altered polypeptide. For example, it is preferable that a linker polypeptide having 2 to 10 serine or glycine residues be inserted into each of the N and C terminals of the editing polypeptide. Further, in cases where the polypeptide according to the present invention takes such a form that a PheRS-derived editing polypeptide has been inserted into a TyrRS mutant obtained by altering a TyrRS so that the amino acid to be recognized is an unnatural amino acid, it is only necessary that a polypeptide consisting of an amino-acid sequence represented by SEQ. ID. NO.: 50 be included as a linker at the N terminal of the editing polypeptide and a polypeptide consisting of an amino-acid sequence represented by SEQ. ID. NO.: 51 be included as a linker at the C terminal of the editing polypeptide.

[1-4. Combination of the Altered Polypeptide and the Editing Polypeptide]

As to which of the aaRSs, namely the ArgRS, the CysRS, the MetRS, the GlnRS, the GluRS, the LysRS, TyrRS, and the TrpRS, is selected as the altered polypeptide and which of a PheRS-derived editing polypeptide, an IleRS-derived editing polypeptide, a ValRS-derived editing polypeptide, a LeuRS-derived editing polypeptide, an AlaRS-derived editing polypeptide, a ProRS-derived editing polypeptide, and a ThrRS-derived editing polypeptide is selected as the editing polypeptide, there is no particular limit on their combinations. However, preferred combinations will be described below.

When the altered polypeptide is an aaRS obtained by altering the ArgRS, the CysRS, the MetRS, the GlnRS, the GluRS, the LysRS, the TyrRS, or the TrpRS, it is only necessary to select an editing polypeptide having activity to hydrolyze an aminoacyl adenylate intermediate and aminoacyl tRNA, each having been produced by misrecognition of an amino acid that would not be recognized if the aaRS were not altered, into an amino acid and an inorganic phosphoric acid and into an amino acid and tRNA, respectively. This is because an aaRS altered in terms of the amino acid it recognizes can be inhibited from misrecognizing the amino acid it recognized before alteration.

In fact, it is believed to be the most important and demanding task in producing an aaRS mutant that specifically recognizes an unnatural amino acid to inhibit the aaRS from recognizing the original substrate of the wild-type aaRS (tyrosine in the case of TyrRS) (Kiga et al., *PNAS* 99, 9715-9720, 2002; Summerer et al., *PNAS* 103, 9785-9789, 2006).

For example, in cases where the altered polypeptide is a TyrRS mutant, it is preferable to use a PheRS-derived editing polypeptide.

The PheRS is known to misrecognize tyrosine, which is similar to phenylalanine, i.e., the original substrate of the PheRS, to produce tyrosyl tRNA$^{Phe}$. The editing reaction domain of the PheRS has activity to hydrolyze an ester bond between tyrosine in tyrosyl tRNAPhe and tRNA into tyrosine and tRNA. Meanwhile, an altered polypeptide obtained by altering the TyrRS may misrecognize tyrosine, which is the original substrate. Introduction of the editing reaction domain of the PheRS into the TyrRS-derived altered polypeptide makes it possible to hydrolyze tyrosyl tRNA, which has been produced by misrecognition of tyrosine by the TyrRS-derived altered polypeptide, into tyrosine and tRNA. This makes it possible to prevent tyrosyl tRNA from being produced by misrecognition.

Further, in cases where the altered polypeptide is a MetRS mutant, it is preferable to use a LeuRS-derived editing polypeptide. The MetRS mutant may misrecognize methionine. Meanwhile, the LeuRS-derived editing polypeptide can hydrolyze binding of methionine to tRNA.

That is, in a preferred embodiment of the present invention, the altered polypeptide is a tyrosyl-tRNA synthetase altered so as to recognize an unnatural amino acid, and the editing polypeptide contained an editing reaction active site derived from a phenylalanyl-tRNA synthetase. Further, in a preferred embodiment of the present invention, the altered polypeptide is a methionyl-tRNA synthetase altered so as to recognize an unnatural amino acid, and the editing polypeptide contains an editing reaction active site derived from a leucyl-tRNA synthetase.

[1-5. Other Constituents of the Polypeptide According to the Present Invention]

The polypeptide according to the present invention may have a tag label (tag sequence) added To the N or C terminal thereof, for example, the tag label being a peptide that facilitates purification of the polypeptide. Such a sequence can be removed before the polypeptide is finally prepared. Examples of the tag sequence include a histidine tag, an HA tag, a Myc tag, and a Flag.

In one embodiment, it is preferable that the polypeptide according to the present invention be a polypeptide consisting of an amino-acid sequence represented by SEQ. ID. NO: 3.

Thus far, the constituents of the polypeptide according to the present invention have been described. In a preferred embodiment, it is preferable that the polypeptide according to the present invention be a polypeptide (i) consisting of an amino-acid sequence, represented by SEQ ID NO: 3 with a deletion, insertion, substitution, or addition of one or several amino acids, (ii) having editing reaction activity, and (iii) having activity to bind an unnatural amino acid to tRNA. SEQ ID NO: 3 is a amino-acid sequence of Ped-CP1-IYRS described below in Examples, and represents a polypeptide that exhibits the highest recognition specificity to 3-iodotyrosine.

It should be noted that a person skilled in the art can use a well-known technique to easily mutate one or several amino acids of the amino-acid sequence of the polypeptide. For example, according to a publicly-known point mutation introduction method (mutation induction method), a deletion mutant or an addition mutant can be produced by designing a primer corresponding to a given site in a polynucleotide coding for the polypeptide.

In one aspect, it is preferable that the polynucleotide according to the present invention code for the polypeptide having aminoacyl-tRNA synthetase activity.

The polynucleotide according to the present invention may be synthesized from a full-length polynucleotide by chemical synthesis, or may be synthesized by ligation of polynucleotides.

[1-6. Usage of the Polypeptide According to the Present Invention]

By introducing the polypeptide according to the present invention into a cell-free protein translation system, a *eubacterium*, or a eukaryotic cell (e.g., a yeast cell, a plant cell, an insect cell, and a mammalian cell) together with an unnatural amino acid, a protein containing the unnatural amino acid can be synthesized in the cell-free protein translation system, the *eubacterium*, or the eukaryotic cell.

<2. Method According to the Present Invention for Producing a Polypeptide>

A method according to the present invention for producing a polypeptide (hereinafter referred to simply as "production method according to the present invention") is a method for producing a polypeptide having aminoacyl-tRNA synthetase activity. The method includes: a preparing step of preparing a polynucleotide in which a polynucleotide coding for an editing polypeptide containing an editing reaction active site derived from a PheRS, a LeuRS, an IleRS, a ValRS, an AlaRS, a ProRS, or a ThrRS has been introduced into a polynucleotide coding for an altered polypeptide obtained by altering an ArgRS, a CysRS, a MetRS, a GlnRS, a GluRS, a LysRS, a TyrRS, or a TrpRS so that an unnatural amino acid is recognized; and an expressing step of expressing a polypeptide coded for by the polynucleotide obtained in the preparing step. In the preparing step, it is only necessary to prepare either a polynucleotide in which the editing polypeptide has been introduced so as to be positioned between a Rossman-fold N domain and a Rossman-fold C domain that exist in the altered polypeptide, or a polynucleotide in which the editing polypeptide has been introduced so as to be bound to an N terminal of the altered polypeptide.

[2-1. Preparing Step]

The preparing step that is carried out in the present invention is a step, included in the method for producing a polypeptide having aminoacyl-tRNA synthetase activity, in which to prepare a polynucleotide in which a polynucleotide coding for an editing polypeptide containing an editing reaction active site derived from a PheRS, a LeuRS, an IleRS, a ValRS, a AlaRS, a ProRS, or a ThrRS has been introduced into a polynucleotide coding for an altered polypeptide obtained by altering an ArgRS, a CysRS, a MetRS, a GlnRS, a GluRS, a LysRS, a TyrRS, or a TrpRS so that an unnatural amino acid is recognized, in which step (i) a polynucleotide in which the polynucleotide coding for the editing polypeptide has been introduced so as to be positioned between a Rossman-fold N domain and a Rossman-fold C domain in the polynucleotide coding for the altered polypeptide that recognizes the unnatural amino acid or (ii) a polynucleotide in which the editing polypeptide has been introduced so as to be bound to an N terminal of the altered polypeptide is prepared.

A person skilled in the art can use a well-known technique so that the polynucleotide coding for the editing polypeptide is introduced into a position corresponding to the space between a Rossman-fold N and C domains of the polynucleotide coding for the altered polypeptide or bound to a position corresponding to the N terminal of the altered polypeptide. For example, the polynucleotide coding for the editing polypeptide and the polynucleotide coding for the altered polypeptide can be bound with a ligase after being obtained by a nucleic-acid amplification reaction such as PCR.

There is no particular limit on a template for use in the nucleic-acid amplification reaction. However, it is possible to use a plasmid containing genome DNA, cDNA, and a clone of the polynucleotide. Further, it is possible to bind fragments cut out from the plasmid by restriction enzyme digestion. Further, as will be described below in Examples, it is possible to prepare a template by overlap PCR. Further, it is possible to chemically synthesize a full-length polynucleotide of the polynucleotide coding for the editing polypeptide and the polynucleotide coding for the altered polypeptide.

[2-2. Expressing Step]

Use of the polynucleotide obtained in the preparing step makes it possible to transform eubacteria such as *Escherichia coli* or eukaryotic cells (e.g., yeast cells, plant cells, insect cells, and mammalian cells) and express, in the transformed cells, a polypeptide coded for by the polynucleotide obtained in the preparing step. Further, it is possible to perform transcription and protein synthesis in a conventionally publicly-known rabbit reticulocyte, insect, or wheat cell-free system.

The polynucleotide obtained in the preparing step can be incorporated into an expression vector. There is no particular limit on the specific type of vector, and it is possible to appropriately select a vector capable of expression in a host cell for use in expression. That is, it is only necessary to select, according to the type of host cell, an appropriate promoter sequence for surely expressing a polypeptide coded for by the polynucleotide according to the present invention and use, as an expression vector, a vector obtained by incorporating the promoter sequence and the polynucleotide according to the present invention into various plasmids. It should be noted that the vector is not limited to a case where the objective protein is constitutively synthesized, but may be induced by addition of IPTG to be synthesized. Further, the vector may include a sequence that adds a tag sequence such as a histidine tag, an HA tag, a Myc tag, or a Flag to the N or C terminal of the protein to be synthesized.

After a host transformed with use of the expression vector is cultured, the objective protein can be collected from the culture or the like and purified according to a conventional technique (e.g., filtration, centrifugation, cell breakage, gel filtration chromatography, ion-exchange chromatography). Further, in cases where the tag has been added to the protein to be synthesized, the objective protein can be easily collected.

It is preferable that the expression vector include at least one selective marker. As for eukaryotic cell culture, an example of such a marker is a dihydrofolate reductase or a drug-resistant gene such as neomycin, zeocin, geneticin, blasticidin S, or hygromycin B. As for culture of *Escherichia coli* and other bacteria, an example of such a marker is a drug-resistant gene such as kanamycin, zeocin, actinomycin D, cefotaxime, streptomycin carbenicillin, puromycin, tetracycline, or ampicillin.

Use of the selective marker makes it possible to confirm whether or not the polynucleotide according to the present invention has been introduced into a host cell, and to further confirm whether or not the polynucleotide according to the present invention has been surely expressed in the host cell.

The host cell is not particularly limited, and can be suitably realized by various conventional publicly-known cells.

The method for introducing a polynucleotide according to the present invention or an expression vector including a polynucleotide according to the present invention into a host cell, i.e., the transformation method is not particularly limited, and can be suitably realized by a conventional publicly-known method such as electroporation or a calcium-phosphate method.

The embodiments of the present invention will be further detailed below with reference to examples. The present invention is not limited to the following examples, and details of the present invention can take various aspects. Furthermore, the present invention is not limited to the description of the embodiments above, but may be altered by a skilled person within the scope of the claims. An embodiment based on a proper combination of technical means disclosed in different embodiments is encompassed in the technical scope of the present invention. Further, all the documents cited in this specification can be cited as references.

EXAMPLE 1

Construction of Editing Reaction Peptide Expression Plasmids

As mentioned above, the beta-subunit of PheRS consists of B1, B2, B3/4, B5, B6/7, and B8 domains, and the B3/4 domain is an editing reaction domain.

In the beta-subunit of PheRS, the B6/7 and B8 domains is placed separately from the B3/4 domain because of the three-dimensional structure. Further, it is believed that there is no fixed structure formed between the B5 domain and the B6/7 domain.

In view of this, the present example uses, as an editing polypeptide, a polypeptide fragment (hereinafter referred to as "editing reaction peptide") including the B3/4 domain, and as such, does not include the B6/7 domain and the B8 domain.

With use of the genome DNA of E. coli, the genome DNA of T. thermophilus, and the genome DNA of P. horikoshii as templates, a DNA fragment coding for the B1 to B5 domains (B1-B5) of the beta-subunit of PheRS of each living organism, a DNA fragment coding for the B1 to B3/4 domains (B1-B3/4) of the beta-subunit, a DNA fragment coding for the B3/4 to B5 domains (B3/4-B5) of the beta-subunit, and a DNA fragment coding for only the B3/4 domain of the beta-subunit were amplified by PCR.

Specifically, the 1st to 475th amino-acid residues of the amino-acid sequence of the beta-subunit of PheRS of E. coli, the 1st to 403rd amino-acid residues of the amino-acid sequence, the 188th to 475th amino-acid residues of the amino-acid sequence, and the 188th to 403rd amino-acid residues of the amino-acid sequence were used as B1-B5, B1-B3/4, B3/4-B5, and B3/4, respectively. The amino-acid sequence is represented by SEQ. ID. NO: 52.

As for PheRS of T. thermophilus, the 1st to 473rd amino-acid residues of the amino-acid sequence of the beta-subunit of PheRS of T. thermophilus, the 1st to 401st amino-acid residues of the amino-acid sequence, the 190th to 473rd amino-acid residues of the amino-acid sequence, and the 190th to 401st amino-acid residues of the amino-acid sequence were used as B1-B5, B1-B3/4, B3/4-B5, and B3/4, respectively. The amino-acid sequence is represented by SEQ. ID. NO: 53.

As for PheRS of P. horikoshii, the 1st to 353rd amino-acid residues of the amino-acid sequence of the beta-subunit of PheRS of P. horikoshii, the 1st to 280th amino-acid residues of the amino-acid sequence, the 83rd to 353rd amino-acid residues of the amino-acid sequence, and the 83rd to 280th amino-acid residues of the amino-acid sequence were used as B1-B5, B1-B3/4, B3/4-B5, and B3/4, respectively. The amino-acid sequence is represented by SEQ. ID. NO: 54.

The DNA fragments coding for their respective domains of E. coli were amplified as follows. Specifically, the DNA fragment coding for B1-B5 was amplified by PCR with use of primers Ec-B1-F (SEQ. ID. NO: 55) and Ec-B5-R (SEQ. ID. NO: 56). The DNA fragment coding for B1-B3/4 was amplified by PCR with use of primers Ec-B1-F and Ec-B3/4-R (SEQ. ID. NO: 57). The DNA fragment coding for B3/4-B5 was amplified by PCR with use of primers Ec-B3/4-F (SEQ. ID. NO: 58) and Ec-B5-R. The DNA fragment coding for B3/4 was amplified by PCR with use of primers Ec-B3/4-F and Ec-B3/4-R.

The DNA fragments coding for their respective domains of T. thermophilus were amplified as follows. Specifically, the DNA fragment coding for B1-B5 was amplified by PCR with use of primers Tt-B1-F (SEQ. ID. NO: 59) and Tt-B5-R (SEQ. ID. NO: 60). The DNA fragment coding for B1-B3/4 was amplified by PCR with use of primers Tt-B1-F and Tt-B3/4-R (SEQ. ID. NO: 61). The DNA fragment coding for B3/4-B5 was amplified by PCR with use of primers Tt-B3/4-F (SEQ. ID. NO: 62) and Tt-B5-R. The DNA fragment coding for B3/4 was by PCR amplified with use of primers Tt-B3/4-F and Tt-B3/4-R.

The DNA fragments coding for their respective domains of P. horikoshii were amplified as follows. Specifically, the DNA fragment coding for B1-B5 was amplified by PCR with use of primers Ph-B1-F (SEQ. ID. NO: 63) and Ph-B5-R (SEQ. ID. NO: 64). The DNA fragment coding for B1-B3/4 was amplified by PCR with use of primers Ph-B1-F and Ph-B3/4-R (SEQ. ID. NO: 65). The DNA fragment coding for B3/4-B5 was amplified by PCR with use of primers Ph-B3/4-F (SEQ. ID. NO: 66) and Ph-B5-R. The DNA fragment coding for B3/4 was amplified by PCR with use of primers Ph-B3/4-F and Ph-B3/4-R.

In each case, PCR was carried out under the following thermocycling conditions: 98° C. for 1 minute; 98° C. for 10 seconds, 54° C. for 30 seconds, and 72° C. for 1 minute (25 cycles). The DNA polymerase used was Phusion High-Fidelity DNA Polymerase (NEB, Inc.).

Each of the DNA fragments thus amplified was introduced between the NdeI and XhoI sites of a vector pET-26b (Novagen, Inc.) so that His-tag was added to the C terminal of the polypeptide to be expressed. Thus produced was an editing reaction peptide expression plasmid. The editing reaction peptide expression plasmid was cloned.

EXAMPLE 2

Expression and Purification of Editing Reaction Peptides

With use of each of the expression plasmids thus cloned, Escherichia coli BL21 Star (DE3) (Invitrogen Corporation) was transformed, and then cultured at 37° C. in an LB medium containing 50 µg/ml of kanamycin. At the point of time where the O. D. 600 of the culture fluid took on a value of 0.4 to 0.6, IPTG was added so that the final concentration was 1 mM. After the addition of IPTG, the culture temperature was lowered to 20° C. In this manner, the expression of each editing reaction peptide was induced. Twenty hours after the start of induction, the bacteria were harvested.

Next, the editing reaction peptide was extracted from the bacteria thus harvested, and purified. A lytic buffer solution was prepared by adding a grain of a protease inhibitor cOmplete (Roche) to 200 ml of a buffer solution A (20 mM Tris-Cl (ph 8.0), 300 mM NaCl, 30 mM imidazole, 5 mM 2-mercaptoethenol). The harvested bacteria were suspended in the lytic buffer solution, and then were subjected to sonication. An insoluble fraction was precipitated by centrifugation. Each editing reaction peptide, contained in a supernatant, was adsorbed to a resin Ni Sepharose 6 Fast Flow (GE Healthcare, Inc.) equilibrated with use of the lytic buffer solution. After the resin had been washed with the lytic buffer solution, the editing reaction peptide was eluted from the resin with use of a buffer solution B obtained by increasing the imidazole concentration of the buffer solution A to 500 mM.

The eluate was diluted with use of 20 mM Tris-Cl (ph 8.0) so that the concentrations of Tris-Cl, NaCl, and imidazole in the eluate became 20 mM Tris-C1 (ph 8.0), 75 mM NaCl, and 125 mM imidazole. As for the eluate thus diluted, a protein was concentrated with use of Amicon-Ultra 4 (Millipore Corporation) until the volume became approximately 100 µl. The concentrated protein was put with glycerol so that the final concentration became 50%, mixed well, and preserved at −20° C.

The twelve types of editing reaction peptide thus obtained varied slightly in expression level, depending on the types of living organism, but were expressed so that soluble fractions were generally obtained. Further, none of them aggregated when concentrated.

EXAMPLE 3

Hydrolysis Activity of the Editing Reaction Peptides

Next, the hydrolysis activity of each of the editing reaction peptides was measured. The measurement of the hydrolysis activity of each of the editing reaction peptides was performed by measuring the extent to which tyrosylation of tRNA$^{Tyr}$ by EcIYRS was inhibited, instead of directly measuring hydrolysis in tyrosyl tRNA$^{Tyr}$. EcIYRS was obtained in the following manner. That is, a pET-26b-derived plasmid (donated from Dr. Kobayashi of RIKEN) cloned so that Histag sticks to the C terminal of EcIYRS was used to transform *Escherichia coli* BL21 Star (DE3) (Invitrogen Corporation) The subsequent operations were performed in the same manner as in the aforementioned expression and purification of editing reaction peptides.

It should be noted that the base sequence of EcIYRS is represented by SEQ. ID. NO: 4. It should also be noted that the amino-acid sequence of EcIYRS is an amino-acid sequence represented by the aforementioned SEQ. ID. NO: 1.

A reaction solution was prepared in an amount of 20 μl by adding 200 μM tyrosine, 1 μM EcIYRS, and 2.5 μM editing reaction peptide to an aminoacylation buffer solution (100 mM Tris-Cl (pH 7.5), 15 mM MgCl$_2$, 5 μM tRNA$^{Tyr}$, 4 mM ATP). The reaction solution was incubated at 37° C. for 25 minutes. The reaction was terminated by adding, to the reaction solution, an equal volume of a solution containing 300 mM sodium acetate (pH 5.0), 8 M urea, 0.05% bromophenol blue, and 0.05% xylene cyanol. Next, the reaction solution was subjected to electrophoresis (urea-denatured acidic PAGE) with use of M urea denatured 7% (w/v) polyacrylamide gel (acrylamide: bisacrylamide=29:1) equilibrated with 0.1 M sodium acetate (pH 5.0). The electrophoretic buffer solution used was 0.1 M sodium acetate (pH 5.0). The electrophoresis was performed for 10 to 14 hours under the following conditions: a temperature of 4° C.; and a current of 24 to 30 mA. After the electrophoresis, tRNA was detected by staining the gel with toluidine blue.

FIG. 1 shows the results of electrophoresis. (a) to (c) of FIG. 1 show that with no addition of editing reaction peptides, EcIYRS tyrosylated tRNA$^{Tyr}$ and the bands of tRNA shifted almost completely (Lanes 2). From this, it can be judged that the decreases in shift of bands at the time of addition of the editing reaction peptides are attributed to the hydrolyses caused by the editing reaction peptides.

As for the case of addition of the *E. coli*-derived editing peptides, remarkable decreases in shift of bands were observed in the case of addition of the B1-B3/4, B3/4-B5, and B3/4 editing reaction peptides (Lanes 4, 5, and 6 of FIG. 1(a)). As for the case of addition of the *T. thermophilus* editing reaction peptides, a decrease in shift of a band was observed in the case of addition of the B1-B3/4 editing reaction peptide (Lane 4 of FIG. 1(b)). As for the case of addition of the *P. horikoshii* editing reaction peptides, decreases in shift of bands were observed in the case of addition of the B1-B5 and B3/4 editing reaction peptides (Lanes 3 and 6 of FIG. 1(c)).

These results show that a polypeptide fragment including a B3/4 domain retains hydrolysis activity even if it is not a full-length protein. As for the *E. coli*- and *P. horikoshii*-derived editing reaction peptides, even the shortest editing reaction peptides retain hydrolysis activity.

Meanwhile, in the case of *T. thermophilus*, extremely satisfactory hydrolysis activity was exhibited in the case of use of the B1-B3/4, to which the B1 and B2 domains had been added, in comparison with the B3/4.

EXAMPLE 4

Construction of N-terminal Fusion Protein Expression Plasmids

Plasmids for expressing fusion proteins each having an editing reaction peptide introduced at the N terminal of EcIYRS were constructed.

Among the *E. coli*-, *P. horikoshii*-, and *T. thermophilus*-derived editing reaction peptides, the smallest editing reaction peptide was fused with the N terminal of EcIYRS. That is, as for each of the *E. coli* and *P. horikoshii* editing reaction peptides, the editing reaction domain B3/4 was used. As for the *T. thermophilus* editing reaction peptide, the editing reaction domain B1-B3/4 was used.

It should be noted that the amino-acid sequence of the *E. coli*-derived B3/4 domain is represented by SEQ. ID. NO: 5 and the base sequence is represented by SEQ. ID. NO: 6. The amino-acid sequence of the *P. horikoshii*-derived B3/4 domain is represented by SEQ. ID. NO: 2 and the base sequence is represented by SEQ. ID. NO: 7. The amino-acid sequence of the *T. thermophilus*-derived B1-B3/4 domain is represented by SEQ. ID. NO: 8 and the base sequence is represented by SEQ. ID. NO: 9.

Figure 2:
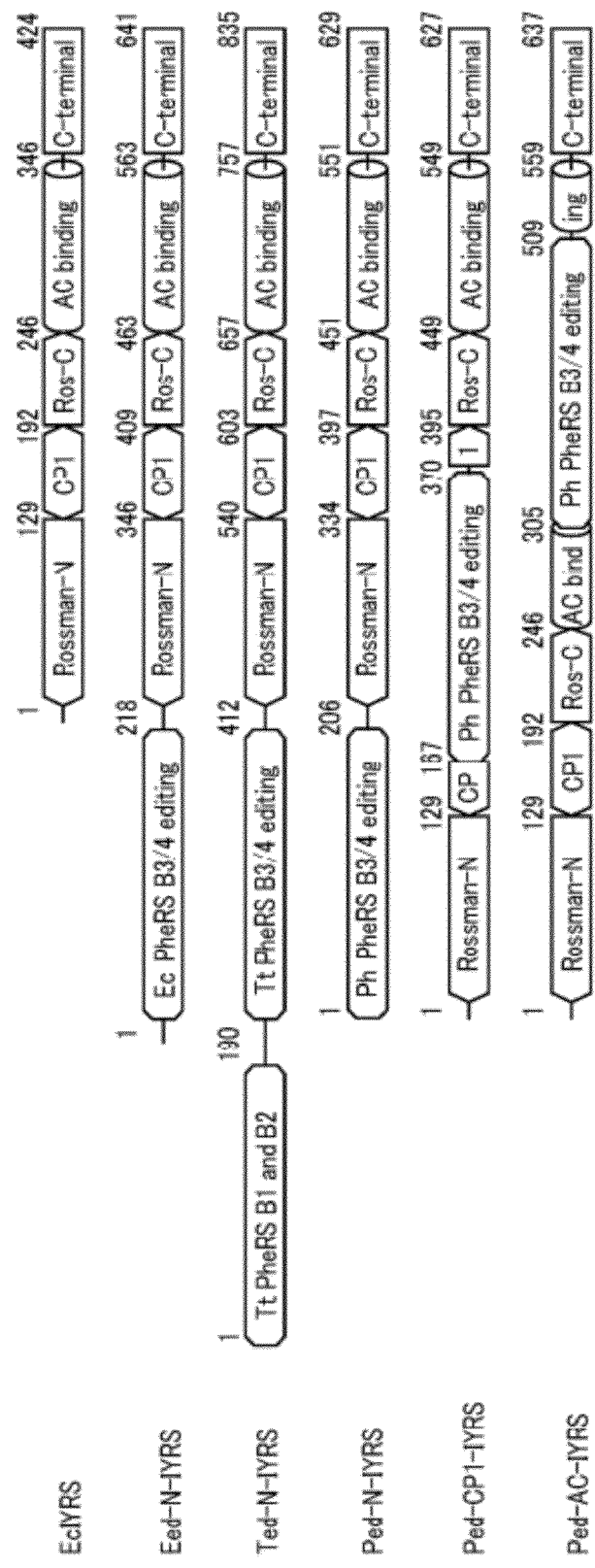
FIG. 2, showing an embodiment of the present invention, schematically shows the structures of fusion proteins.

It should be noted that the mutants are named "Eed-N-IYRS" (*E. coli*), "Ted-N-IYRS" (*T. thermophilus*), and "Ped-N-IYRS" (*P. horikoshii*) after the original species and sites of fusion of the editing reaction domains. FIG. 2 schematically shows the constituents of each of the fusion proteins.

Further, from each of the fusion proteins, a mutant was produced by inactivating the editing reaction activity of the fusion protein (Eed$^{mu}$-N-IYRS, Ted$^{mu}$-N-IYRS, and Ped$^{mu}$-N-IYRS). In each of Eed$^{mu}$-N-IYRS and Ted$^{mu}$-N-IYRS, Ala356 in the original PheRS beta-subunit had been substituted with Trp. In Ped$^{mu}$-N-IYRS, Ala141 in the original PheRS beta-subunit had been substituted with Trp. These two types of amino-acid residue are structurally at substantially the same location. The mutation causes Trp to be embedded in a substrate-binding pocket, with the result that the editing reaction activity is lost.

The mutation that inactivates editing reaction was introduced site-specifically by amplifying the whole plasmid by PCR. The Eed$^{mu}$-N-IYRS expression plasmid was produced with use of the Eed-N-IYRS expression plasmid as a template by amplifying the whole plasmid by PCR with use of primers Ec-Mu-F (SEQ. ID. NO: 67) and Ec-Mu-R (SEQ. ID. NO: 68). Further, the Ted$^{mu}$-N-IYRS expression plasmid was produced with use of the Ted-N-IYRS expression plasmid as a template by amplifying the whole plasmid by PCR with use of primers Tt-Mu-F (SEQ. ID. NO: 69) and Tt-Mu-R (SEQ. ID. NO: 70). The Ped$^{mu}$-N-IYRS expression plasmid was produced with use of the Ped-N-IYRS expression plasmid as a template by amplifying the whole plasmid by PCR with use of primers Ph-Mu-F (SEQ. ID. NO: 71) and Ph-Mu-R (SEQ. ID. NO: 72). In each case, PCR was carried out under the following thermocycling conditions: 98° C. for 1 minute; 98° C. for 10 seconds, 54° C. for 30 seconds, and 72° C. for 2 minutes and 30 seconds (16 cycles). The DNA polymerase used was Phusion High-Fidelity DNA Polymerase.

With use of the genome DNA of *E. coli* as a template, DNA coding for the B3/4 domain of *E. coli* was amplified by PCR with use of primers EcN1 (SEQ. ID. NO: 15) and EcN2 (SEQ. ID. NO: 16). PCR was carried out under the following thermocycling conditions: 98° C. for 1 minute; 98° C. for 10 seconds, 54° C. for 30 seconds, and 72° C. for 1 minute (25 cycles). After the last cycle, the reacted solution was preserved at 72° C. for 5 minutes.

With use as a template of a plasmid A (donated from Dr. Kobayashi of RIKEN) containing DNA coding for EcIYRS, the DNA coding for EcIYRS was amplified by PCR with use of primers EcN3 (SEQ. ID. NO: 17) and EcN4 (SEQ. ID. NO: 18). PCR was carried out under the same thermocycling conditions as the DNA coding for the B3/4 domain of *E. coli* had been amplified.

Next, a DNA fragment coding for a fusion protein in which the B3/4 domain of the *E. coli* PheRS beta-subunit had been added to the N terminal of the EcIYRS protein was amplified by overlap PCR with use of the PCR-amplified DNA coding for the B3/4 domain of *E. coli*, the PCR-amplified DNA coding for EcIYRS, and primers EcN5 (SEQ. ID. NO: 19) and EcN6 (SEQ. ID. NO: 20). First, a reaction solution containing neither of the primers EcN5 and EcN6 was prepared. With use of this reaction solution, PCR was carried out under the following thermocycling conditions: 98° C. for 1 minute; 98° C. for 10 seconds, 57° C. for 30 seconds, and 72° C. for 1 minute (8 cycles). After the 8 cycles, the primers EcN5 and EcN6 were added to the reaction solution. With use of the reaction solution to which the primers had been added, PCR was carried out under the following thermocycling conditions: 98° C. for 1 minute; 98° C. for 10 seconds, 57° C. for 30 seconds, and 72° C. for 1 minute 45 seconds (26 cycles). After the last cycle, the reacted solution was preserved at 72° C. for 5 minutes. The amplified DNA was inserted between the NdeI and XhoI sites of an expression vector pET-26b (Novagen, Inc.) so that a His tag was added. Thus produced was an Eed-N-IYRS expression plasmid. The base sequence of Eed-N-IYRS is represented by SEQ. ID. NO: 10.

With use of the genome DNA of *T. thermophilus*, DNA coding for the B1-B3/4 domain of *T. thermophilus* was amplified by PCR with use of primers TtN1 (SEQ. ID. NO: 21) and TtN2 (SEQ. ID. NO: 22). PCR was carried out under the following thermocycling conditions: 98° C. for 1 minute; 98° C. for 10 seconds, 72.2° C. for 30 seconds, and 72° C. for 1 minute (25 cycles). After the last cycle, the reacted solution was preserved at 72° C. for 5 minutes.

With use of the plasmid A as a template, DNA coding for EcIYRS was amplified by PCR with use of primers TtN3 (SEQ. ID. NO: 23) and TtN4 (SEQ. ID. NO: 24).

Next, a DNA fragment coding for a fusion protein in which the B3/4 domain of the *T. thermophilus* had been added to the N terminal of the EcIYRS protein was amplified by overlap PCR with use of the PCR-amplified DNA coding for the B1-B3/4 domain of *T. thermophilus*, the PCR-amplified DNA coding for EcIYRS, and primers TtN5 (SEQ. ID. NO: 25) and TtN6 (SEQ. ID. NO: 26). First, a reaction solution containing neither of the primers TtN5 and TtN6 was prepared. With use of this reaction solution, PCR was carried out. The reaction was paused. The primers TtN5 and TtN6 were added. The reaction was resumed. The specific conditions for overlap PCR were the same as those under which the DNA coding for Eed-N-IYRS had been prepared. The amplified DNA was inserted between the NdeI and XhoI sites of a vector pET-26b (Novagen, Inc.) so that a His tag was added. Thus produced was a Ted-N-IYRS expression plasmid. The base sequence of Ted-N-IYRS is represented by SEQ. ID. NO: 11.

With use of the genome DNA of *P. horikoshii* as a template, DNA coding for the B3/4 domain of *P. horikoshii* was amplified by PCR with use of primers PhN1 (SEQ. ID. NO: 27) and PhN2 (SEQ. ID. NO: 28). PCR was carried out under the following thermocycling conditions: 98° C. for 1 minute; 98° C. for 10 seconds, 57° C. for 30 seconds, and 72° C. for 1 minute (25 cycles). After the last cycle, the reacted solution was preserved at 72° C. for 5 minutes.

With use of the plasmid A as a template, DNA coding for EcIYRS was amplified by PCR with use of primers PhN3 (SEQ. ID. NO: 29) and PhN4 (SEQ. ID. NO: 30).

Next, a DNA fragment coding for a fusion protein in which the B3/4 domain of the *P. horikoshii* had been added to the N terminal of the EcIYRS protein was amplified by overlap PCR with use of the PCR-amplified DNA coding for the B3/4 domain of *P. horikoshii*, the PCR-amplified DNA coding for EcIYRS, and primers PhN5 (SEQ. ID. NO: 31) and PhN6 (SEQ. ID. NO: 32). First, a reaction solution containing neither of the primers PhN5 and PhN6 was prepared. With use of this reaction solution, PCR was carried out under the following thermocycling conditions: 98° C. for 1 minute; 98° C. for 10 seconds, 57° C. for 30 seconds, and 72° C. for 1 minute (8 cycles). After the 8 cycles, the primers PhN5 and PhN6 were added to the reaction solution. With use of the reaction solution to which the primers had been added, PCR was carried out under the following thermocycling conditions: 98° C. for 1 minute; 98° C. for 10 seconds, 57° C. for 30 seconds, and 72° C. for 1 minute (25 cycles). After the last cycle, the reacted solution was preserved at 72° C. for 5 minutes. The amplified DNA was inserted between the NdeI and XhoI sites of an expression vector pET-26b (Novagen, Inc.) so that a His tag was added. Thus produced was a Ped-N-IYRS expression plasmid. The base sequence of Ped-N-IYRS is represented by SEQ. ID. NO: 12.

In the PCR of the present example, including the aftermentioned PCR, the polymerase used was Phusion High-Fidelity DNA Polymerase (NEB, Inc.).

The expression and purification of each fusion protein were performed in the same manner as in Example 2, except that the culture temperature conditions after the induction of expression were changed to 24° C. Further, the expression was confirmed by SDS-PAGE (not shown).

EXAMPLE 5

Determination of the Aminoacylation Activity of the N-terminal Fusion Proteins

Next, the aminoacylation activity (tyrosylation activity) of each of the fusion proteins was determined. An aminoacylation reaction solution was prepared by adding 30 μM [$^{14}$C]-L-tyrosine (GE Healthcare) and 1 μM aaRS to an aminoacylation buffer solution. By incubating the reaction solution at 37° C., aminoacylation was performed, with the result that [$^{14}$C]-L-tyrosyl tRNA$^{Tyr}$ was produced. [$^{14}$C]L-tyrosyl tRNA$^{Tyr}$ was precipitated on a piece of filter paper with 10% trichloroacetic acid (TCA). After the piece of filter paper had been washed with 5% TCA and 100% ethanol, the radioactivity of the piece of filter paper was measured by a liquid scintillation counter. Since the piece of filter paper adsorbs only a high-molecular substance, unreacted [$^{14}$C]-tyrosine is washed away, so that only tyrosylated tRNA, i.e., [$^{14}$C]-tyrosyl tRNA$^{Tyr}$ can be measured. Such radioactivity was used to determine the extent to which each fusion protein recognized tyrosine.

Figure 3:
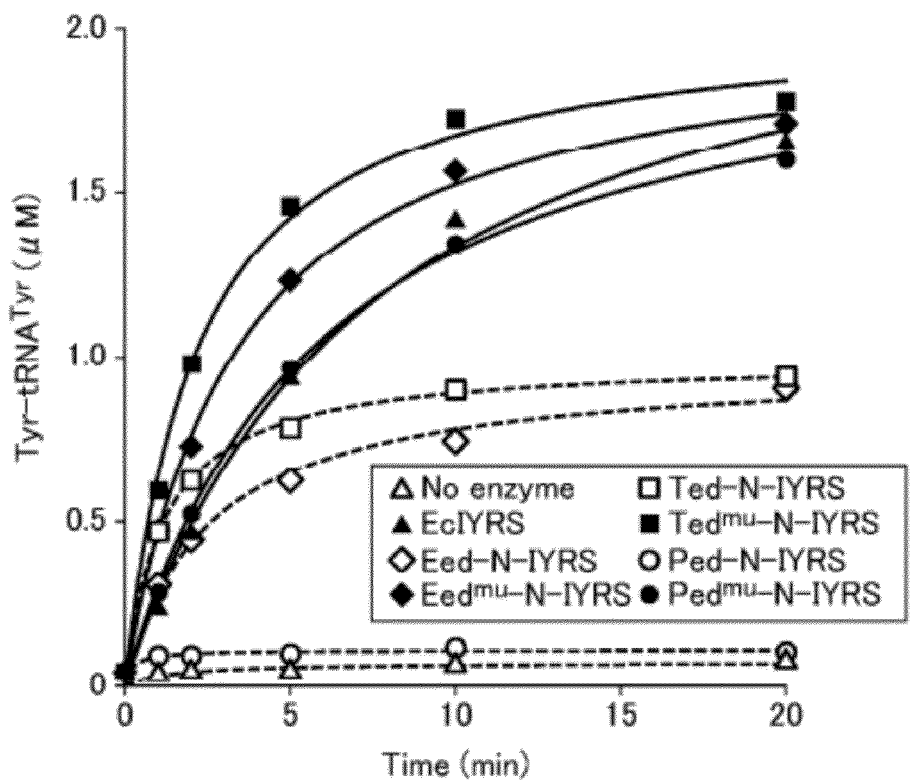
FIG. 3, showing an embodiment of the present invention, shows the hydrolysis activity of fusion proteins.

FIG. 3 shows the results of determination of recognition of tyrosine. As shown in FIG. 3, the mutants, in each of which an altered editing reaction domain obtained by inactivating the editing reaction activity of an editing reaction domain had been added to the N terminal, maintained the same level of tyrosylation activity as EcIYRS, regardless of the species of editing reaction domain with which the mutants had been fused. This shows that the tyrosylation activity of EcIYRS is hardly lowered due to the fusion of an exogenous sequence with the N terminal. Therefore, it can be said that the decreases in tyrosylation activity at the time of fusion of the wild-type editing reaction domains are attributed to the hydrolyses caused by the editing reactions.

A certain level of decrease in tyrosylation was seen regardless of the species of editing reaction domain fused. In each of the cases where the editing reaction domains of bacteria *E. coli* and *T. thermophilus* were added, it was confirmed that the amount of [$^{14}$C]-tyrosyl tRNA$^{Tyr}$ detected was half as large as in the case where EcIYRS was used. That is, it was confirmed that the activity was half as high as that of EcIYRS. Further, in the case where the editing reaction domains of archaebacteria *P. horikoshii* was added, it was confirmed that [$^{14}$C]-tyrosyl tRNA$^{Tyr}$ was hardly detected and the tyrosylation of tRNA$^{Tyr}$ was inhibited.

Next, each of the fusion proteins was assayed for substrate specificity. A reaction solution was prepared by adding 200 µM tyrosine or 3-iodotyrosine and 1 µM fusion protein to an aminoacylation buffer solution. The reaction solution was incubated at 24° C. for 30 minutes. The reaction was terminated by adding, to the reaction solution, an equal volume of a solution containing 300 mM sodium acetate (pH 5.0), 8 M urea, 0.05% bromophenol blue, and 0.05% xylene cyanol. The reaction solution was subjected to urea-denatured acidic PAGE in the same manner as in the aforementioned determination of the hydrolysis activity of the editing reaction peptides, whereby a shift in band of tRNA was observed. The assay makes it possible to confirm whether or not 3-iodotyrosine is recognized.

Figure 4:
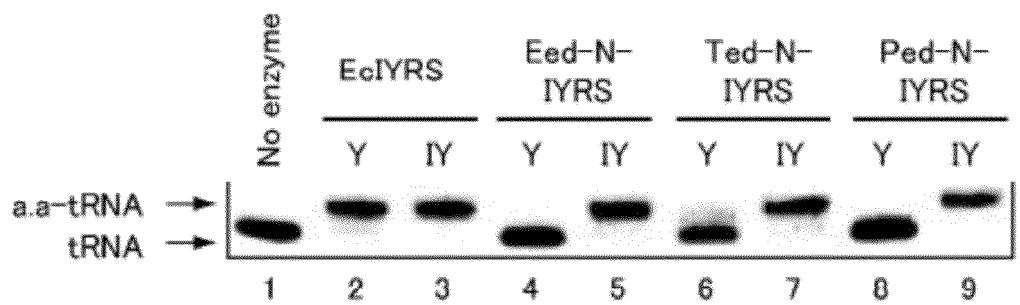
FIG. 4, showing an embodiment of the present invention, shows the substrate recognition specificity of fusion proteins.

FIG. 4 shows the results of assaying the fusion proteins for their substrate specificity. As shown in FIG. 4, Eed-N-IYRS, Ted-N-IYRS, and Ped-N-IYRS showed no band shifts in cases where tyrosine was used (Lanes 4, 6, and 8), but showed band shifts in cases where iodotyrosine was used (Lanes 5, 7, and 9). In contrast, EcIYRS, which does not contain an editing reaction domain, showed a band shift also in cases where tyrosine was used (Lane 2). This shows that an editing reaction domain does not hydrolyze 3-iodotyrosyl tRNA$^{Tyr}$ and only tyrosyl tRNA is recognized and hydrolyzed by using an editing reaction domain.

EXAMPLE 6

Search for a Place to Insert an Editing Reaction Domain

The aaRSs classified into class I share a common basic structure, i.e., a Rossman-fold domain, and each of the aaRSs further has an additional domain inserted at the N terminal of the Rossman-fold domain, at the C terminal of the Rossman-fold domain, or into the Rossman-fold domain. Locations where these insertion sequences exist are considered to be places where another sequence can be inserted without disarraying the Rossman-fold structure.

The amino-acid sequences of the 2,467 types of class I aaRS registered in Swiss-prot were aligned. The software used for alignment was MAFFT (Katoh, K., Misawa, K., Kuma, K., and Miyata T., MAFFT: a novel method for rapid multiple sequence alignment based on fast Fourier transform. *Nucleic Acids Res*, 2002, 30, 3059-3066; Katoh, K., Kuma, K., Toh, H., and Miyata, T., MAFFT version 5: improvement in accuracy of multiple sequence alignment. *Nucleic Acids Res*, 2005, 33, 511-518).

As a result of alignment of the primary sequences of the class I aaRSs, each of the class I aaRSs showed some characteristic insertion sequences. Among those insertion sequences, the most remarkable insertion sequences were the CP1 domains of ValRS, IleRS, and LeuRS. In ValRS, IleRS, and LeuRS, the CP1 domains were editing reaction domains.

A CP1 domain is an insertion sequence that every class I aaRS has inside of the Rossman fold. Each of the class I aaRSs has a CP1 domain inserted at the same site in the Rossman fold as the other. CP1 domains vary in length and function from aaRS to aaRS. The three CP1 domains of ValRS, IleRS, and LeuRS are the longest, i.e., as long as approximately 200 amino-acid residues, and serve as editing reaction domains. Meanwhile, the CP1 domain of TyrRS is as short as approximately 70 amino-acid residues. The CP1 domain of TyrRS involves in tRNA recognition, dimerization, and substrate recognition. In this alignment, the editing reaction domains of ValRS, IleRS, and LeuRS were inserted between the 166th and 167th resides of a loop domain (163rd to 169th amino-acid residues) that exists in the CP1 domain of TyrRS. This loop is not in contact with any other domain in the CP1 domain, and as such, has no particular function. Therefore, it was supposed that the structure of EcIYRS would not be disarrayed even if an editing reaction domain was inserted. In view of this, it was decided that the editing reaction domain of PheRS was inserted into the loop domain.

The editing reaction domain was realized by a *P. horikoshii*-derived editing reaction domain. The resultant EcIYRS mutant is named "Ped-CP1-IYRS" after the place where the editing reaction domain has been inserted. That is, the editing reaction domain has been inserted in the CP1 domain of Ped-CP1-IYRS.

For comparison, the following discusses an EcIYRS mutant obtained by inserting the editing reaction domain into the AC binding domain. The EcIYRS mutant is hereinafter referred to as "Ped-AC-IYRS".

FIG. 2 schematically shows the constituents of each of these fusion proteins. For ease of comparison, FIG. 2 also shows EcIYRS and the fusion proteins produced in Example 4.

EXAMPLE 7

Construction of a Ped-CP1-IYRS Expression Plasmid

With use of the genome DNA of *P. horikoshii* as a template, DNA coding for the B3/4 domain of *P. horikoshii* was amplified by PCR with use of primers PhC1 (SEQ. ID. NO: 33) and PhC2 (SEQ. ID. NO: 34). PCR was carried out under the following thermocycling conditions: 98° C. for 1 minute; 98° C. for 10 seconds, 55° C. for 30 seconds, and 72° C. for 1 minute (25 cycles). After the last cycle, the reacted solution was preserved at 72° C. for 2 minutes.

With use of the plasmid A as a template, DNA coding for the first to 166th amino-acid residues of EcIYRS and DNA coding for the 167th to 424th amino-acid residues of EcIYRS were amplified by PCR with use of primers PhC3 (SEQ. ID. NO: 35) and PhC4 (SEQ. ID. NO: 36) and by PCR with use of primers PhC5 (SEQ. ID. NO: 37) and PhC6 (SEQ. ID. NO: 38).

Next, a DNA fragment coding for a fusion protein in which the B3/4 domain of *P. horikoshii* had been inserted into the CP1 domain of EcIYRS was amplified by PCR with use of the PCR-amplified DNA coding for the B3/4 domain of *P. horikoshii*, the PCR-amplified DNA coding for the N (1-166) and C (167-424) terminals of EcIYRS, and primers PhC7 (SEQ. ID. NO: 39) and PhC8 (SEQ. ID. NO: 40). A reaction solution containing the N-terminal DNA, the C-terminal DNA, and the primers PhC7 and PhC8 was prepared. The reaction solution was subjected to PCR under the following thermocycling conditions: 98° C. for 1 minute; 98° C. for 10 seconds, 52° C. for 30 seconds, and 72° C. for 1 minute and 10 seconds (25 cycles). After the last cycle, the reacted solution was preserved at 72° C. for 2 minutes.

The amplified DNA was cloned between the NdeI and XhoI sites of an expression vector pET-26b so that a His tag is added to the C terminal. Thus produced was a Ped-CP1-IYRS expression plasmid. The base sequence of Ped-CP1-IYRS is represented by SEQ. ID. NO: 13.

The mutation that inactivates editing reaction was introduced site-specifically by amplifying the whole plasmid by PCR.

The expression and purification of the Ped-CP1-IYRS protein were performed in the same manner as in Example 4. Further, the expression was confirmed by SDS-PAGE (not shown).

It should be noted that the mutant with inactivated editing activity was produced in the same manner (Ped$^{mu}$-CP1-IYRS). The mutation that inactivates the editing reaction domain is the same as in the case of Ped$^{mu}$-N-IYRS described in Example 4. The Ped$^{mu}$-CP1-IYRS expression plasmid was produced in the same manner as Ped$^{mu}$-N-IYRS described in Example 4, except that Ped-CP1-IYRS was used as a template instead.

COMPARATIVE EXAMPLE 1

Construction of a Ped-AC-IYRS Expression Plasmid

With use of the genome DNA of *P. horikoshii* as a template, DNA coding for the B3/4 domain of *P. horikoshii* was amplified by PCR with use of primers PhA1 (SEQ. ID. NO: 41) and PhA2 (SEQ. ID. NO: 42). The PCR was carried out under the following thermocycling conditions: 98° C. for 1 minute; 98° C. for 10 seconds, 55° C. for 30 seconds, and 72° C. for 1 minute (25 cycles). After the last cycle, the reacted solution was preserved at 72° C. for 2 minutes.

With use of the plasmid A as a template, DNA coding for the first to 304th amino-acid residues of EcIYRS and DNA coding for the 305th to 424th amino-acid residues of EcIYRS were amplified by PCR with use of primers PhA3 (SEQ. ID. NO: 43) and PhA4 (SEQ. ID. NO: 44) and by PCR with use of primers PhA5 (SEQ. ID. NO: 45) and PhA6 (SEQ. ID. NO: 46).

Next, a reaction solution containing the PCR-amplified DNA coding for the B3/4 domain of *P. horikoshii*, the PCR-amplified DNA coding for the N (1-304) and C (305-424) terminals of EcIYRS, and primers PhA7 (SEQ. ID. NO: 47) and PhA8 (SEQ. ID. NO: 48) was prepared, and overlap PCR was carried out, whereby a DNA fragment coding for a fusion protein in which the B1, B2, and B3/4 domains of *P. horikoshii* had been inserted into the alpha-helical domain (AC) of EcIYRS was amplified.

The amplified DNA was cloned between the NdeI and XhoI sites of an expression vector pET-26b so that a His tag is added to the C terminal. Thus produced was a Ped-AC-IYRS expression plasmid. The base sequence of Ped-AC-IYRS is represented by SEQ. ID. NO: 14.

The mutation that inactivates editing reaction was introduced site-specifically by amplifying the whole plasmid by PCR.

The expression and purification of the Ped-AC-IYRS protein were performed in the same manner as in Example 4. Further, the expression was confirmed by SDS-PAGE (not shown).

It should be noted that the mutant with inactivated editing activity was produced in the same manner (Ped$^{mu}$-AC-IYRS). The mutation that inactivates the editing reaction domain is the same as in the case of Ped$^{mu}$-N-IYRS described in Example 4. The Ped$^{mu}$-AC-IYRS expression plasmid was produced in the same manner as Ped$^{mu}$-N-IYRS described in Example 4, except that Ped-AC-IYRS was used as a template instead.

EXAMPLE 8

Preparation of Amber Suppressor tRNA$^{Tyr}$

Amber suppressor tRNA$^{Tyr}$ was prepared with use of a T7 RNA polymerase according to a method devised by Nureki et al. (Nureki O et al., *J Mol Biol* 236, 710-724 1994).

The sequence of the anticodon site of *Escherichia coli* tRNA$^{Tyr}$ was made CUA so as to correspond to an amber codon. A T7 promoter sequence (SEQ. ID. NO: 73) was added upstream of a DNA sequence serving as a template for tRNA. CCAGG was designed so that a site corresponding to the CCA terminal of tRNA could be cleaved by a restriction endonuclease Mva I. The sequence is as short as 120 bases. Therefore, a DNA fragment was amplified by PCR with use of a combination of two primers without a template, and the amplified DNA fragment was cloned into a pUC18 vector.

The DNA fragment including a cloned region was amplified by PCR with use of M13 forward and M13 reverse primers. The amplified DNA fragment was cleaved by Mva I so that one terminal is CCA. With use of the DNA fragment as a template, tRNA was transcribed with use of a T7 RNA polymerase. The transcription reaction by a T7 RNA polymerase was performed by incubation in a reaction solution of (a composition) at 37° C. for 5 hours. When 2 hours had elapsed since the start of incubation, a T7 RNA polymerase was added in an amount a tenth as large as the amount of the first T7 RNA polymerase. The reaction solution was subjected to phenol/chloroform extraction. After ammonium acetate had been added as a salt to the extract, an isopropanol precipitation was performed. The precipitate was dissolved in 2 ml of 10 mM Hepes-Na (pH 7.5). After the dissolution, the solution was passed through a PD-10 desalination column (GE Healthcare, Inc.), whereby unreacted nucleotides were removed. Another ethanol precipitation was performed. The precipitate was dissolved in a solution containing 10 mM Hepes-Na (pH 7.5) and 2 mM MgCl$_2$. After denaturation of tRNA at 80° C. for 2 minutes, tRNA was rewound by slow cooling.

EXAMPLE 9

Determination of the Aminoacylation Activity of Ped-CP1-IYRS

Figure 5:
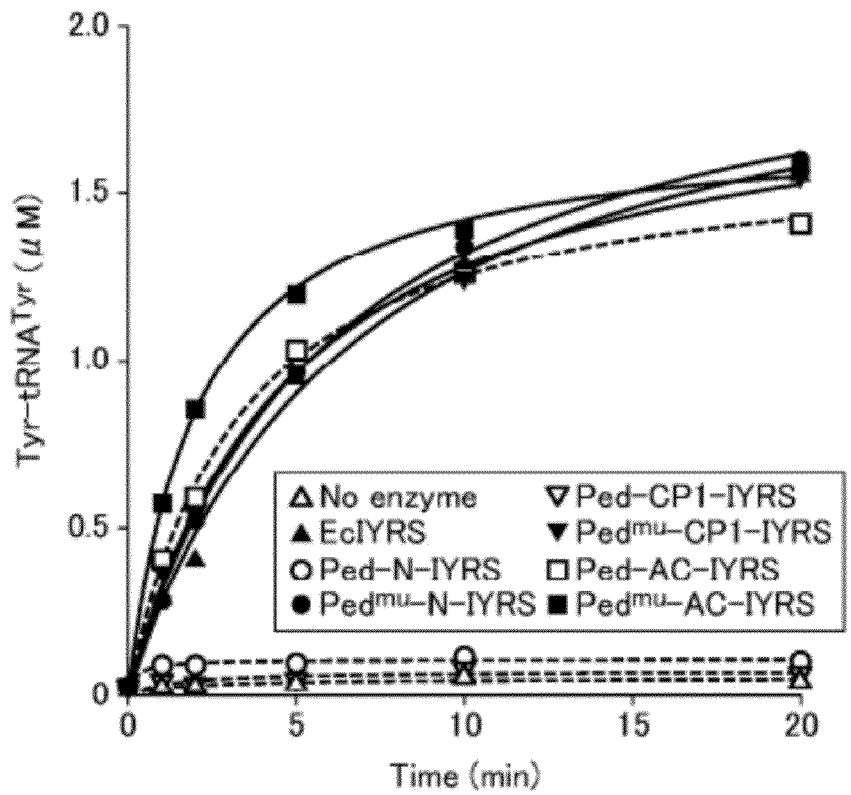
FIG. 5, showing an embodiment of the present invention, shows the hydrolysis activity of fusion proteins.

Next, the aminoacylation activity (tyrosylation activity) of each of the fusion proteins was determined. The determination was performed in the same manner as in Example 5. The results are shown in FIG. 5. It should be noted that the activity of each fusion protein having a mutation introduced into an editing reaction domain thereof is indicated by a change in activity of EcIYRS due to insertion of an editing reaction domain.

As shown in FIG. 5, Ped-CP1-IYRS had little tyrosine added to tRNA$^{Tyr}$.

Further, in Ped-AC-IYRS, tyrosylation was detected. It should be noted that there was no decrease in tyrosylation of EcIYRS to tRNA$^{Tyr}$ due to a mutant produced in the same manner as Ped-AC-IYRS, except for insertion of an inactive editing reaction domain, and tyrosylation was detected as with Ped-AC-IYRS. That is, in Ped-AC-IYRS, there was no hydrolysis by an editing reaction domain.

Next, each of the fusion proteins was assayed for substrate specificity. Urea-denatured acidic PAGE was performed to check whether or not each fusion protein recognized 3-iodotyrosine. The reaction was performed in the same manner as in the aforementioned determination of the N-terminal fusion proteins except that the concentration of Ped-CP1-IYRS was 1 mM or 2 mM and the reaction temperature was 24° C. or 37° C.

Figure 6:
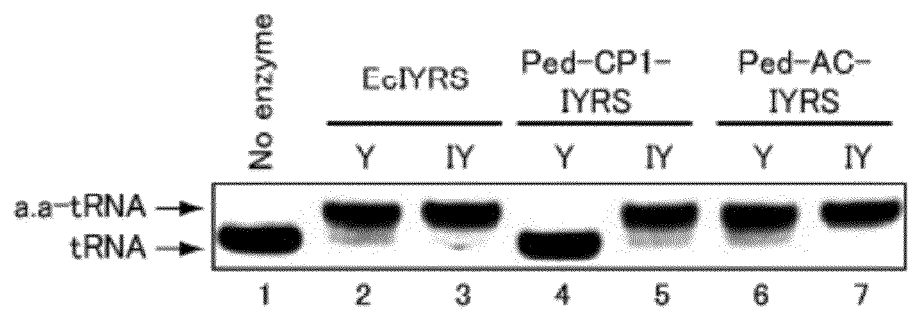
FIG. 6, showing an embodiment of the present invention, shows the substrate recognition specificity of fusion proteins.

FIG. 6 shows the results from the mutants. As shown in FIG. 6, Ped-CP1-IYRS was observed to recognize 3-iodotyrosine. Under a reaction condition of 37° C. for 1 minute, an almost complete shift in tRNA was observed. Further, under a reaction condition of 24° C., a shift in band was observed even after a further prolonged period of reaction. Meanwhile, as with EcIYRS, Ped-AC-IYRS recognized 3-iodotyrosine.

EXAMPLE 10

Determination of the Hydrolysis Activity of Ped-CP1-IYRS and Ped-N-IYRS with Respect to Tyrosyl tRNA Next, Ped-CP1-IYRS, which had not tyrosylated tRNA$^{Tyr}$ in aminoacylation in Example 9, was checked for its hydrolysis activity with respect to tyrosyl tRNA. Further, Ped-N-IYRS, which had been produced in Example 4, was studied, too.

Under the same conditions as in the determination of the aminoacylation activity of the N-terminal fusion protein, [$^{14}$C]-tyrosyl tRNA$^{Tyr}$ was produced with use of a wild-type EcTyrRS as an enzyme. After 30 minutes of reaction, the protein was removed by phenol/chloroform treatment, and [$^{14}$C]-tyrosyl tRNA$^{Tyr}$ was precipitated by ethanol precipitation. In order to inhibit a naturally-occurring hydrolysis, the resultant precipitate was dissolved in a 10 mM sodium citrate buffer solution (pH 4.5).

The hydrolysis reaction was performed by adding 2.2 mM [$^{14}$C]-tyrosyl tRNA$^{Tyr}$ and 50 nM Ped-N-IYRS or Ped-CP1-IYRS to a buffer solution (100 mM Tris-Cl (pH 7.5), 15 mM MgCl$_2$). As with the activity determination of aminoacylation, the remaining [$^{14}$C]-tyrosyl tRNA$^{Tyr}$ was quantified by a liquid scintillation counter.

Figure 7:
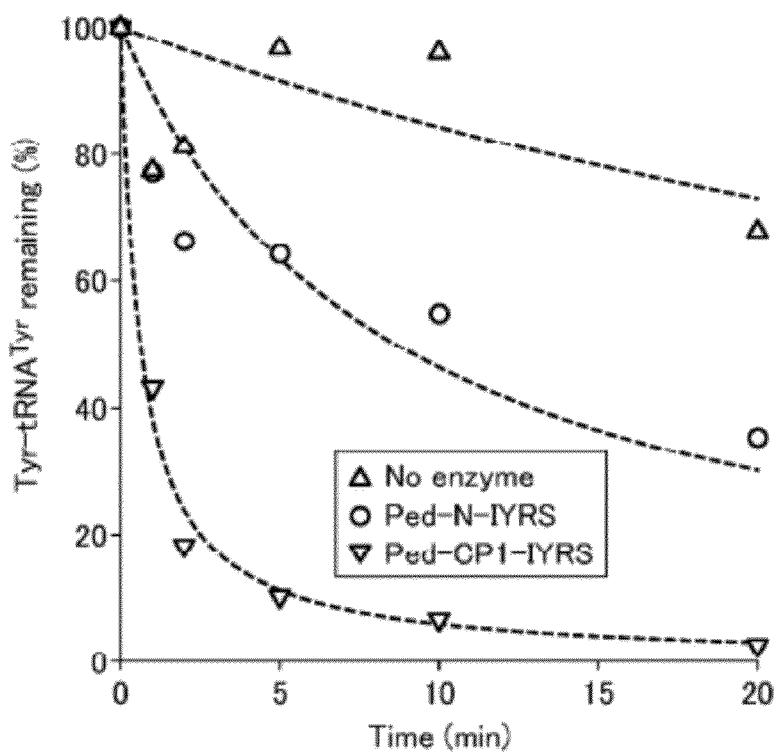
FIG. 7, showing an embodiment of the present invention, shows the hydrolysis activity of fusion proteins.

FIG. 7 shows the results of the hydrolysis activity of Ped-N-IYRS and Ped-CP1-IYRS.

As shown in FIG. 7, both of the mutants exhibited hydrolysis activity. Further, Ped-CP1-IYRS exhibited higher hydrolysis activity than Ped-N-IYRS. It seemed that tyrosyl tRNA can be hydrolyzed more efficiently when the editing reaction domain is inserted into the CP1 domain than when the editing reaction domain is at the N terminal.

Next, it was confirmed whether or not Ped-CP1-IYRS introduces tyrosine or 3-iodotyrosine into an amber codon in a wheat germ cell-free translation system. As the wheat germ cell-free translation system, an RTS100 wheat germ CECF kit (Roche) was used, and the protocol that came with the kit was followed. Since this reaction is performed at 24° C., the structure of Ped-CP1-IYRS is not disarrayed, so that it is expected that 3-iodotyrosine will be recognized.

By adding, to this kit, a plasmid into which a gene controlled by a T7 promoter has been incorporated, the gene can be expressed. It is known that *Escherichia coli*-derived EcIYRS and *Escherichia coli* tRNA$^{Tyr}$ are orthogonalized to each other in a wheat germ translation system (i.e., that EcIYRS does not react with tRNA inherent in the cells and *Escherichia coli* tRNA$^{Tyr}$ does not react with aaRSs inherent in the cells) (Kiga, D., Sakamoto, K., Kodama, K., Kigawa, T., Matsuda, T., Yabuki, T., Shirouzu, M., Harada, Y., Nakayama, H., Takio, K., Hasegawa, Y., Endo, Y., Hirao, I., Yokoyama, S., An engineered *Escherichia coli* tyrosyl-tRNA synthetase for site-specific incorporation of an unnatural amino acid into proteins in eukaryotic translation and its application in a wheat germ cell-free system. *Proc Natl Acad Sci USA,* 2002, 99, 9715-9720).

As a reporter protein to be expressed, GST (glutathione-S-transferase) into which an amber codon has been introduced was used. The GST gene has a redundant sequence added upstream thereof, and the redundant sequence has the amber codon introduced thereinto (GST (Am)) (SEQ. ID. NO: 49) (donated from Dr. Kobayashi of RIKEN). A DNA fragment coding for GST (Am) was amplified by PCR, and was cloned at the EcoRV-XhoI site of a vector pEU3-N11 (TOYOBO Co., Ltd.). When EcIYRS and *Escherichia coli* amber suppressor tRNA are added to the cell-free translation system, tyrosine is introduced into the amber codon, and the GST protein is translated. That is, the aminoacylation activity of EcIYRS can be estimated by the amount of the GST protein.

To a reaction solution included in the wheat germ cell-free translation system kit, 5 mM *Escherichia coli* amber suppressor tRNA, 1 mM 3-iodotyrosine, 2 mM aaRS, and 40 ng/μl of a plasmid coding for GST (Am) were added, and then were allowed to react at 24° C. for 6 hours. The GST protein thus translated was detected by western blotting with use of GST antibodies.

Figure 8:
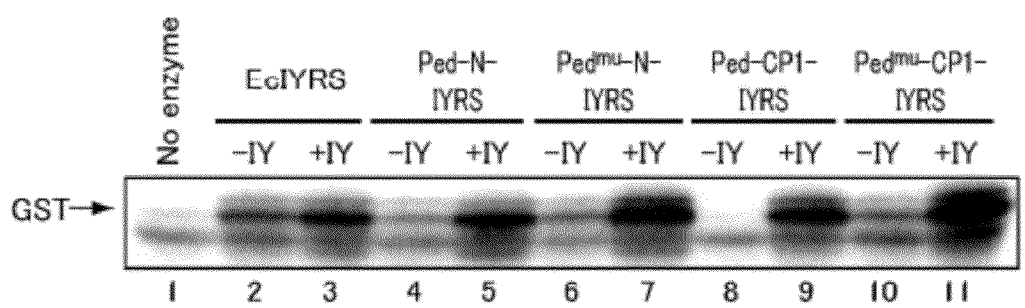
FIG. 8, showing an embodiment of the present invention, is a western blotting diagram showing the results of protein synthesis in a cell-free translation system with use of fusion proteins.

FIG. 8 shows the results of western blotting.

As shown in FIG. 8, Ped-CP1-IYRS did not express GST at all in the absence of 3-iodotyrosine (Lane 8). This shows that the editing reaction domain of Ped-CP1-IYRS functions appropriately in a translation system. Further, in the presence of 3-iodotyrosine, Ped-CP1-IYRS expressed the same level of GST as EcIYRS. That is, there was no decrease in aminoacylation activity due to insertion of the editing reaction domain. Therefore, Ped-CP1-IYRS could achieve specific recognition with respect to 3-iodotyrosine.

Ped$^{mu}$-CP1-IYRS exhibited a band of GST in the absence of 3-iodotyrosine as with EcIYRS, and in addition, expressed the same level of GST as EcIYRS in the presence of 3-iodotyrosine.

It should be noted that Ped-CP1-IYRS has a linker, represented by SEQ. ID. NO: 50, which has been inserted between the Rossman-fold domain and the N-terminal side of the editing reaction peptide and a linker, represented by SEQ. ID. NO: 51, which has been inserted the Rossman-fold domain and the C-terminal side. These linkers have been inserted in accordance with the sequences of the primers used in the aforementioned overlap PCR. It was found that substitution of linkers in Ped-CP1-IYRS has an influence on the activity to specifically recognize 3-iodotyrosine and synthesize aminoacylated tRNA. Among such Ped-CP1-IYRSs, a Ped-CP1-IYRS in which a linker represented by SEQ. ID. NO: 50 is used at the N-terminal side and a linker represented by SEQ. ID. NO: 51 is used at the C-terminal side exhibited the highest activity.

EXAMPLE 11

Site-specific Introduction of Iodotyrosine into Proteins with Use of Ped-CP1-IYRS in Cultured Mammalian Cells In order to further verify the usefulness of Ped-CP1-IYRS, an experiment for introducing iodotyrosine into proteins with use of Ped-CP1-IYRS in cultured mammalian cells was conducted. The experiment was all conducted according to the procedures and methods described in "Sakamoto, K., Hayashi, A., Sakamoto, A., Kiga, D., Nakayama, H., Soma, A., Kobayashi, T., Kitabatake, M., Takio, T., Saito, K., Shirouzu, M., Hirao, I., and Yokoyama, S., Site-specific incorporation of an unnatural amino acid into proteins in mammalian cells, *Nucleic Acids Research* 30, 4692-4699, 2002". In expressing Ped-CP1-IYRS in cultured mammalian cells (CHO cells), such methods for expressing TyrRS and IYRS as described in the above document were used without modification. Therefore, the expressed Ped-CP1-IYRS has a FLAG tag added to the C terminal.

Figure 9:
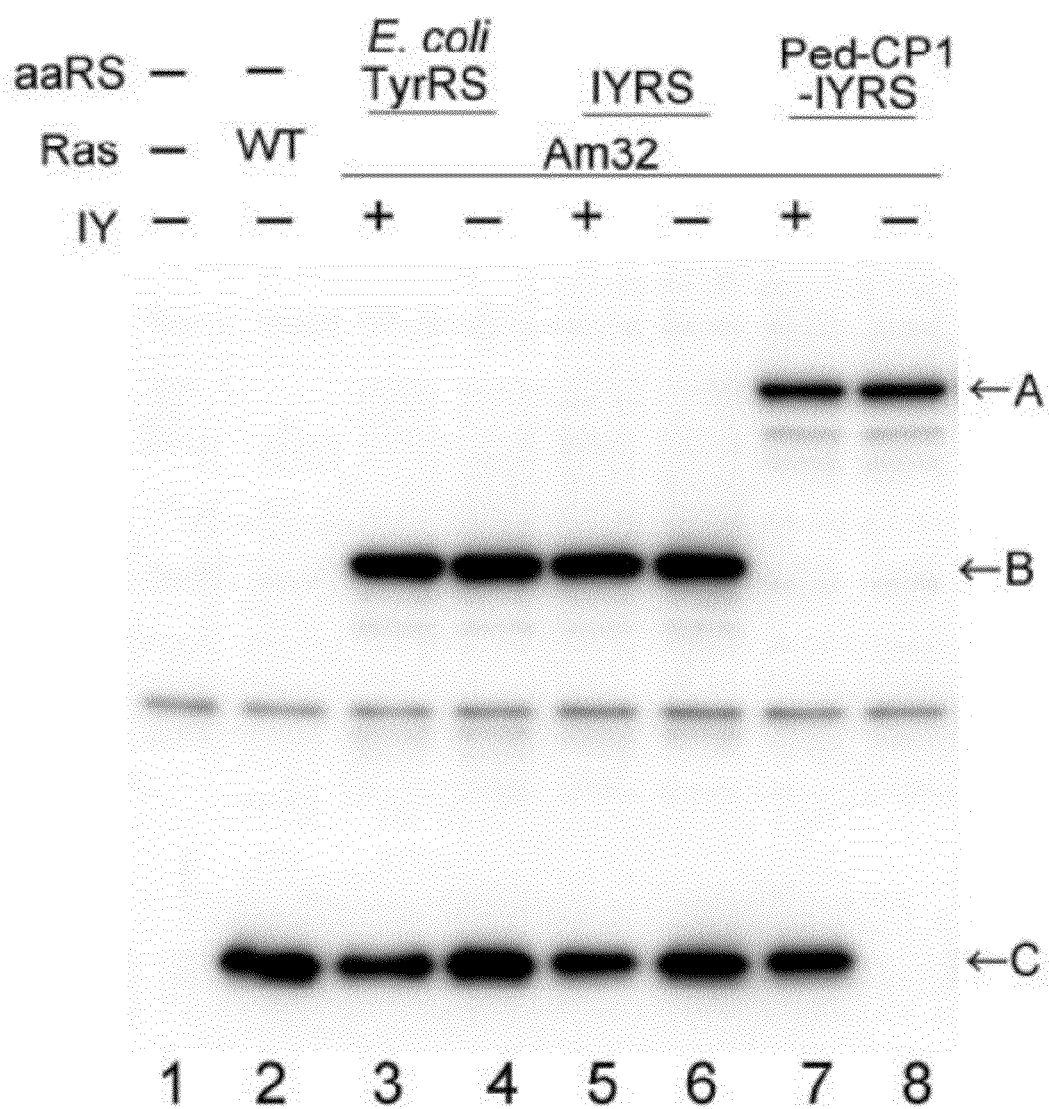
FIG. 9, showing an embodiment of the present invention, is a western blotting diagram showing the results of protein synthesis in cultured mammalian cells with use of fusion proteins.

The 32nd codon of the RAS gene was substituted with an amber codon (Am32), and an attempt to introduce iodotyrosine (IY) into the position was made. It should be noted that a full-length RAS protein is expressed when some sort of amino acid has been introduced into the position. Every protein thus forcibly expressed has a FLAG tag added thereto, and the expression of proteins was detected by western blotting with use of anti-FLAG antibodies. The results are shown in FIG. 9. In FIG. 9, Bands A, B, and C correspond to Ped-CP1-IYRS, IYRS or *Escherichia coli* TyrRS, and RAS proteins, respectively.

First, a control experiment was conducted to express a RAS gene including no amber codon (Lane 2) and confirm the position of a full-length RAS protein on a western blot (Band C). Each of Lanes 3 and 4 shows that a full-length RAS is expressed also when *Escherichia coli* TyrRS is expressed. The TyrRS recognizes not iodotyrosine but a normal tyrosine, and as such, has tyrosine introduced into the amber site thereof, regardless of whether IY has been added to the medium (IY+) or not (IY−). See the case of expression of a mutant IYRS of TyrRS that recognizes iodotyrosine (Lane 5). In the presence of iodotyrosine, the amino acid is introduced into the amber site, with the result that a full-length RAS is expressed. It should be noted here that, as described in the document above, the amino acid that IYRS introduces into its amber site at the time of addition of iodotyrosine is iodotyrosine. However, IYRS still has an affinity to tyrosine. For this reason, in the absence of iodotyrosine, tyrosine is introduced into the amber site, with the result that a full-length RAS is expressed after all (Lane 6).

See the case of expression of Ped-CP1-IYRS. At the time of addition of iodotyrosine, a full-length RAS was expressed. This shows that the mutant has activity to introduce iodotyrosine into the amber site in the mammalian cells. It is also shown that, without addition of iodotyrosine, no full-length RAS is expressed, and as a result, Ped-CP1-IYRS does not introduce tyrosine into the amber site. That is, as with the results from the wheat germ cell-free translation system shown in FIG. 8, Ped-CP1-IYRS exhibits drastically improved specificity to iodotyrosine also the cultured mammalian cells.

EXAMPLE 12

Site-specific Introduction of Iodotyrosine into Proteins with Use of Ped-CP1-IYRS in Cultured *Drosophila* Cells In order to further verify the usefulness of Ped-CP1-IYRS, an experiment for introducing iodotyrosine into proteins with use of Ped-CP1-IYRS in cultured *drosophila* cells was conducted.

In expressing Ped-CP1-IYRS in cultured *drosophila* cells (S2 cells), a commercially available expression vector pMT/V5-His A (Invitrogen Corporation) was used. As a result, the expressed Ped-CP1-IYRS has an HA tag added to the C terminal. In expressing *Bacillus stearothermophilus*-derived suppressor tRNA$^{Tyr}$ in the S2 cells, a U6 promoter (DU6-2 promoter) described in "Wakiyama M., Matsumoto T., Yokoyama S., *Drosophila* U6 promoter-driven short hairpin RNAs effectively induce RNA interference in Schneider 2 cells, *Biochemical and Biophysical Research Communications* 331, 1163-1170, 2005" was used upstream of a suppressor tRNA$^{Tyr}$ sequence described in "Sakamoto, K. et al., *Nucleic Acids Research* 30, 4692-4699, 2002".

The 91st codon of the lacZ gene was substituted with an amber codon (LacZ (UAG)), and an attempt to introduce iodotyrosine (IY) into the position was made. It should be noted that when some sort of amino acid has been introduced into the position, a full-length LacZ protein is expressed to exhibit β-galactosidase activity. The results are shown in Table 1.

First, a control experiment was conducted to express IYRS and confirm the β-galactosidase activity of a full-length LacZ protein. In the case of use of LacZ (UAG) as LacZ, LacZ (UAG) exhibited activity at 17.4% of the expression level of the wild-type LacZ (LacZ WT), which proved the usefulness of an iodotyrosine introduction system in cultured *drosophila* cells.

Next, see the case of expression of Ped-CP1-IYRS. At the time of addition of iodotyrosine, a full-length LacZ was expressed. This shows that the mutant has activity to introduce iodotyrosine into the amber site in the S2 cells. Meanwhile, without addition of iodotyrosine, the expression level of full-length LacZ proteins decreased to approximately 4% compared with the time of addition of iodotyrosine. This shows that Ped-CP1-IYRS hardly introduces tyrosine into the amber site.

That is, in addition to the results from the wheat germ cell-free translation system in FIG. 8 and the results from the cultured mammalian cells in FIG. 9, Ped-CP1-IYRS exhibits drastically improved specificity to iodotyrosine also in the *drosophila* cells. It was also shown that in an experimental system using S2 cells, Ped-CP1-IYRS exhibits not only specificity but also is comparable in activity to IYRS in terms of iodotyrosine introduction efficiency.

TABLE 1

| LacZ | LacZ WT | LacZ(UAG) | LacZ(UAG) | LacZ(UAG) |
|---|---|---|---|---|
| aaRS | IYRS | IYRS | Ped-CP1-IYRS | Ped-CP1-IYRS |
| IY | — | 1 mM | 1 mM | — |
| % | 100.0 | 17.4 | 15.9 | 0.7 |

As described above, a polypeptide according to the present invention is a polypeptide having aminoacyl-tRNA synthetase activity, the polypeptide including: an altered polypeptide obtained by altering an arginyl-tRNA synthetase, a cysteinyl-tRNA synthetase, a methionyl-tRNA synthetase, a glutaminyl-tRNA synthetase, a glutamyl-tRNA synthetase, a lysyl-tRNA synthetase, a tyrosyl-tRNA synthetase, or a tryptophanyl-tRNA synthetase so that an unnatural amino acid is recognized; and an editing polypeptide containing an editing reaction active site derived from a phenylalanyl-tRNA synthetase, a leucyl-tRNA synthetase, an isoleucyl-tRNA synthetase, a valyl-tRNA synthetase, an alanyl-tRNA synthetase, a prolyl-tRNA synthetase, or a threonyl-tRNA synthetase, the editing polypeptide having been either inserted between a Rossman-fold N domain and a Rossman-fold C domain that exist in the altered polypeptide, or bound to an N terminal of the altered polypeptide. This brings about an effect of high specificity to an amino acid to be recognized.

The present invention makes it possible to provide an aaRS that exhibits high specificity to an amino acid to be recognized, and as such, makes it possible to produce a protein with various functions by using an unnatural amino acid. Therefore, the present invention can be applied in the field of biochemistry and the drug industry such as the industry for development of new drugs.

The concrete embodiments and examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

What is claimed is:

1. An altered tyrosyl-tRNA synthetase polypeptide that recognizes a tyrosine derivative, the altered tyrosyl-tRNA synthetase comprising an insertion of an editing polypeptide or fragment thereof containing the B3/4 domain of the beta-subunit of a phenylalanyl-tRNA synthetase at the CP1 domain positioned between the Rossman-fold N domain and the Rossman-fold C domain of the altered tyrosyl-tRNA synthetase polypeptide, or bound to the N-terminus of the altered tyrosyl-tRNA synthetase polypeptide.

2. The polypeptide as set forth in claim 1, wherein the editing polypeptide has been inserted into a CP1 domain that lies between the Rossman-fold N-domain and the Rossman-fold C domain.

3. The polypeptide as set forth in claim 1, wherein a linker polypeptide that connects the editing polypeptide with the altered polypeptide has been further inserted.

4. The polypeptide as set forth in claim 1, wherein the tyrosyl-tRNA synthetase is derived from a eukaryotic organism or eubacteria.

5. The polypeptide as set forth in claim 4, wherein the eubacteria is *Escherichia coli*.

6. The polypeptide as set forth in claim 1, wherein the tyrosine derivative is 3-iodotyrosine.

7. The polypeptide as set forth in claim 1, which is derived from a tyrosyl-tRNA synthetase polypeptide consisting of the amino acid sequence represented by SEQ ID NO: 1.

8. The polypeptide as set forth in claim 1, wherein the phenylalanyl-tRNA synthetase is derived from a eukaryotic organism or archaebacteria.

9. The polypeptide as set forth in claim 8, wherein the archaebacteria belongs to the genus *Pyrococcus*.

10. The polypeptide as set forth in claim 8, wherein the archaebacteria is *Pyrococcus horikoshii*.

11. The polypeptide as set forth in claim 1, wherein the editing polypeptide consists of the amino acid sequence represented by SEQ ID NO: 2; and can hydrolyze tyrosine bound to tyrosyl-tRNA or hydrolyze a tyrosyl adenylate intermediate into tyrosine and an inorganic phosphoric acid.

12. The polypeptide as set forth in claim 1, wherein the polypeptide consists of the amino acid sequence represented by SEQ ID NO: 3; can hydrolyze tyrosine bound to tyrosyl-tRNA or hydrolyze a tyrosyl adenylate intermediate into tyrosine and an inorganic phosphoric acid; and can aminoacylate a tyrosyl-tRNA with an unnatural amino acid.

13. A polynucleotide coding for a polypeptide having aminoacyl-tRNA synthetase activity as set forth in claim 1.

14. A method for producing a tyrosyl-tRNA synthetase polypeptide with an altered aminoacyl-tRNA synthetase activity that recognizes a tyrosine derivative, the method comprising, and the steps of:
   i) preparing a polynucleotide encoding the altered tyrosyl-tRNA synthetase according to claim 1; and
   ii) expressing the polypeptide encoded by the polynucleotide obtained in the preparing step.

* * * * *